US010495900B2

(12) United States Patent
Smathers et al.

(10) Patent No.: US 10,495,900 B2
(45) Date of Patent: *Dec. 3, 2019

(54) OPHTHALMIC LENS CUSTOMIZATION SYSTEM AND METHOD

(71) Applicant: PERFECT IP, LLC, Dallas, TX (US)

(72) Inventors: Steven Edward Smathers, Dallas, TX (US); Ruth Sahler, Irvine, CA (US)

(73) Assignee: PERFECT IP, LLC, Dallas, TX (US)

( * ) Notice: Subject to any disclaimer, the term of this patent is extended or adjusted under 35 U.S.C. 154(b) by 96 days.

This patent is subject to a terminal disclaimer.

(21) Appl. No.: 15/870,140

(22) Filed: Jan. 12, 2018

(65) Prior Publication Data
US 2018/0231800 A1    Aug. 16, 2018

Related U.S. Application Data

(60) Provisional application No. 62/460,043, filed on Feb. 16, 2017.

(51) Int. Cl.
G02C 7/00 (2006.01)
G02C 7/02 (2006.01)
(Continued)

(52) U.S. Cl.
CPC .............. *G02C 7/024* (2013.01); *A61F 9/008* (2013.01); *A61F 9/00831* (2013.01);
(Continued)

(58) Field of Classification Search
CPC ........ G02C 7/024; G02C 7/027; G02C 7/041; G02C 7/081; G02C 7/025; G02C 7/028;
(Continued)

(56) References Cited

U.S. PATENT DOCUMENTS

| 4,269,307 A | 5/1981 | LaHaye |
| 9,023,257 B2 | 5/2015 | Sahler et al. |

(Continued)

FOREIGN PATENT DOCUMENTS

EP    0865261 B1    6/1999

OTHER PUBLICATIONS

D. Michael Colvard, MD, FACS; "Achieving Excellence in Cataract Surgery, A Step-by-Step Approach"; Chapter 12, 2009.

*Primary Examiner* — William R Alexander
*Assistant Examiner* — Henry A Duong
(74) *Attorney, Agent, or Firm* — David W. Carstens; Jeffrey G. Degenfelder; Carstens & Cahoon, LLP

(57) ABSTRACT

A system/method allowing personalized ex vivo customization of a generic ophthalmic lens blank (OLB) or ophthalmic lens with known diopter (OKD) based on localized field-measured patient characteristics is disclosed. The OLB is composed of an acrylic material that has been infused with an ultraviolet (UV) absorbing compound rendering it amenable to customized spatial modification (CSM) of its refractive index via the use of pulsed laser radiation (PLR). The CSM of refractive index eliminates the need for remote laboratory fabrication of a customized intraocular lens (IOL) for the patient. The OLB is retained within a secured lens container (SLC) providing for precise physical orientation of the OLB haptics and OLB lens structure with respect to the application of PLR to the OLB. The SLC contains a lens filler material (LFM) covering the OLB and is hermetically sealed after the OLB has been positioned within the SLC interior and prior to sterilization of the SLC+OLB combination.

50 Claims, 96 Drawing Sheets

(51) Int. Cl.
  *A61F 9/008* (2006.01)
  *G02C 7/04* (2006.01)
  *B29C 71/04* (2006.01)
  *G02C 7/06* (2006.01)
  *A61F 2/16* (2006.01)
  *G02C 7/08* (2006.01)
  *B29L 11/00* (2006.01)
  *B29C 35/08* (2006.01)

(52) U.S. Cl.
  CPC .......... *A61F 9/00838* (2013.01); *B29C 71/04* (2013.01); *G02C 7/027* (2013.01); *G02C 7/049* (2013.01); *G02C 7/061* (2013.01); *A61F 2/1627* (2013.01); *A61F 2/1648* (2013.01); *A61F 2009/00887* (2013.01); *A61F 2240/00* (2013.01); *B29C 2035/0827* (2013.01); *B29C 2035/0838* (2013.01); *B29C 2791/009* (2013.01); *B29K 2995/0092* (2013.01); *B29L 2011/0016* (2013.01); *G02C 7/041* (2013.01); *G02C 7/081* (2013.01)

(58) Field of Classification Search
  CPC . G02C 7/061; G02C 7/049; B29L 2011/0016; A61F 2009/00887; A61F 2/1648; A61F 2/1627; A61F 9/00831; A61F 9/00838; A61F 9/008; A61F 2240/00; B29C 2791/009; B29C 71/04; B29C 2035/0838; B29C 2035/0827; B29K 2995/0092
  USPC ..................................................... 351/159.74
  See application file for complete search history.

(56) References Cited

U.S. PATENT DOCUMENTS

2005/0079096 A1*  4/2005  Brown-Skrobot ........ A61L 2/10
                                                                422/24
  2005/0288785 A1* 12/2005  Portney ..................... A61F 2/16
                                                                623/6.46
  2014/0135920 A1*  5/2014  Sahler ....................... A61F 2/16
                                                                623/6.27
  2014/0277437 A1   9/2014  Currie

* cited by examiner

2800

3000

3200

3800

*FIG. 40*
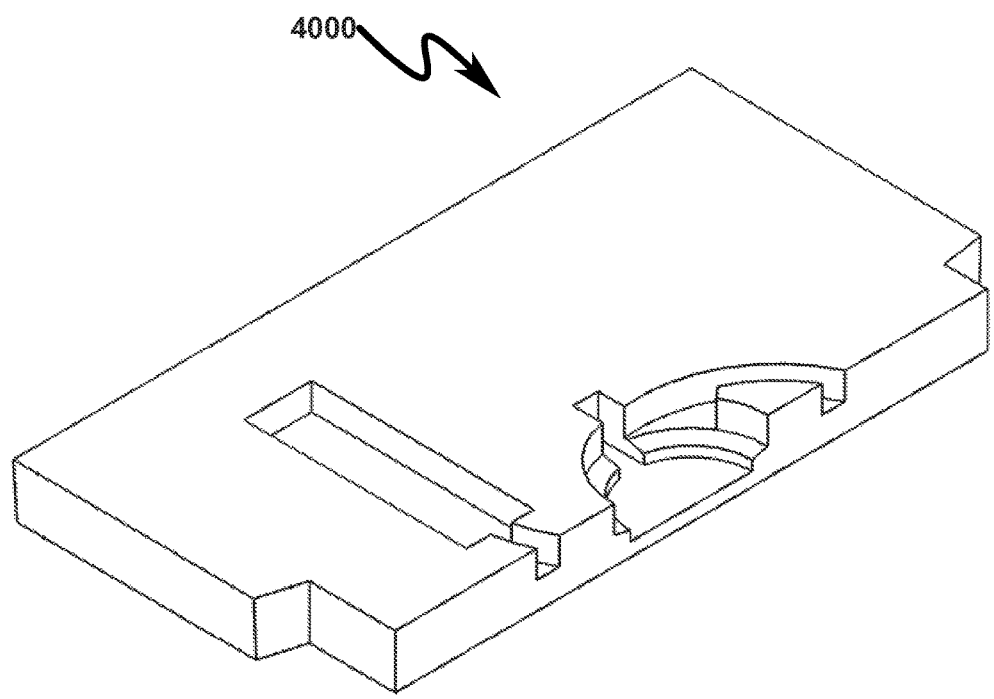
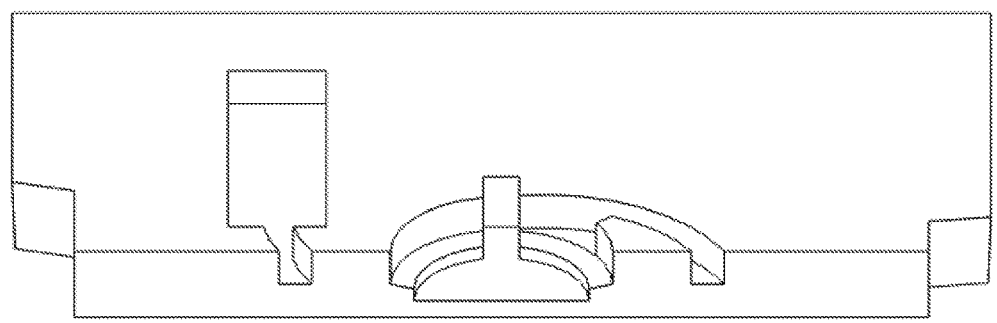
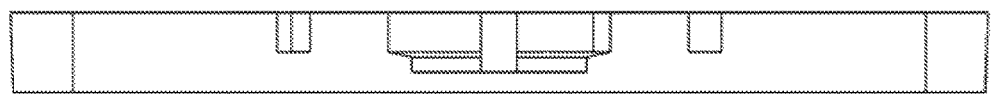

FIG. 64
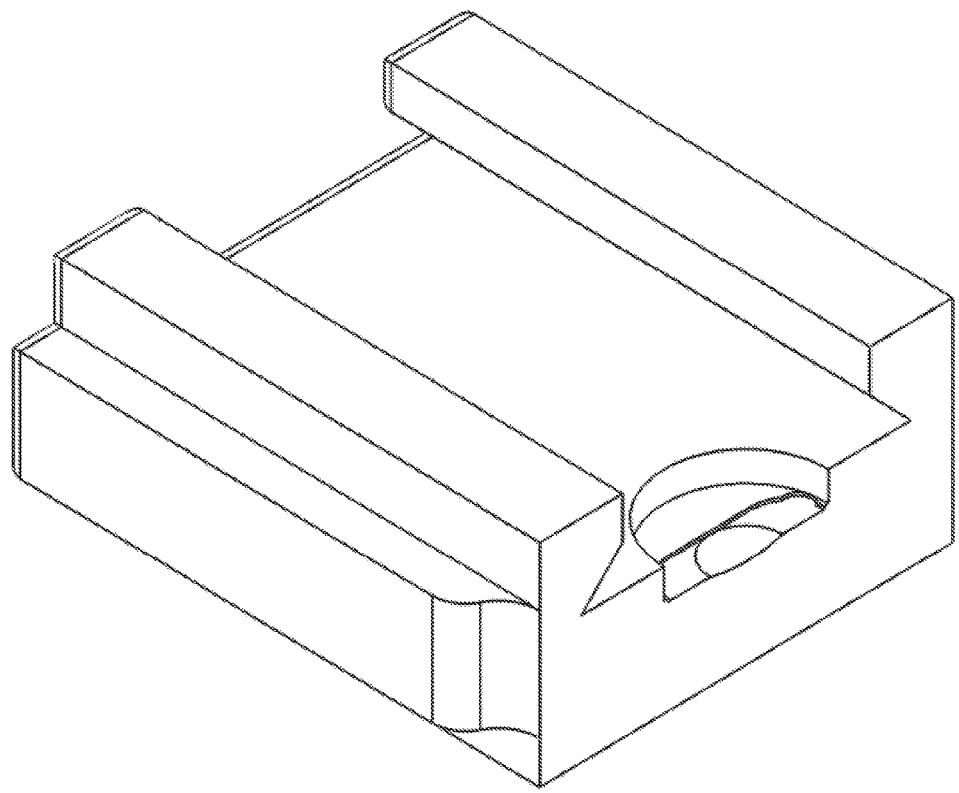

6800

8300

FIG. 89
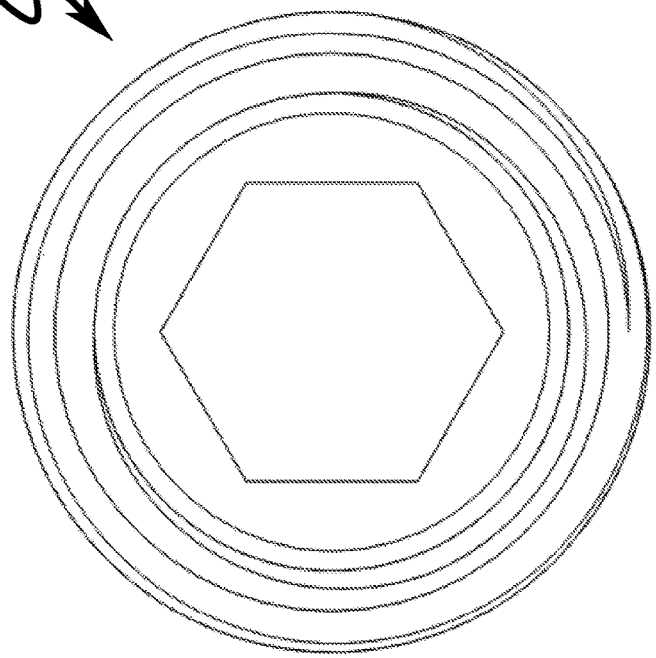
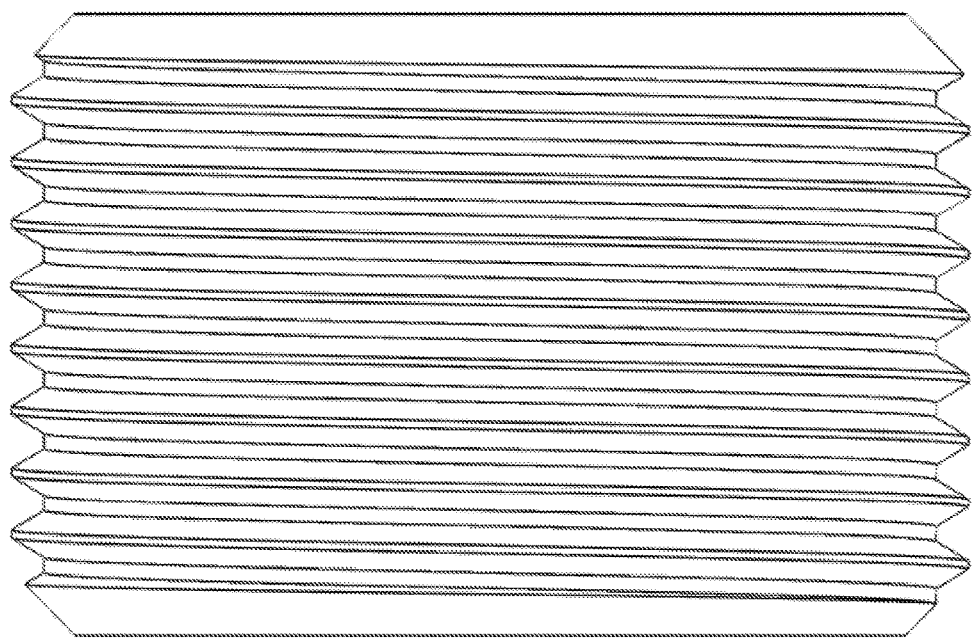

OPHTHALMIC LENS CUSTOMIZATION SYSTEM AND METHOD

CROSS REFERENCE TO RELATED APPLICATIONS

This application claims benefit under 35 U.S.C. § 119 and incorporates by reference U.S. Provisional Patent Application for OPHTHALMIC LENS CUSTOMIZATION SYSTEM AND METHOD by inventors Steven Edward Smathers and Ruth (nmn) Sahler, filed with the USPTO on Feb. 16, 2017, with Ser. No. 62/460,043. This application further includes by reference U.S. Pat. No. 9,023,257 issued on May 5, 2015 for BYDROPHILICITY ALTERNATION SYSTEM AND METHOD by inventors Ruth (nmn) Sahler, Stephen Q. Zhou, and Josef F. Bille.

PARTIAL WAIVER OF COPYRIGHT

All of the material in this patent application is subject to copyright protection under the copyright laws of the United States and of other countries. As of the first effective filing date of the present application, this material is protected as unpublished material.

However, permission to copy this material is hereby granted to the extent that the copyright owner has no object ion to the facsimile reproduction by anyone of the patent documentation or patent disclosure, as it appears in the United States Patent and Trademark Office patent file or records, but otherwise reserves all copyright rights whatsoever.

FIELD OF THE INVENTION

The present invention relates to the field customization of an ophthalmic lens. By way of example only, the present invention teaches a laser system and a method for modifying the refractive index of an optical lens in a predetermined region inside the lens bulk body. The material used in the experiments described herein as applied to the present invention is a polymeric acrylic lens material (PLM) but this material selection is exemplary and should not be treated as a limitation of the present invention.

PRIOR ART AND BACKGROUND OF THE INVENTION

U.S. Pat. No. 9,023,257 issued on May 5, 2015 for HYDROPHILICITY ALTERATION SYSTEM AND METHOD by inventors Ruth (nmn) Sahler, Stephen Q. Zhou, and Josef F. Bille teaches that the refractive index of a polymer-based lens may be modified using pulsed laser radiation.

The system as described in this issued patent generally requires the use of a controlled laboratory environment to ensure that the manufactured lens is accurately formed and is properly sterilized and thus safe for insertion into a patient. There is no provision in the prior art for field customization of lenses that are properly prepared for ex vivo insertion into a patient.

DEFICIENCIES IN THE PRIOR ART

While the prior art as detailed above can theoretically be used to form optical, lenses, it suffers from the following deficiencies:

Prior art lens fabrication systems do not address lens sterilization procedures necessary to ensure patient safety.

Prior art lens fabrication systems do not address field customization of the lens material.

Prior art lens fabrication systems do not address practical issues relating to the fixturing and orientation of lens blank materials.

To date the prior art has not fully addressed these deficiencies.

OBJECTIVES OF THE INVENTION

Accordingly, the objectives of the present invention are (among others) to circumvent the deficiencies in the prior art and affect the following objectives:

(1) provide for a system and method that permits the field customization of an ophthalmic lens that address lens sterilization issues for patient safety;

(2) provide for a system and method that addresses field customization of ophthalmic lens material; and (3) provide for a system and method that address practical issues relating to the fixturing and orientation of lens blank material for field customization.

While these objectives should not be understood to limit the teachings of the present invention, in general these objectives are achieved in part or in whole by the disclosed invention that is discussed in the following sections. One skilled in the art will no doubt be able to select aspects of the present invention as disclosed to affect any combination of the objectives described above.

BRIEF SUMMARY OF THE INVENTION

The present invention pertains to a system, method, and product-by-process wherein a pulsed laser system is used to customize an ophthalmic lens ex vivo for later use in a patient. Pulsed laser radiation is controlled by a computer system and controlled optics to modify the internal characteristics of a generic ophthalmic lens blank (OLB) or ophthalmic lens with known diopter (OKD) based on localized field-measured patient characteristics. The OLB is generic in that one "blank" may be customized to a variety of individual patient parameters that are measured in the field rather than manufactured in a laboratory setting.

The OLB is typically composed of a clear material (acrylic; silicon; poly(methyl methacrylate (PMMA); PMNA plastic, etc.) that has been infused with an ultraviolet (UV) absorbing compound rendering it amenable to customized spatial modification (CSM; of its refractive index via the use of pulsed laser radiation (PLR). The focus spot of the pulsed laser beam is moved inside the lens material to create a pattern of changes in the material, creating a three dimensional lens. Different patterns will provide different lens properties, for example a toric or aspheric lenses. The CSM of refractive index eliminates the need for remote laboratory fabrication of a customized intraocular lens (IOL) for the patient.

The OLB is retained within a secured lens container (SLC) providing for precise physical orientation of the OLB haptics and OLB lens structure with respect to the application of PLR to the OLB. The SLC contains a lens filler material (LFM) covering the OLB and is hermetically sealed after the OLB has been positioned within the SLC interior and prior to sterilization of the SLC+OLB combination.

Once customized, the sterilized SLC+OLB combination may be unsealed, the OLB retrieved and placed into the patient either as a customized IOL or a customized contact lens. The present invention is particularly, but not exclusively, useful as describing the procedure to create a very thin, multi-layered, micro-structured customized intraocular lens inside a PLM. The modifications can adjust diopter and/or add additional properties like toricity, multifocality and asphericity. The modifications can adjust for higher order aberrations. The instant invention is capable of creating new lenses which are thinner than existing products of a similar material.

BRIEF DESCRIPTION OF THE DRAWINGS

For a fuller understanding of the advantages provided by the invention, reference should be made to the following detailed description together with the accompanying drawings wherein:

FIG. 40 illustrates top right front perspective right section views of a preferred exemplary invention square SLC fixture embodiment;

FIG. 64 illustrates top right front perspective right section views of a preferred exemplary invention rectangular cartridge SLC fixture embodiment;

FIG. 6S illustrates a top view of a preferred exemplary invention cylindrical cartridge SLC fixture embodiment with generic ophthalmic lens blank (OLB) removed;

FIG. 89 illustrates a top view of a preferred exemplary invention cylindrical cartridge SLC retainer sealing cap (RSC) embodiment;

DESCRIPTION OF THE PRESENTLY PREFERRED EXEMPLARY EMBODIMENTS

Figure 1:
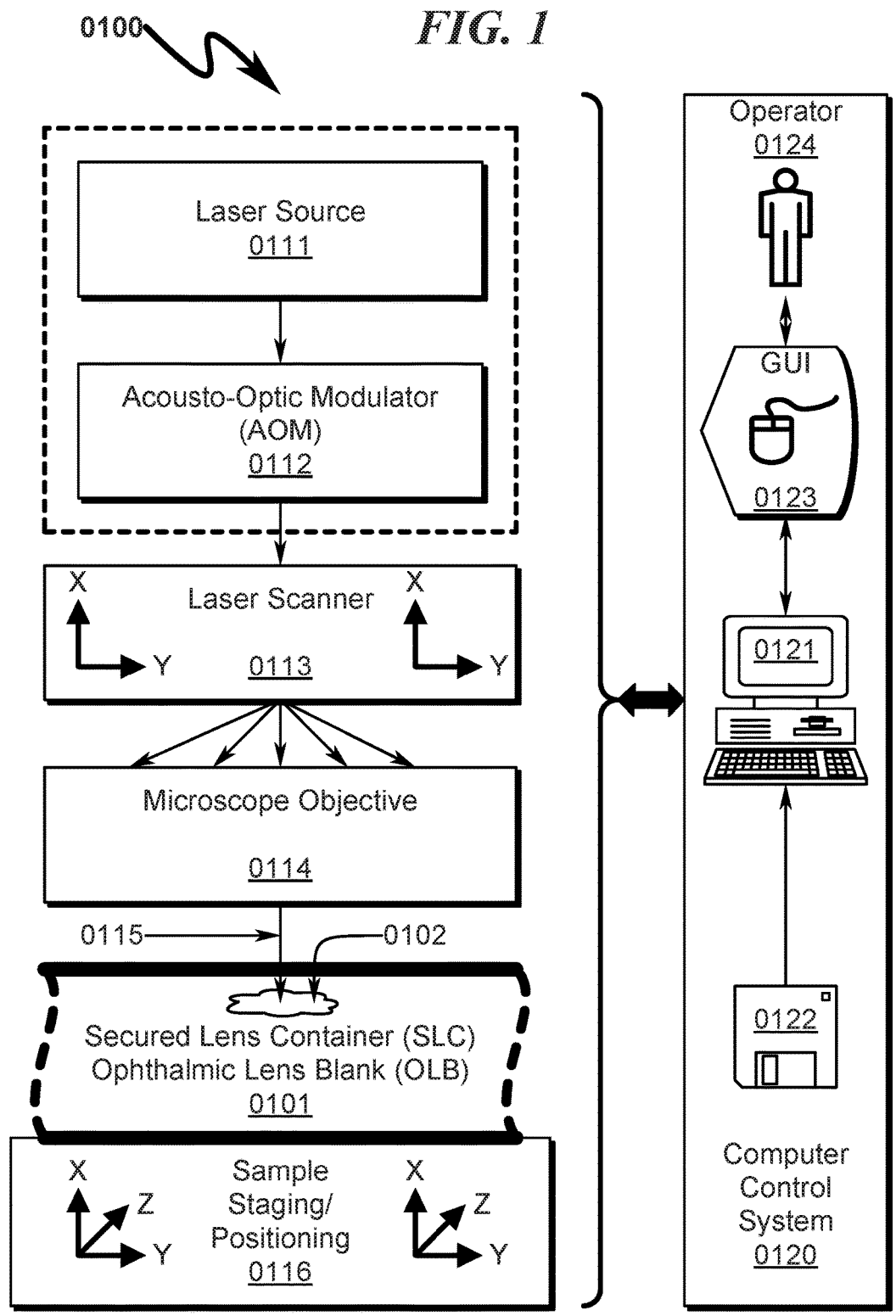
FIG. 1 illustrates an exemplary system block diagram depicting a preferred exemplary system embodiment of the present invention.

While this invention is susceptible of embodiment in many different forms, there is shown in the drawings and will herein be described in detailed preferred embodiment of the invention with the understanding that the present disclosure is to be considered as an exemplification of the principles of the invention and is not intended to limit the broad aspect of the invention to the embodiment illustrated.

The numerous innovative teachings of the present application will be described, with particular reference to the presently preferred embodiment, wherein these innovative teachings are advantageously applied to the particular problems of an OPHTHALMIC LENS CUSTOMIZATION SYSTEM AND METHOD. However, it should be understood that this embodiment is only one example of the many advantageous uses of the innovative teachings herein. In general, statements made in the specification of the present application do not necessarily limit any of the various claimed inventions. Moreover, some statements may apply to some inventive features but not to others.

Material (PLM) Limitive

The present invention may incorporate a wide range of materials, including the PLM but not limited to the PLM, within the scope of anticipated embodiments, many of which may be application specific, PLM may in many preferred embodiments incorporate the use of an ultraviolet (UV) (generally 10-400 nm wavelength) absorbing material to augment the absorption of pulsed laser energy by the PLM and thus affect a change in hydrophilicity of the PLM. PLM as used herein should not be constrained as limiting its use to materials that form optical lenses. Specifically, the term "polymeric material (PM)" may be used herein to denote applications of the invention system/method/product that are not necessarily limited to the production of optical lenses. Thus, "PM" may cover a broader application of the invention concepts than "PLM", although the materials may be identical. Therefore, the term "polymeric lens material (PLM)", "polymeric material (PM)" and their equivalents should be given the broadest possible meaning within this context.

UV Absorbers Not Limitive

The PLM may incorporate a number of chemicals which may enhance the UV absorption of the PLM and thus enhance the change in the PLM's hydrophilicity when irradiated with pulsed laser radiation. The present invention makes no limitation on the types and quantities of chemicals used to affect this behavior, and the recitation of these chemicals within this document is only exemplary of those anticipated.

Laser Ration Not Limitive

The present invention may incorporate a wide variety of laser radiation to affect changes in hydrophilicity within the PLM described herein to form a lens. Therefore, the term "laser radiation" and its equivalents should be given the broadest possible meaning within this context, and not limited to near infrared light laser radiation.

Laser Source Not Limitive

The present invention may incorporate a wide variety of laser radiation sources provide the required pulsed laser radiation used within the disclosed invention. Within this context, the term "laser source" may also incorporate an Acousto-Optic Modulator (AQM) (also called a Bragg cell) that uses the acousto-optic effect to diffract and shift the frequency of laser light generated using sound waves (usually at radio-frequency). Within this context, the "laser source" may be globally defined as comprising a laser radiation source and optionally an AOM, whether or not the AOM is physically incorporated into the laser radiation source hardware. Therefore, the term "laser source" and its equivalents should be given the broadest possible meaning within this context.

Acousto-Optic Modulator (AOM) Not Limitive

Various invention embodiments may make use of an Acousto-Optic Modulator (AOM) to act as a switch to enable/disable or moderate the quantity of laser radiation pulse stream as directed to the laser scanner within the context of the invention. Within this context the AOM may incorporate "grayscale" modulation wherein the switching function serves to switch a portion of the laser radiation pulse train to the laser scanner and therefore permit reductions in effective laser power as applied to the targeted PLM to which the hydrophilicity is to be modified. Thus, the utilization of "grayscale AOM" components to modulate laser radiation intensity is specifically anticipated within the scope of the invention.

The AOM as depicted in the present invention is used as a shutter and as variable attenuator and as such could therefore be replaced with another equivalent component which simulates the same functionality as described above.

Laser Scanner Not Limiting

The use of a laser scanner within the preferred invention embodiments described herein may incorporate many different varieties of scanner, including but not limited to flying spot scanners (generally vector-based modes) and raster scanners (generally raster-based modes). The scanner is used to distribute the laser pulse to the correct location within the objectives field size. The present invention makes no limitation on the type of laser scanner that may be used in this context.

Microscope Objective Not Limitive

References herein to a "microscope objective" may equivalentiy utilize a "microscope objective or other focusing device" to achieve these functions. Thus, the term "microscope objective" should be given its broadest possible interpretation within this application context.

Patient Not Limitive

The present invention may be applied to situations where a lens placed in a living creature is modified in situ to correct/modify the refractive properties of the lens without removal from the eye of the creature. Within this context, the term "patient" shall be broadly construed and should not be limited to application only on human beings.

Lens Form Not Limitive

The present invention may incorporate a wide variety of lenses formed to affect optical light bending and thus the construction of an overall lens formation. While exemplary embodiments of the present invention are described herein as being used to construct convex, biconvex, concave, biconcave, and piano lens structures, these structures are only exemplary of a plethora of lens forms that may be constructed with the present invention. Therefore, the term "lens formation" and its equivalents should be given the broadest possible meaning within this context.

Two-Dimensional Not Limitive

The present invention may incorporate the use of two-dimensional pattern structures within the PLM to form diffraction gratings and other thin planar structures which while technically three-dimensional, will be termed herein as two-dimensional. While no modification of the PLM hydrophilicity can occur strictly in a zero-thickness plane, the term two-dimensional will refer to the creation of structures which occur within the PLM that do not require Z-axis focus repositioning across the X-Y plane perpendicular to the optical axis. Thus, a two-dimensional modification of the PLM refractive index could occur along a non-planar boundary that comprises a singular Z-axis focal distance for the laser pulses. Therefore, the term "two-dimensional" and its equivalents should be given the broadest possible meaning within this context.

Three-Dimensional Not Limitive

The present invention may incorporate the use of three-dimensional pattern structures within the PLM to form complex optical structures. These three-dimensional pattern structures and their associated volumes may comprise multiple layers having interstitial PLM having a hydrophilicity that has not been modified by irradiation with laser pulses. Thus, a three-dimensional structure may incorporate non-modified areas having unmodified or slightly modified layer, or multiple layers comprising differing levels of hydrophilicity and resulting refractive index changes. Therefore, the term "three-dimensional" and its equivalents should be given the broadest possible meaning within this context.

Intraocular Lens Not Limitive

The present invention may be advantageously applied to the construction of dynamically adjustable optical lenses incorporating a wide range of materials. The mechanisms of incorporation of a wide variety of materials within the optical lens are not limited by the present invention. Therefore, the term "intraocular lens" and "optical lens (which would include contact lenses)" and its equivalent construction embodiments should be given the broadest possible meaning within this context.

General System Description

The present invention may be generally described as utilizing a laser system which consists of a femtosecond laser source, an AOM, a scanner, and an objective which delivers the laser pulses into the predetermined region. The laser source preferably has a pulse duration in the range of approximately 10 fs to 950 fs, a wavelength in the range of 400 to 1064 nm, and a repetition rate of between approximately 0.1 MHz to 100 MHz. The pulse energy is typically in the range of 0.01 microjoules to 15.0 microjoules. Focused laser radiation from the laser source typically has a spot size in the X-Y directions in the range of 1.0 micrometers to 20.0 micrometers, and a spot size in the Z-direction in the range of 0.05 micrometers to 200.0 micrometers.

Those who are skilled in the art understand that these laser parameters can be adjusted and rebalanced to be outside above-specified range but still be able to achieve the same level of energy delivered to the targeted regions of the lens material. For example, a tunable laser unit, such as Ti:Saphphire oscillator (Mai Tai By Newport, Irvine, Calif. or Spirit One from Spectra Physics (High Q)) can provide a variable or fixed wavelength in the range of approximately 520-1040 nm.

Generalized Lens Customization System (0100)

A preferred exemplary system embodiment of the present invention is generally illustrated in FIG. 1 (0100), wherein a material (0101) is irradiated (0115) to produce a refractive change within a selected region (0102) within the ophthalmic lens blank (OLB) (0101). This system (0100) generally incorporates a laser source (0111) that is configured to generate pulsed laser radiation which may be controlled/moderated/modulated/switched by an acousto-optic modulator (AOM) (0112) to produce a predetermined laser pulse train having specified energy and pulse timing characteristics. In some invention embodiments the laser source (0111) and AOH (0112) may be integrated into a single laser source module. The pulsed laser radiation generated by the laser source (0111)/AOM (0112) is then transmitted to a laser scanner (0113) that is configured to distribute the laser pulses in an X-Y plane across an input area of a microscope objective (0114). The microscope objective (0114) incorporates a numerical aperture configured to accept the distributed pulsed laser radiation and produce a focused laser radiation output (0115). This focuses laser radiation output (0115) is then transmitted by the microscope objective (0114) to a blank lens material (OLB) (0101) region (0102) in which the refractive index of the OLB (0101) is to be changed. The position, of the refractive-modified OLB region (0102) may be defined by the laser scanner (0113) as well as a sample staging/positioning system (0116) that mechanically positions the OLB (0101) to allow the focused laser pulses (0115) to be properly localized within the desired interior region (0102) of the OLB (0101).

This system, may optimally operate under control of a computer control system (0120) incorporating a computer (0121) executing software read from a computer readable medium (0122) and providing a graphical user interface (GUI) (0123) from which an operator (0124) may direct the overall operation of the refractive change (0102) within the OLB (0101).

System/Method Application Context Overview (0200)

Figure 2:
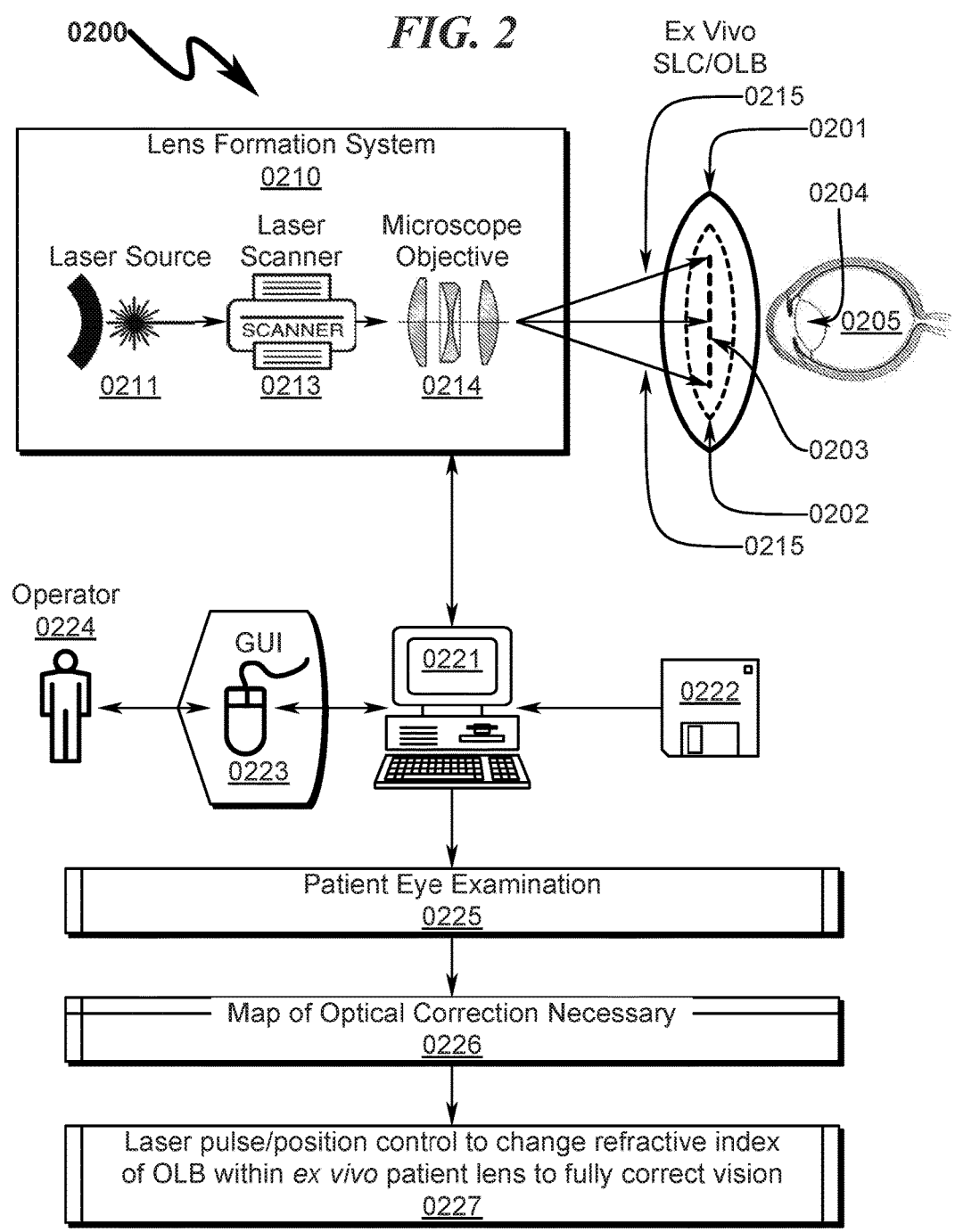
FIG. 2 illustrates an exemplary system block diagram of a preferred exemplary system embodiment of the present invention depicting a typical invention application setup context.

A typical application context for the present invention is generally illustrated in FIG. 2 (0200), wherein the present invention is embodied in a lens customization system (0210) used to configure patient lenses. This refractive index alteration system (0210) typically comprises a laser source (0211) that generates a pulsed laser output that is then distributed in an X-Y plane using a laser scanner (0213) and then focused using a microscope objective (0214) (or other focusing apparatus). This distributed and focused pulsed laser radiation (0215) is transmitted within a lens structure (0201) having some portion of which that is constructed of material (OLB) (0202). This OLB (0202) is irradiated in a two-dimensional or three-dimensional pattern (0203) within the OLB structure (0202) to modify the refractive index. This change in refractive index generated by the focused laser pulses (0214) causes the two-dimensional or three-dimensional pattern (0203) to form an optical lens function within the overall lens structure (0201).

In conjunction with this general system/method configuration, the lens structure (0201) may be incorporated (0204) within a human eye (0205) and the OLB (0202) modified ex vivo before the lens structure (0201) has been surgically implanted within the eye of a patient as generally illustrated in the diagram.

The described lens customization system (0210) is typically operated under control of a computer system (0221) executing instructions from a computer readable medium (0222). This computerized control (0221) optimally incorporates a graphical user interface (0223) permitting the system operator (0224) to interface with the overall system and direct its operation. With respect to the above-mentioned in situ lens formation application, the control software (0222) may incorporate software implementing methods to perform an automated patient eye examination to determine the non-idealities in the patient/s vision (0225), from which a map of optical corrections (0226) necessary to improve the patient's vision is generated, followed by automated laser pulse/position control procedures to change ex vivo the refractive index of OLB within the patient lens to fully correct the patient vision (0227).

System/Method Application Context Detail (0300)

Figure 3:
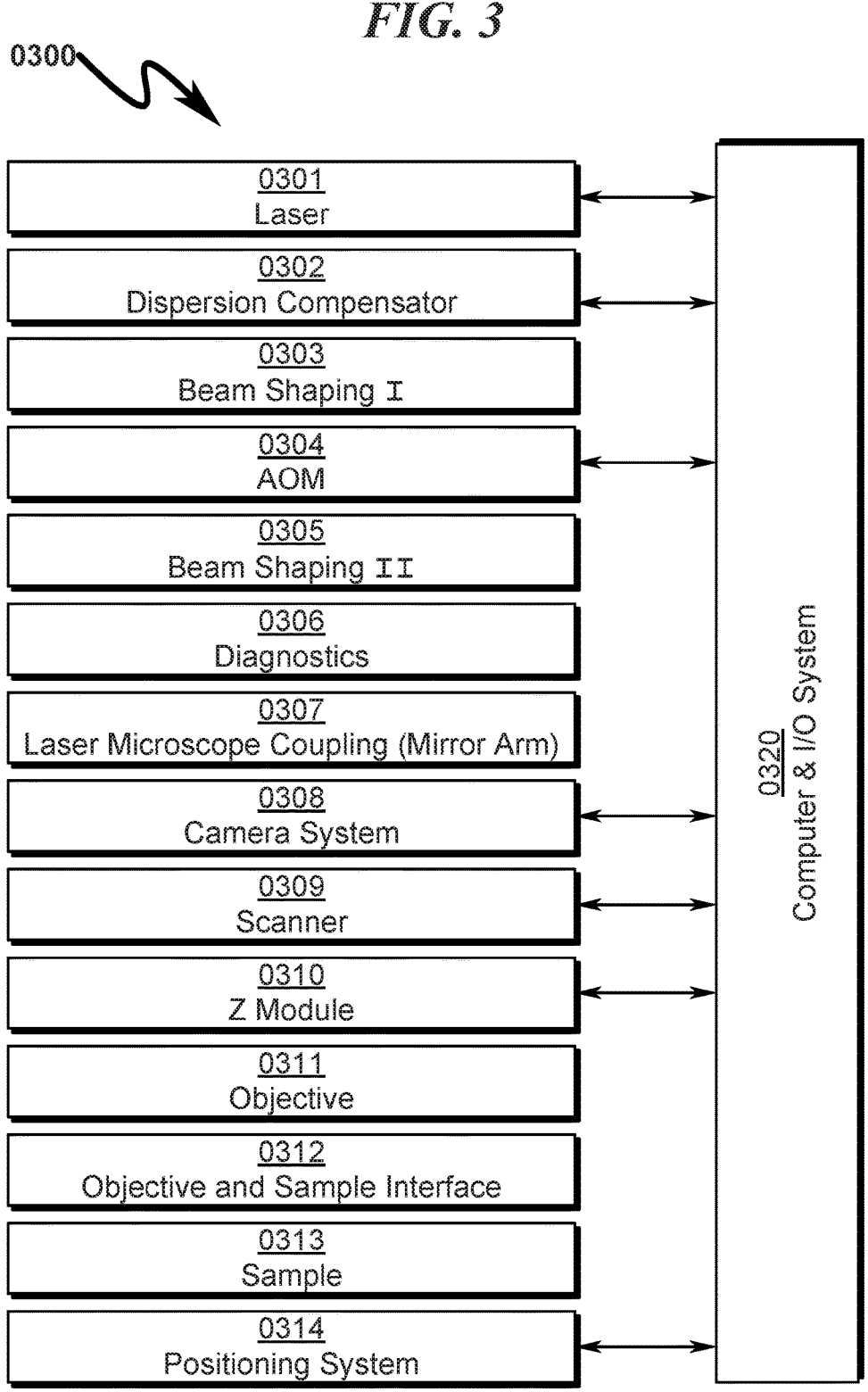
FIG. 3 illustrates a detail system block diagram illustrating system components that may be used to implement some preferred invention embodiments.

A more detailed system configuration of a preferred invention application context is provided in FIG. 3 (0300), wherein a computer system (0320) operating under control of software read from a computer readable media (0321, 0322) is used to control and supervise the overall lens fabrication process. Within this application context, the following components generally comprise the system:
  The laser source (0301) with a wavelength suitable to treat the desired material and an energy-per-pulse sufficient to change the refractive index of the target area provided by the used objective (0310).

The Dispersion Compensator (0302) is used to pre-compensate the beam to allow a pulse width around 100 fs. Without this feature the pulse width at the target would be larger because the pulse width gets longer when passing through an optical media like a lens. With a longer pulse with more heat would occur on the treatment area, making the process a little more imprecise and the treatment time a little longer. This feature therefore is optional but part of the RIS optimisation.

The Beam Shaping 1 (0303) unit can be used to modify the laser beam diameter to fit the AOM specifications. This also allows the exchange of the laser source without additional modifications after the beam shaping 1 unit.

The AOM (0304) is used to modulate the number of pulses and the energy per pulse which will be directed to the treatment area. Depending on the received signal (normally 0 to 5V) the energy will be distributed to the 0 or the $1^{st}$ order of the AOM. Those orders are two different beams, with an angle between them, coming out from the AOM. The $1^{st}$ order beam is normally the one going to the target area and the 0 order beam is stopped directly after the AOM. The receiving signal from the AOM driver is maximum (eg 5V) the maximum energy per pulse is in the $1^{st}$ order beam, when the driver signal is at the minimum the $1^{st}$ order beam will have 0% energy and everything will be delivered to the 0 order.

Beam Shaping 2, after the beam has passed through the AOM additional beam shaping is required to fit the system. For example the beam diameter has to be enlarged to fit the used objective (0310), to allow the use of the numerical aperture of the objective.

A Diagnostics (0305) system is used to measure the wavelength, energy per pulse and the pulse width of the laser beam. This feature in included to allow the safe and repeatable use of the system. If one of the variables is not performing as planned the system will shut down and Laser Microscope Coupling (Mirror Arm) (030S) is used to redirect the laser beam into the laser microscope head. Depending on the system setup and laser orientation it can contain between one and multiple mirrors to redirect the laser beam to the needed posit ion.

The Camera System (0307) is used to position the sample towards the microscope objective in the X-Y directions. Additionally the camera can be used for tracking purposes. The correct X location may be found effectively with an OCT camera depending on the materials curvature.

The Scanner (0308) is used to distribute the laser spot on the XY plane. Different scanners can be used for this purpose. Depending on the scanner type the untreated area would still be covered but with no laser energy per pulse or only the treated areas would be covered. For this purpose the software controlling will also control the AOM because the scanner software will position the spot and the AOM will contribute the energy per pulse for that spot.

The Z Module (0309) can be used to allow an extra focusing element in the system, this for example can be used for tracking purposes for a plane in a different Z location than the shaping plane. It also could be used to change the Z location during the shaping process.

The Objective (0310) focuses the beam on the sample and determines the spot size. With a larger spot size a larger energy per pulse is required it therefore has to be fitted to the laser source and the required precision of the process. Additionally it provides the field size of the shaping process, if the field size of the objective is smaller than the required lens, this requires additional hardware for the lens shaping, The Objective and Sample Interface (0311) is depending on the application. For the lens manufacturing the space between the sample and the objective is filled with water to reduce scattering and allow an additional cooling element. For other applications different contact method with other mediums like eye gel could be used.

The Sample (0312) can be comprised of different optical mediums and could for example be a hydrophobic polymer which is placed in front of the objective. Depending on the application that sample will be directly after the Objective and Sample interface or deeper inside an additional medium combination like an eyeball.

The Positioning System (0313) can be used to position the blocks comprising of the objective field sizes towards each other to allow the shaping of a larger structure. It can also be used to move the sample in the Z direction.

One skilled in the art will recognize that a particular invention embodiment may include any combination of the above components and may in some circumstances omit one or more of the above components in the overall system implementation.

Lens Shaping/Formulation Method (0400)

The present invention also teaches a lens shaping/formation method wherein a lens of arbitrary complexity may be formed within OLB. The lens shaping consists of different parts. First the lens diopter and curvature have to be calculated depending on the selected material. The laser wavelength afterward is also adjusted towards this material. The AOM functions as the shutter and also as a variable power attenuator in the setup allowing (in combination with the scanner) the lens structure to be precisely shaped inside the polymer. The AOM is controlled by the input images of the calculated lens information, providing the laser power information for each area (micrometer) of irradiated area. The scanner afterward distributes the power to the correct location and the microscope objective focuses the pulsed laser beam to the desired focus spot inside the polymer. The OLB sample is kept in a sample holder after the microscope objective and is optionally positioned on a stage system (mechanized X/Y/Z positioning system) to allow the shaping of a larger lens structure. The stage system could also be replaced with a mirrored laser arm which ends with the microscope objective. The mirrored arm in this case would not only replace the stage system but the whole camera and scanner board.

Figure 4:
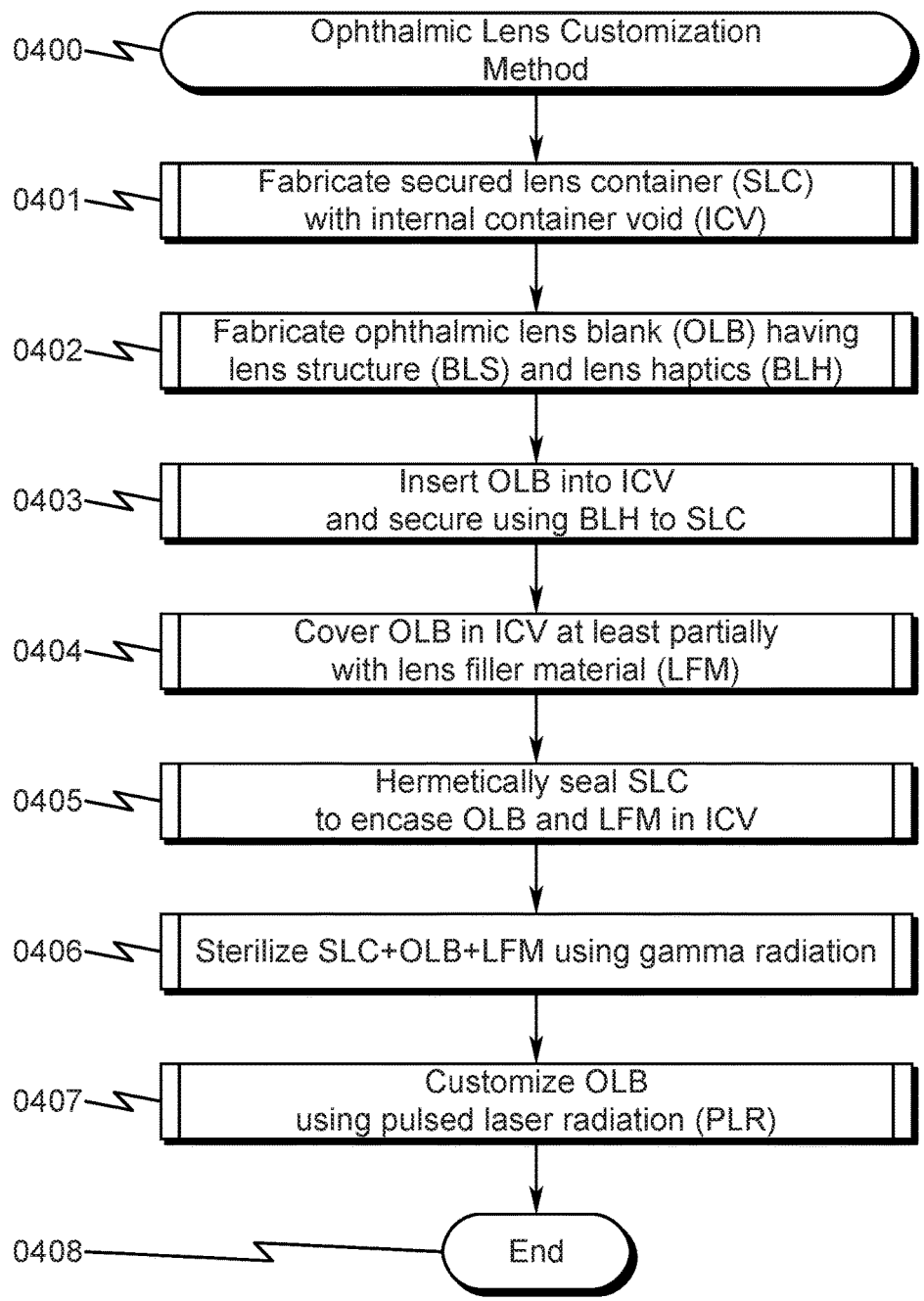
FIG. 4 illustrates an exemplary OLB ophthalmic lens customization method flowchart used in some preferred embodiments of the present invention.

The present invention method may incorporate an embodiment of this lens shaping/formation method as depicted in FIG. 4 (0400) comprising:
(1) Fabricate secured lens container (SLC) with internal container void (ICV) (0401);
(2) Fabricate ophthalmic lens blank (OLB) having lens structure (BLS) and lens haptics (BLH) (0402);
(3) Insert OLB into ICV and secure using BLH to SLC (0403);

(4) Cover OLB in ICV at least partially with lens filler material (LFM) (0404);
(5) Hermetically seal SLC to encase OLB and LFM in ICV (0405);
(6) Sterilize SLC+OLB+LFM using gamma radiation (0406); and
(7) Customize OLB using pulsed laser radiation (PLR) (0407).

This general method may be modified heavily depending on a number of factors, with rearrangement and/or addition/deletion of steps anticipated by the scope of the present invention. Integration of this and other preferred exemplary embodiment methods in conjunction with a variety of preferred exemplary embodiment systems described herein is anticipated by the overall scope of the present invention. This method may be applied to one or more layers within the OLB to achieve formed lens structures of arbitrary complexity.

OLB Customization Method (0500)-(0700)

Figure 5:
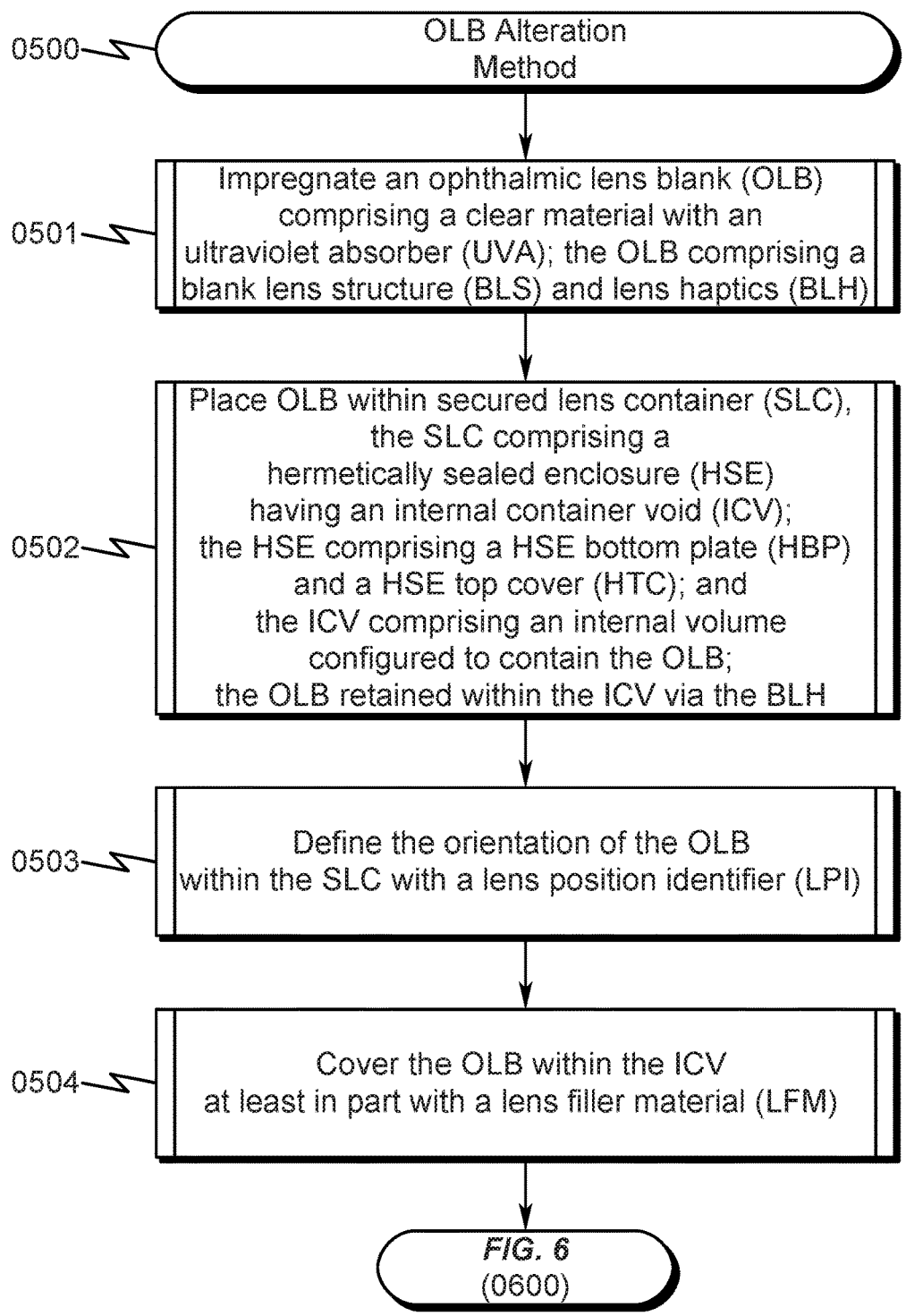
FIG. 5 illustrates an exemplary OLB alternation method flowchart used in some preferred embodiments of the present invention (part 1/3)
Figure 6:
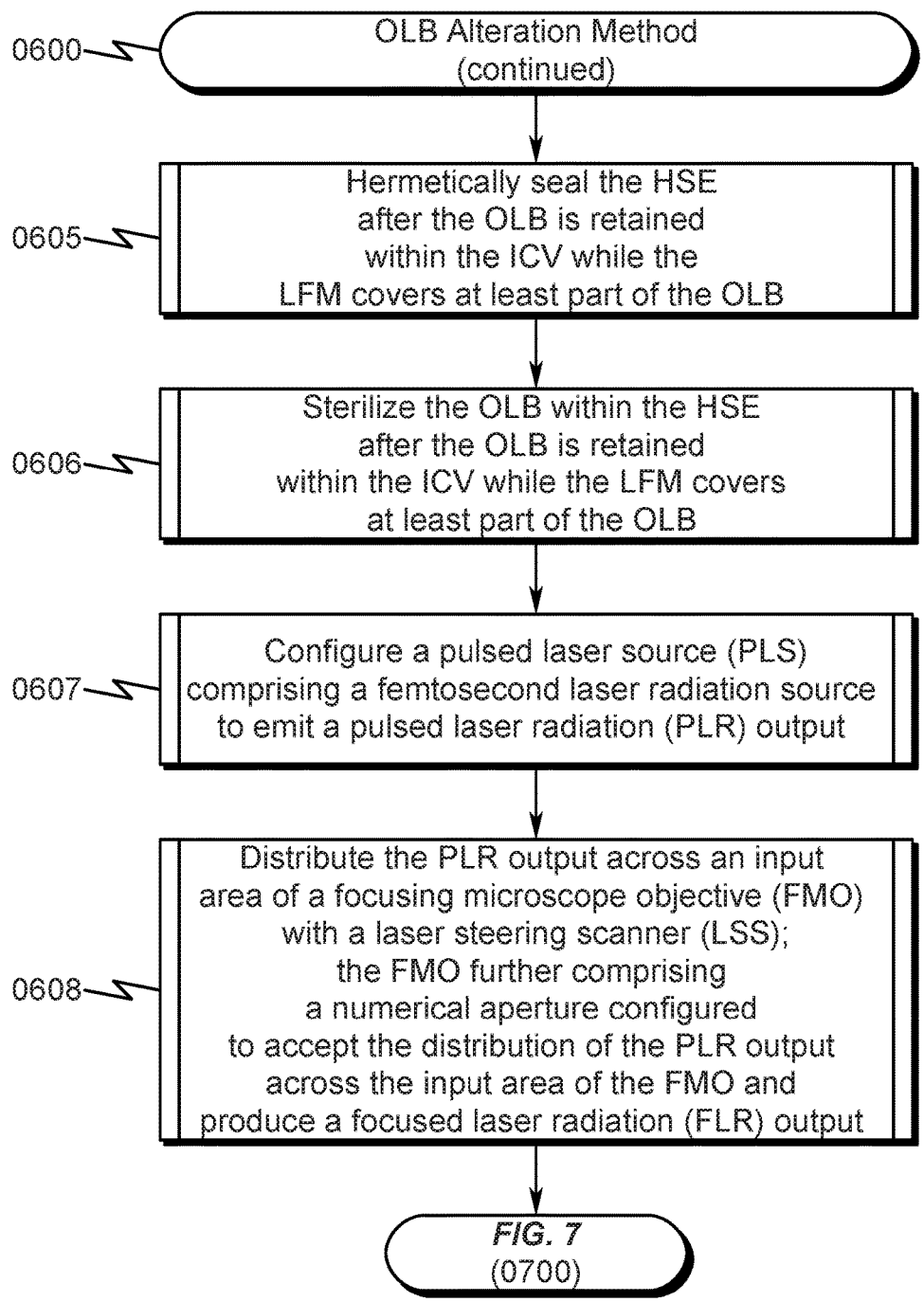
FIG. 6 illustrates an exemplary OLB alternation method flowchart used in some preferred embodiments of the present invention (part 2/3)
Figure 7:
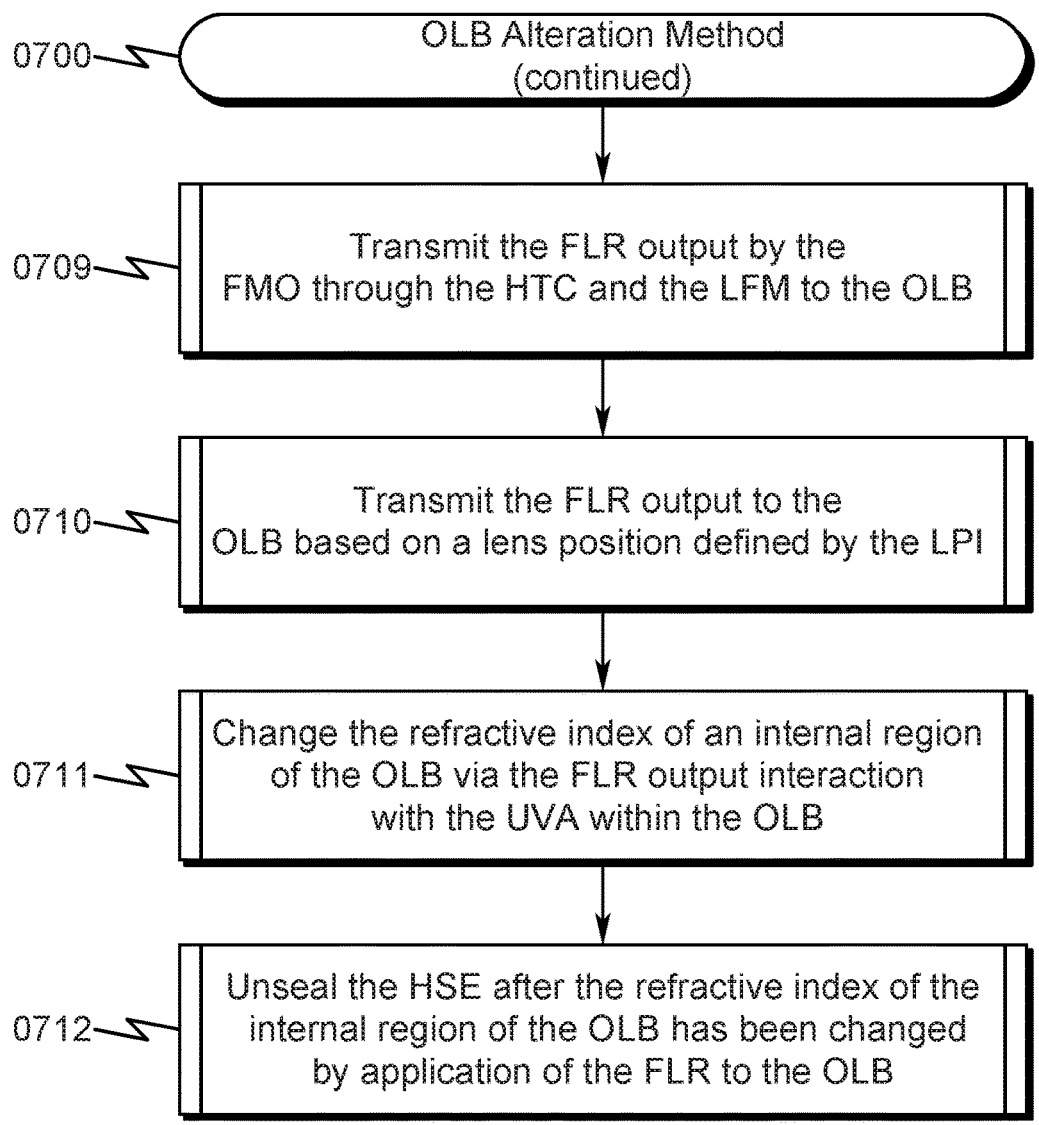
FIG. 7 illustrates an exemplary OLB alternation method flowchart used in some preferred embodiments of the present invention (part 3/3)

The present invention method anticipates a wide variety of variations in the basic theme of implementation, but can be generalized as depicted in FIG. 5 (0500)-FIG. 7 (0700) as a lens customization method comprising:
(1) impregnating an ophthalmic lens blank (OLB) comprising a clear material with an ultraviolet absorber (OVA); the OLB comprising a blank lens structure (BLS) and lens hapties (BLB) (0501);
(2) placing the OLB within a secured lens container (SLC), the SLC comprising a hermetically sealed enclosure (HSE) having an internal container void (ICV); the HSE comprising a HSE bottom plate (HBP) and a HSE top cover (HTC); and the ICV comprising an internal volume configured to contain the OLB; the OLB retained within the ICV via the BLH (0502);
(3) defining the orientation of the OLB within the SLC with a lens position identifier (LPI) (0503);
(4) covering the OLB within the ICV at least in part with a lens filler material (LFM) (0504);
(5) hermetically sealing the HSE after the OLE is retained within the ICV while the LFM covers at least part of the OLB (0605);
(6) sterilizing the OLB within the HSE after the OLB is retained within the ICV while the LFM covers at least part of the OLB (0606);
(7) configuring a pulsed laser source (PLS) comprising a femtosecond laser radiation source to emit a pulsed laser radiation (PLR) output (0607);
(8) distributing the PLR output across an input area of a focusing microscope objective (FMO) with a laser steering scanner (LSS); the FMO further comprising a numerical aperture configured to accept the distribution of the PLR output across the input area of the FMO and produce a focused laser radiation (FLR) output (0603);
(9) transmitting the FLR output by the FMG through the HTC and the LFF to the OLB (0709);
(10) transmitting the FLR output to the OLB based on a lens position defined by the LPI (0710);
(11) changing the refractive index of an internal region of the OLB via the FLR output interaction with the UVA within the OLB (0711); and
(12) unsealing the MSB after the refractive index of the internal region of the OLB has been changed by application of the FLR to the OLB (0712).

This general method may be modified heavily depending on a number of factors, with rearrangement and/or addition/deletion of steps anticipated by the scope of the present invention. Integration of this and other preferred exemplary embodiment methods in conjunction with a variety of preferred exemplary embodiment systems described herein is anticipated by the overall scope of the present invention. This and other methods described herein are optimally executed under control of a computer system reading instructions from a computer readable media as described elsewhere herein.

Lens Calculation Method (0800)

The present invention also teaches a lens calculation method wherein lens parameters are used to determine the internal OLB lens structure that is customized for a particular patient and their unique optical requirements. This method generally involves the following steps:

Calculating the the three dimensional structure of the lens to be formed;
Determining the required lens depth;
Calculating the number of zones which must be processed via the laser;
Determining the zone radius for each zone to be processed;
Create phase wrapping lens data files for the laser; and
Loading the data files into the RIS mapping system.

These steps will now be discussed in more detail.

Before the lens parameters for a custom intraocular lens (IOL) can be calculated the patient needs to be examined, the different existing aberrations can be measured and the needed spherical and cylindrical diopter (Dpt) changes can be evaluated as well as the distribution of light and diopter for multifocality. The material (n) for the shaping process has to be known to calculate the lens dimensions (C).

$$C = \frac{Dpt}{(n' - n)} \quad (1)$$

Where n is the refractive index of the original IOL material and rd is the refractive index after the RIS shaping, and therefore the refractive index of the new lens.

$$C = \frac{1}{r} \quad (2)$$

The curvature is related to lens radius (r) and the radius can be calculated with the lens diameter $2w_{Lens}$ and the lens depth $h_{Lens}$.

$$r = \frac{h_{Lens}^2 + w_{Lens}^2}{2h_{Lens}} \quad (3)$$

Afterward the Phase Wrapping Lens Information is calculated for the given information and the output images are created. All required information for the Phase Wrapping Lens already exists in the information of the original lens and its curvature. The Phase Wrapping depth of the lens is determined by the refractive index change amount. Afterward the radius of each zone and for the curvature information of each zone can be easily calculated. Depending on the shaping technique the lens diopter can be larger than the objective field size, in this case a stage system (as described above) is used to align the different areas for the lens shaping. To allow this technique the input images are chopped into their images sizes to represent the block system.

Figure 8:
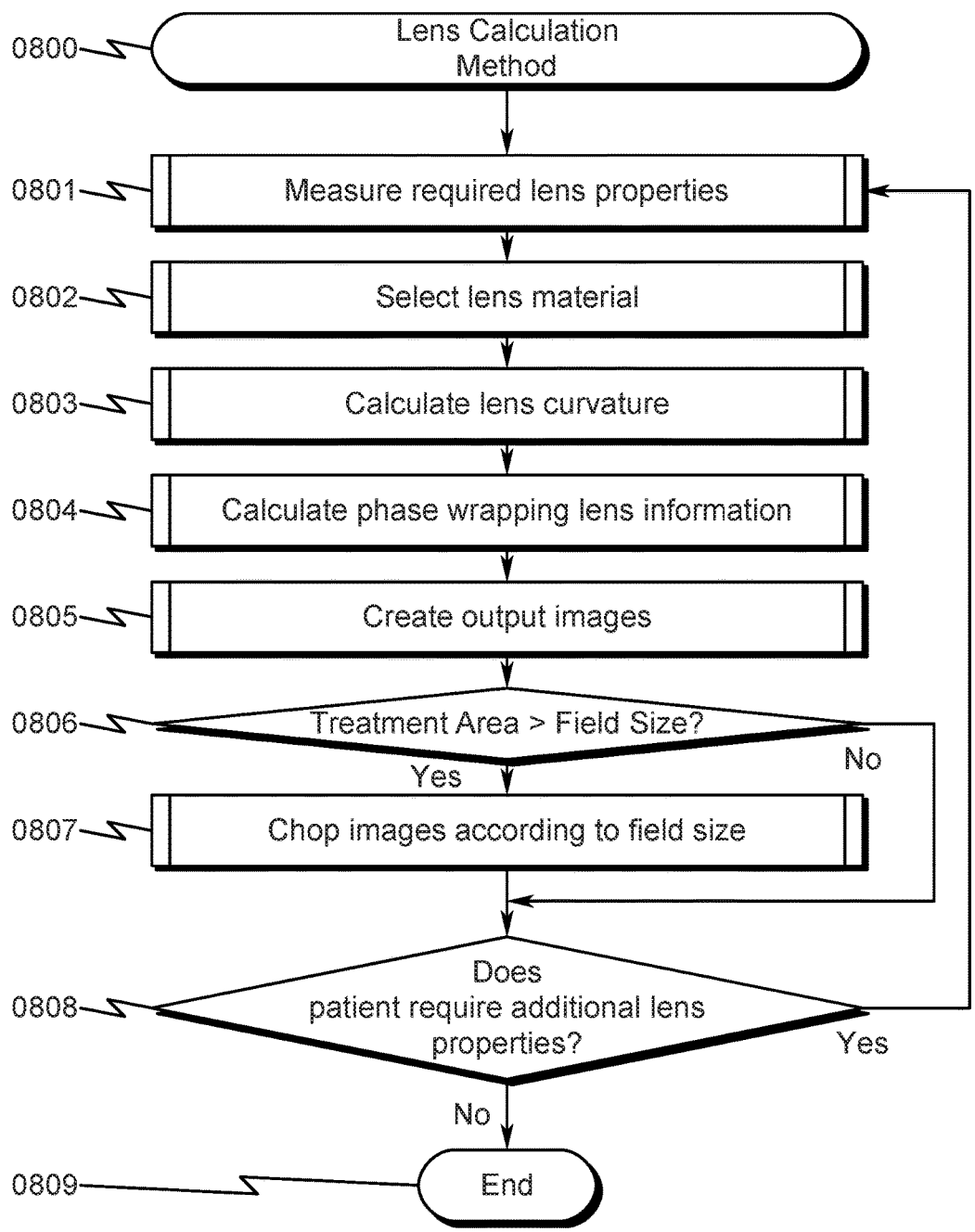
FIG. 8 illustrates an exemplary lens calculation method flowchart used in some preferred embodiments of the present invention.

The lens calculation method described above and generally depicted in FIG. 4 (0400, 0401) may be embodied in many forms, but several preferred embodiments of the present invention method may implement this method as depicted in FIG. 8 (0800) using the following steps:

(1) measuring or determining required lens properties for desired optical performance (0801);
(2) selecting a lens material appropriate for lens fabrication (0802);
(3) calculating the desired lens dimensions, including curvature (0803);
(4) calculating phase wrapping lens information necessary to form the lens (0804);
(5) creating output images that correspond to the desired phase wrapping lens characteristics (0805);
(6) determining if the lens treatment area is larger than the objective field size, and if not, proceeding to step (8) (0806);
(7) chopping the output images into segments that fit within the field size (0807);
(8) determining if the patient (or lens formation) requires additional lens properties, and if so, proceeding to step (1) (0808); and
(9) terminating the lens calculation method (0809).

This general method may be modified heavily depending on a number of factors, with rearrangement and/or addition/deletion of steps anticipated by the scope of the present invention. Integration of this and other preferred exemplary embodiment methods in conjunction with a variety of preferred exemplary embodiment systems described herein is anticipated by the overall scope of the present invention.

This method may be applied to the formation of lenses that are retained/held by a SLC and manipulated spatially by a staging apparatus or positioning table.

Typical OLB IOL Lens Structures

Figure 9:
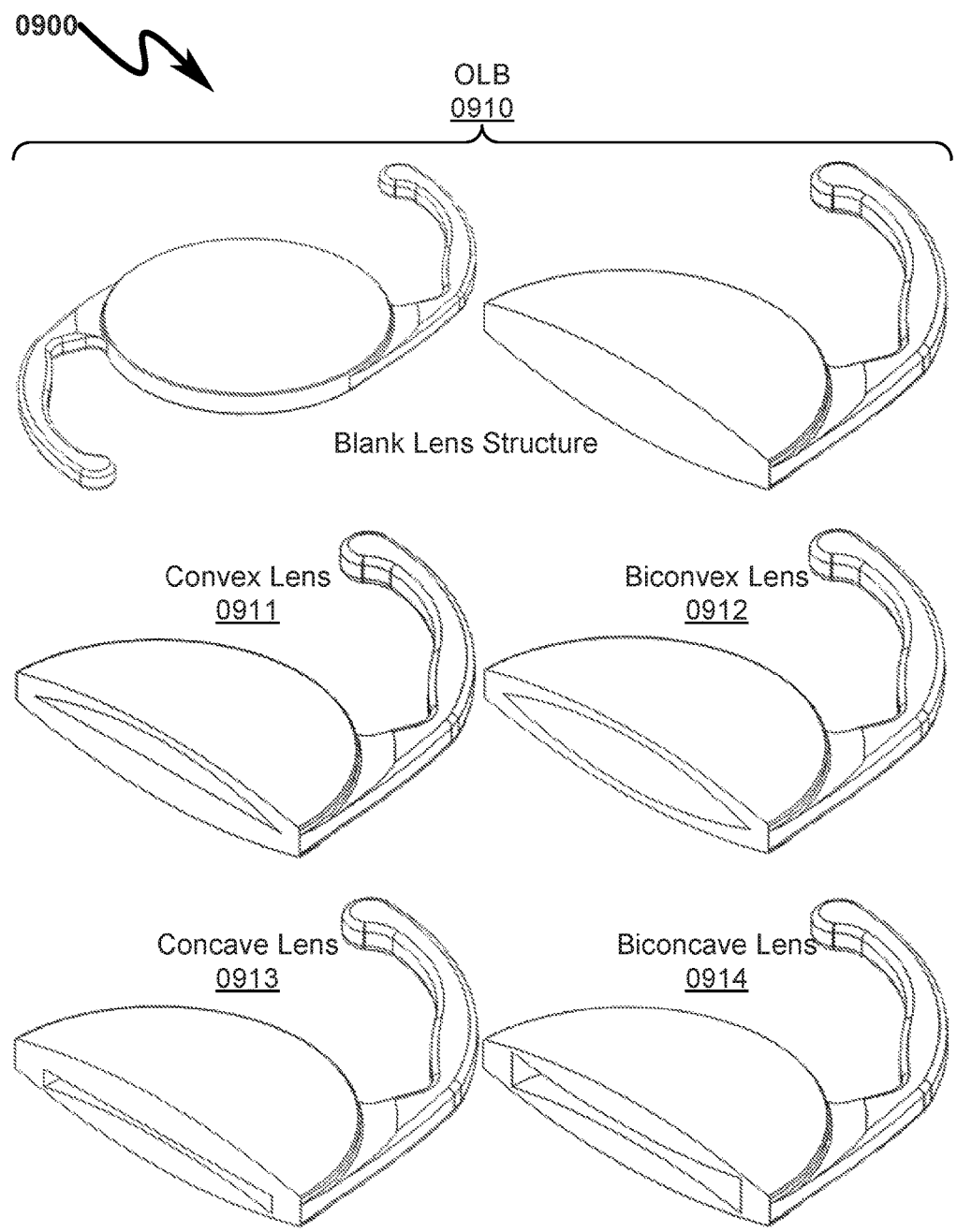
FIG. 9 illustrates an exemplary OLB IOL structure prior and customization and subsequent convex/biconvex/concave/biconcave lens structures generated post-customization as taught by the present invention.

FIG. 9 (0900) illustrates a typical OLB IOL structure prior to customization (0910) and subsequent customized internal convex lens (0911), biconvex lens (0912), concave lens (0913), and biconcave lens (0914) internal structures generated post-customization as taught by the present invention. The various internal structures depicted within the OLB IOL structure may be combined in some application contexts. Furthermore, it should be noted that the symmetry depicted in these examples may not be present in some application contexts, as custom lens formations including phase wrapping lens structures as depicted in U.S. Pat. No. 9,023,257 may be formed using the teachings of the present invention.

Figure 10:
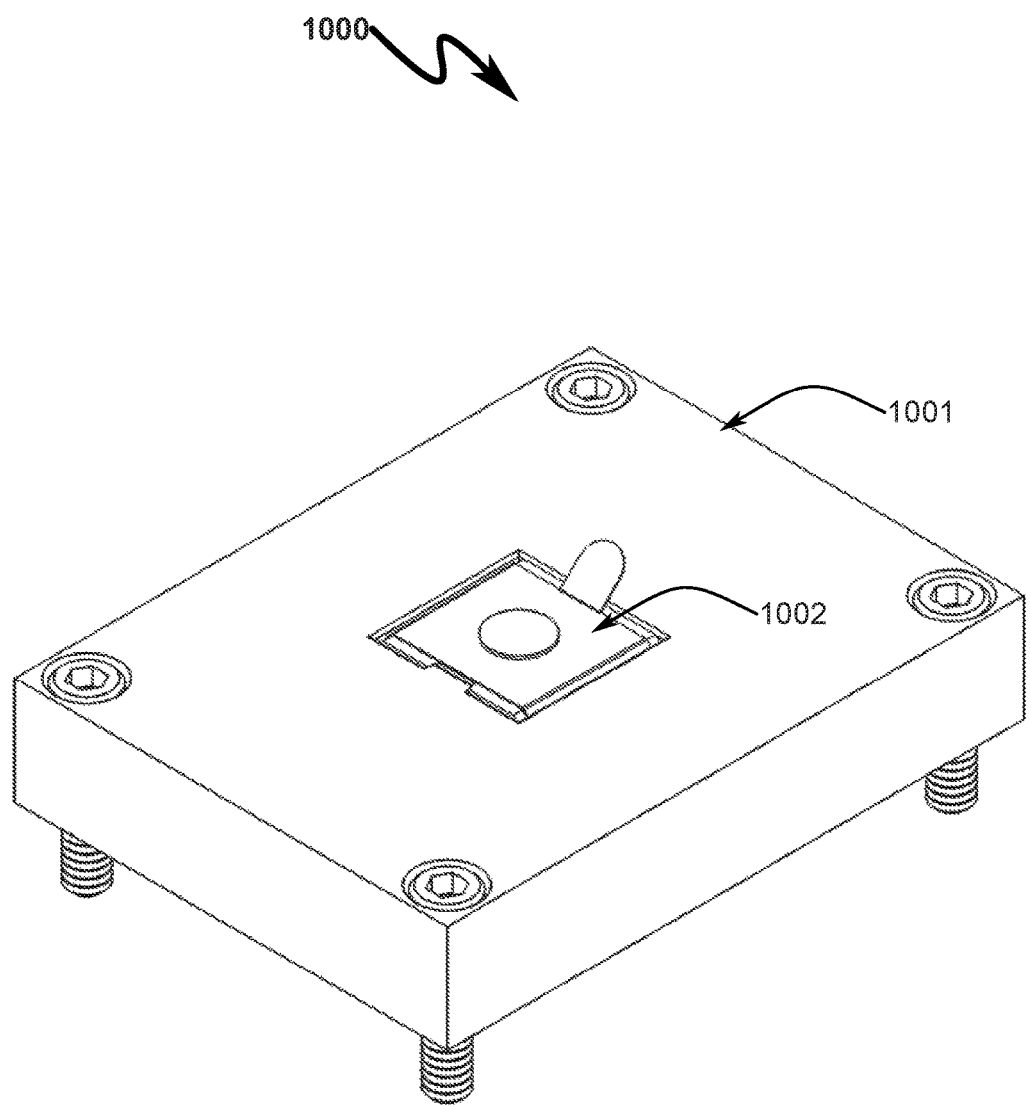
FIG. 10 illustrates a top right front perspective view of a preferred exemplary invention square SLC fixture embodiment with generic ophthalmic lens blank (OLB) installed on a base mounting fixture.
Figure 11:
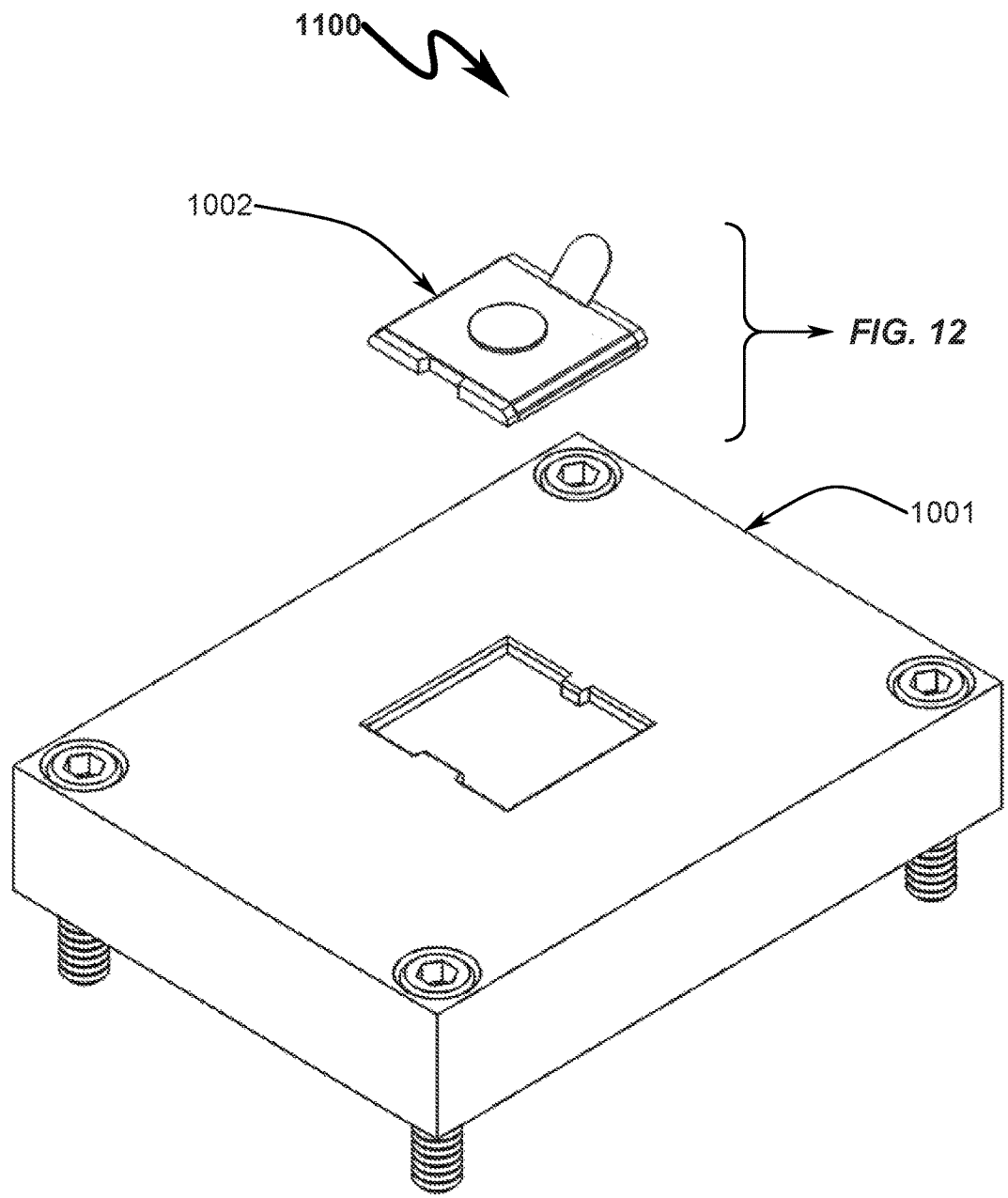
FIG. 11 illustrates a top right front perspective assembly view of a preferred exemplary invention square SLC fixture embodiment with generic ophthalmic lens blank (OLB) installed on a base mounting fixture.
Figure 16:
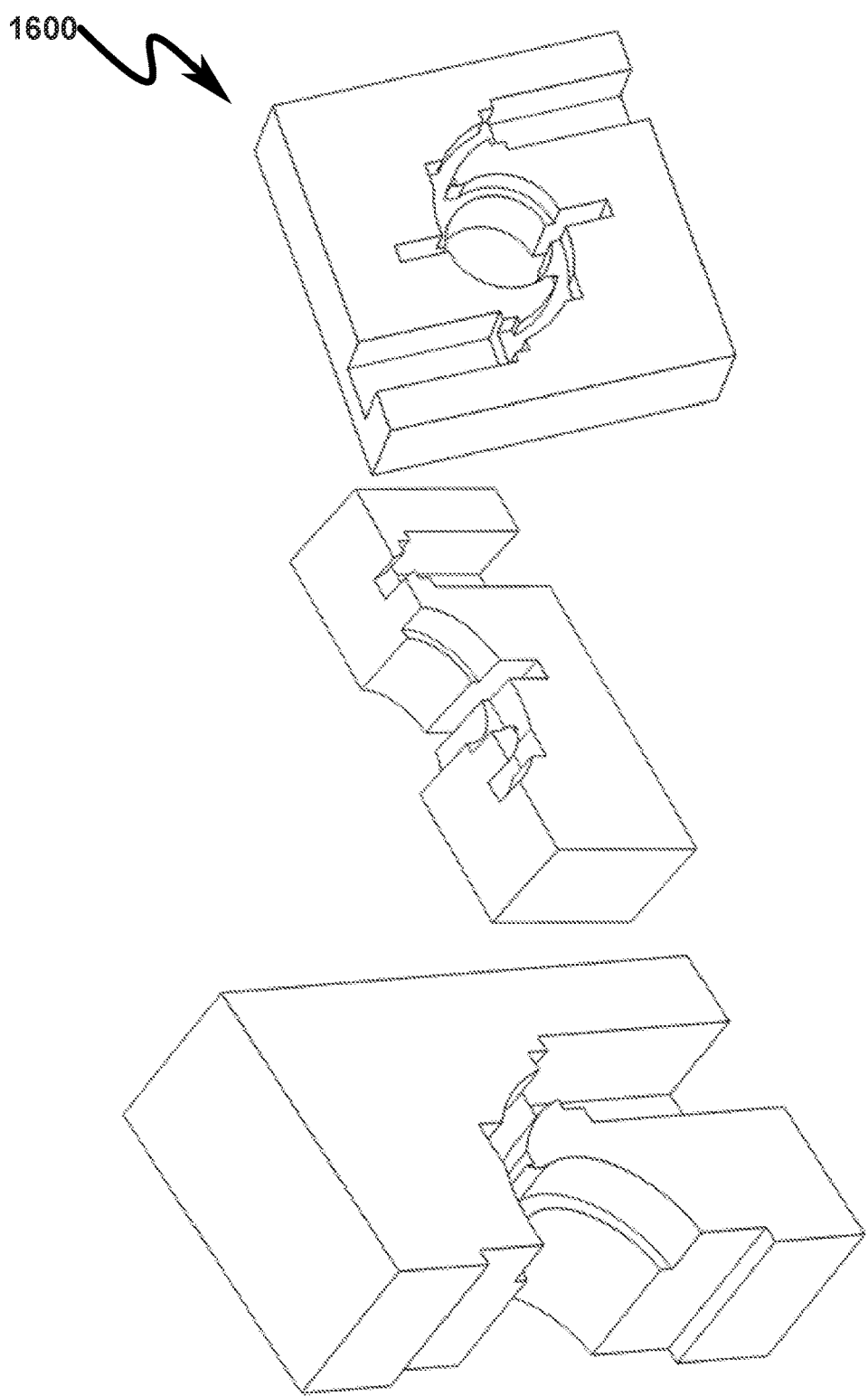
FIG. 16 illustrates top right front perspective, top right front perspective front section, and top right front perspective right section detail views of an alternate SLC fixture for OLB lenses to support lens customization as detailed herein.

An overview of the SLC and corresponding OLB structures typically utilized with the present invention are detailed in FIG. 10 (1000)-FIG. 16 (1600).

Figure 12:
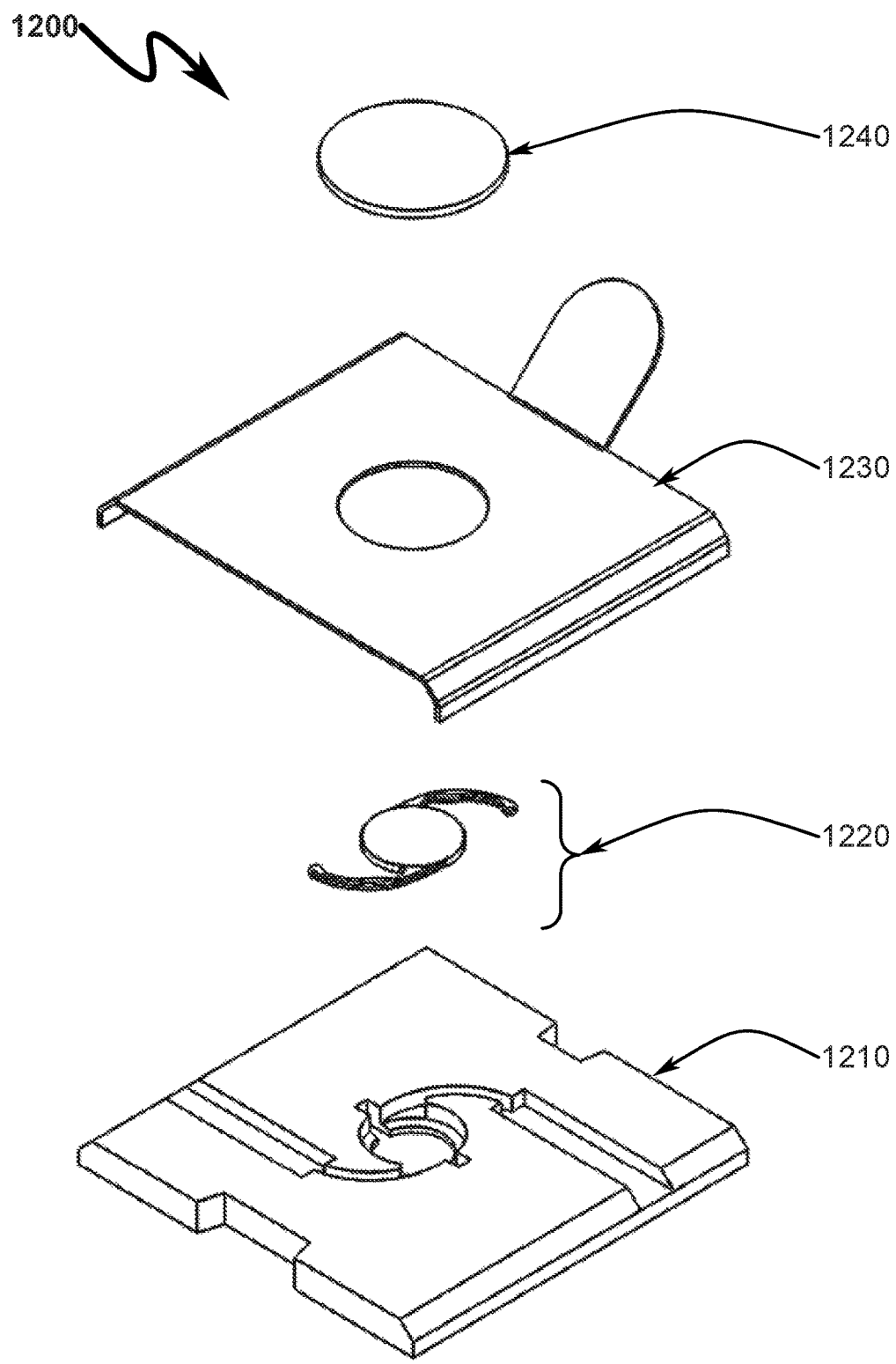
FIG. 12 illustrates a top right front perspective assembly detail view of a preferred exemplary invention square SLC embodiment with generic ophthalmic lens blank (OLB) installed.
Figure 13:
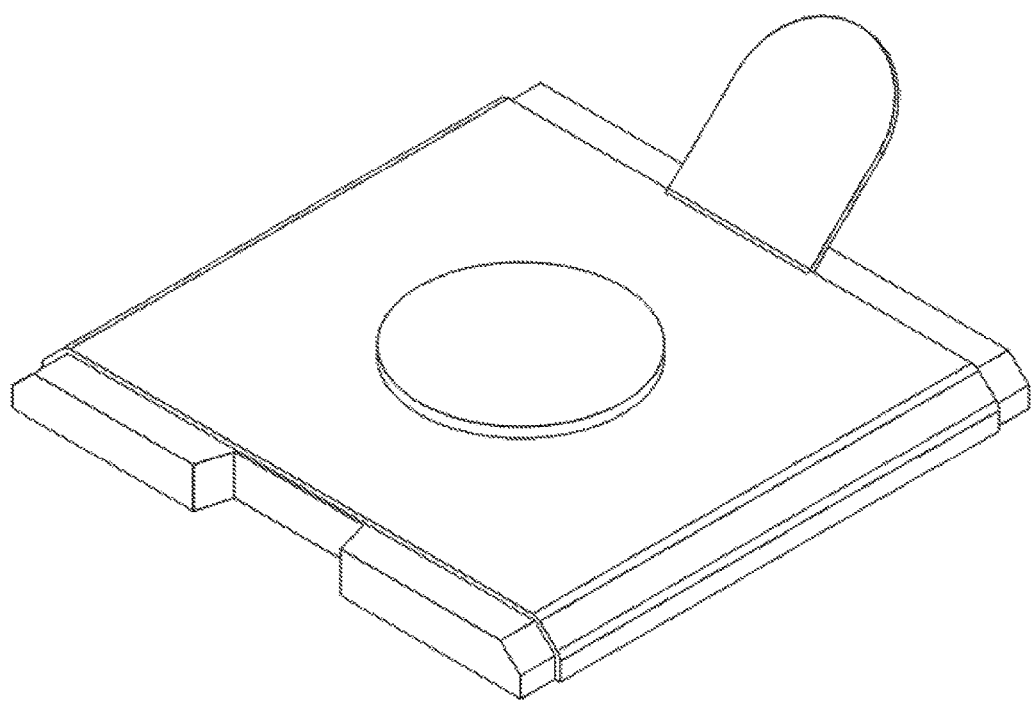
FIG. 13 illustrates a top right front perspective detail view of a preferred exemplary invention square SLC embodiment with generic ophthalmic lens blank (OLB) installed.
Figure 14:
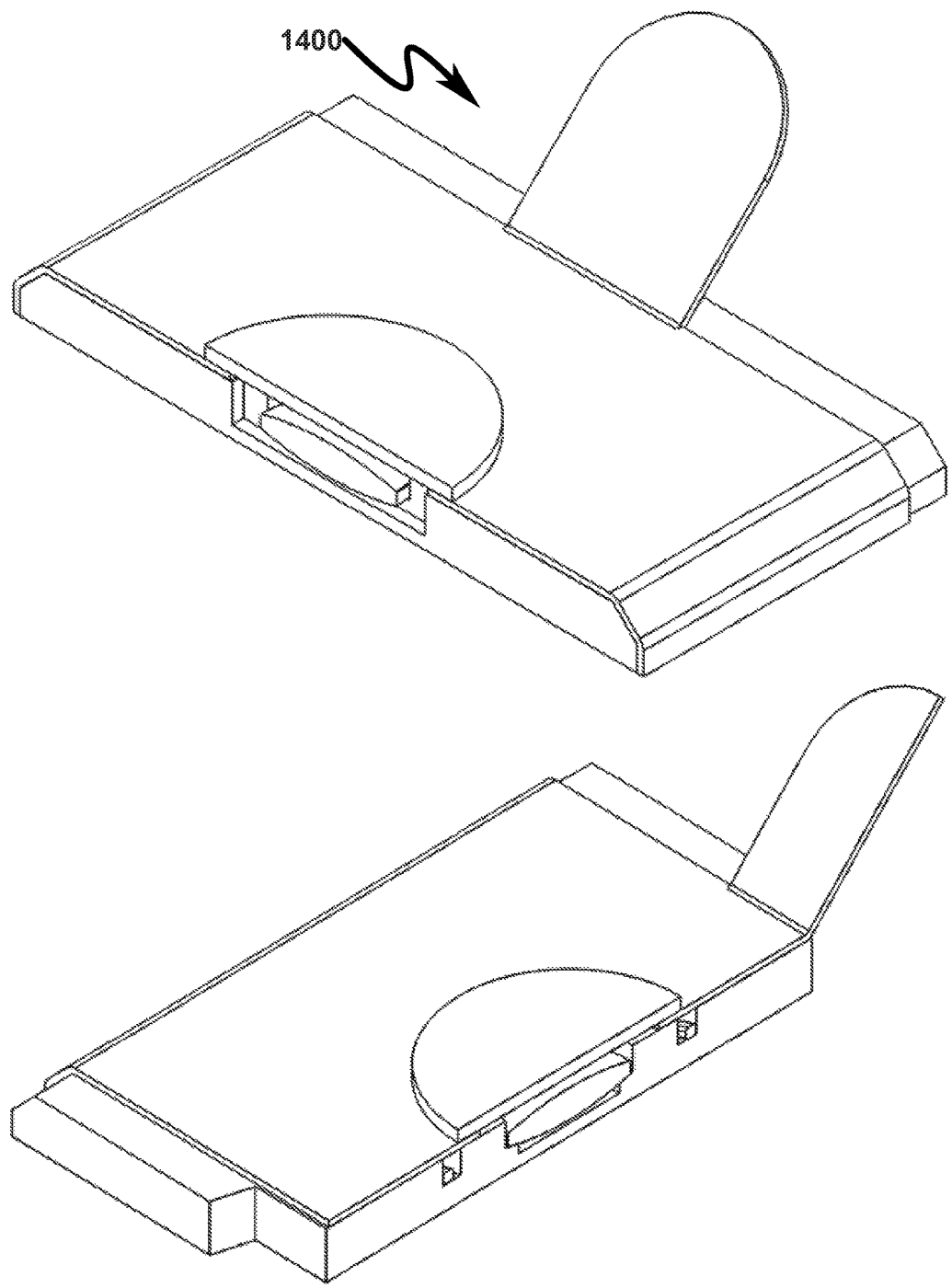
FIG. 14 illustrates top right front perspective detail front and right section views of a preferred exemplary invention square SLC embodiment with generic ophthalmic lens blank (OLB), cover seal, and laser access window installed.
Figure 15:
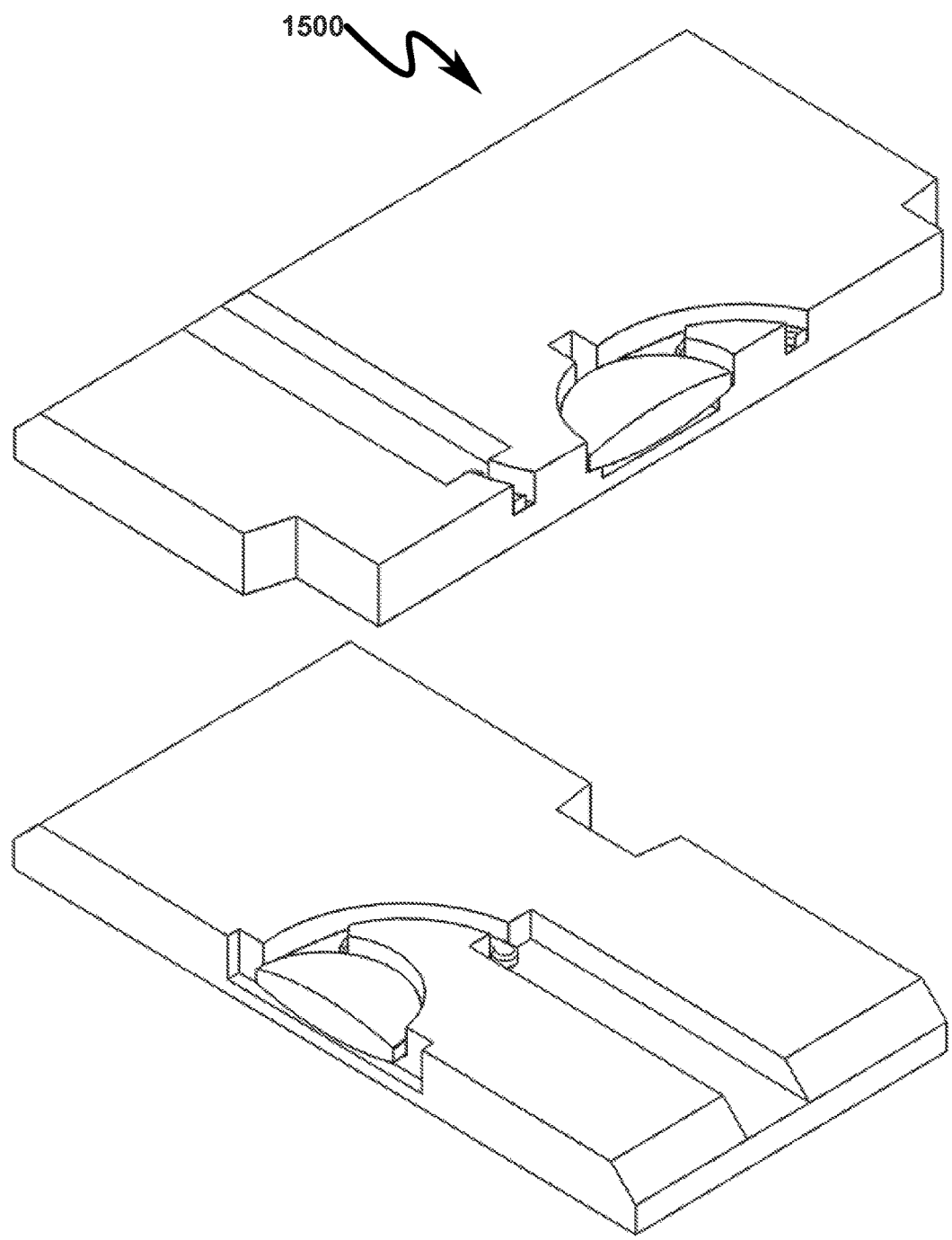
FIG. 15 illustrates top right front perspective detail front and right section views of a preferred exemplary invention square SLC embodiment with generic ophthalmic lens blank (OLB) installed and cover seal/laser access window removed.

An exemplary square SLC embodiment is generally depicted in FIG. 10 (1000)-FIG. 16 (1600). As depicted in FIG. 10 (1000) it can be seen, that a baseplate fixture (1001, 1101) securely retains the square SLC (1002, 1102) to permit laser radiation to be focused on the OLB contained within the SLC (1002, 1102). The assembly view in FIG. 12 (1200) details the SLC (1210), OLB (1220), hermetic seal (1230), and laser access window (1240). FIG. 13 (1300)-FIG. 15 (1500) depict the SLC in various stages of disassembly. It should be noted in this particular embodiment the hermetic seal (1230) extends around the edges of the SLC holder and allows the lens cavity to be filled with fluid through the laser access window (1240) which is installed after fluid filling of the lens cavity. The laser access window (1240) is selected to be transparent to laser radiation and have a low refractive index in the range of 1.05 to 1.65. This particular embodiment provides for direct horizontal access to the haptics via the side of the fixture which allows easy removal of the OLB once customization is complete and the hermetic seal (1230) has been removed.

FIG. 16 (1600) depicts various views of an alternate SLC holder in which the lens cavity and other structures extend to the entire depth of the fixture. In this configuration there would exist a containment structure to hold the SLC holder depicted so as to allow fluid filling of the container and immersion of the OLB during the customization process.

Exemplary Square SLC Embodiment (1700)-(4000)

Figure 17:
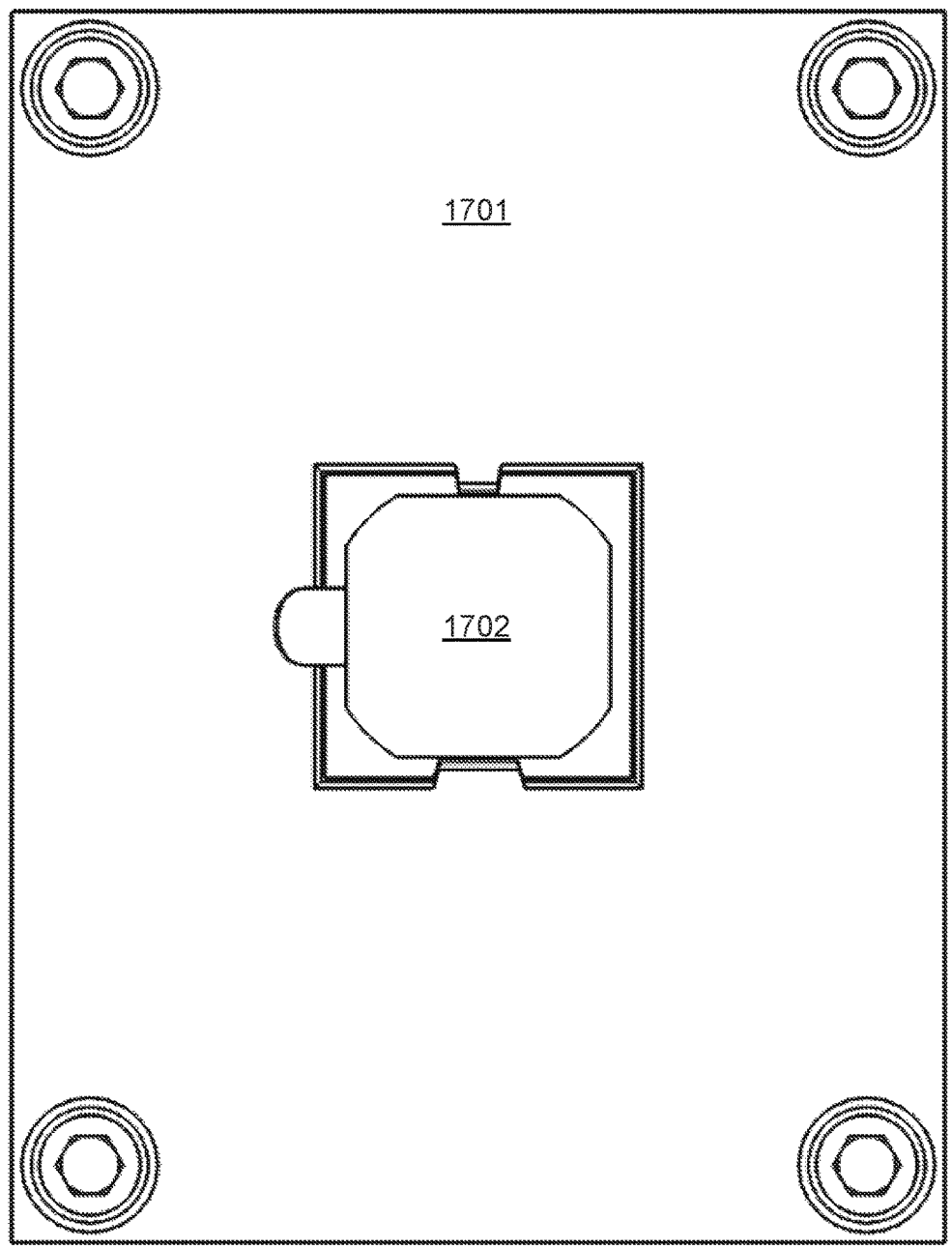
FIG. 17 illustrates a top view of a preferred exemplary invention square SLC fixture embodiment with generic ophthalmic lens blank (OLB) installed.
Figure 18:
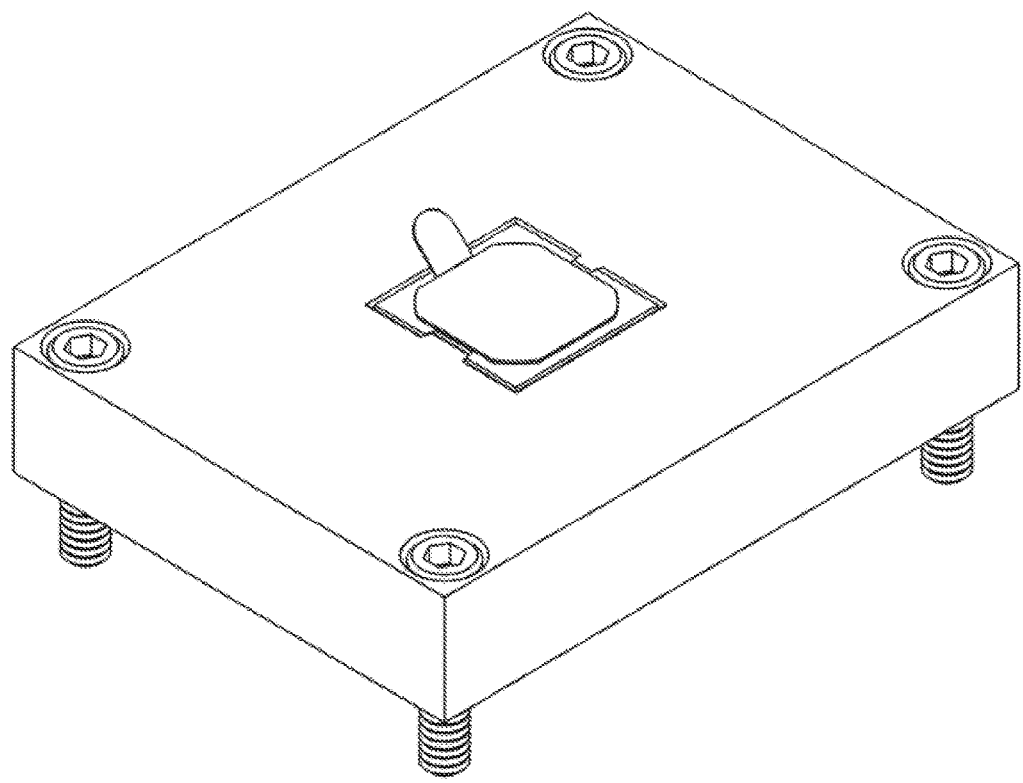
FIG. 18 illustrates a top right front perspective view of a preferred exemplary invention square SLC fixture embodiment with generic ophthalmic lens blank (OLB) installed.
Figure 19:
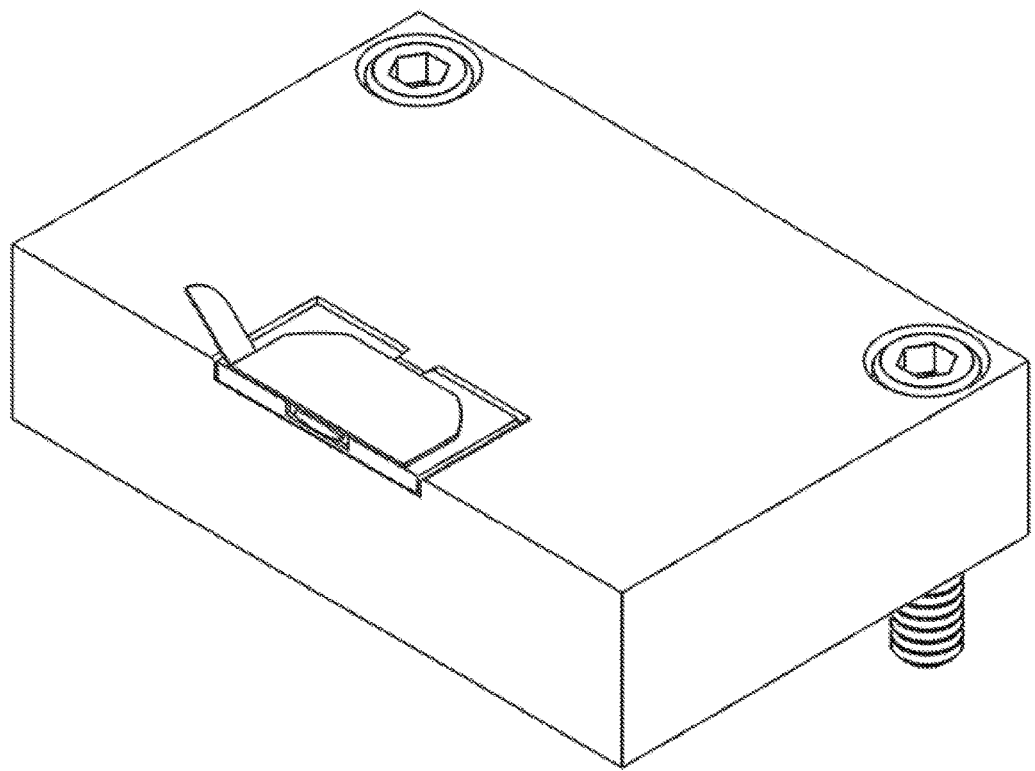
FIG. 19 illustrates a top right front perspective front section view of a preferred exemplary invention square SLC fixture embodiment with generic ophthalmic lens blank (OLB) installed.
Figure 20:
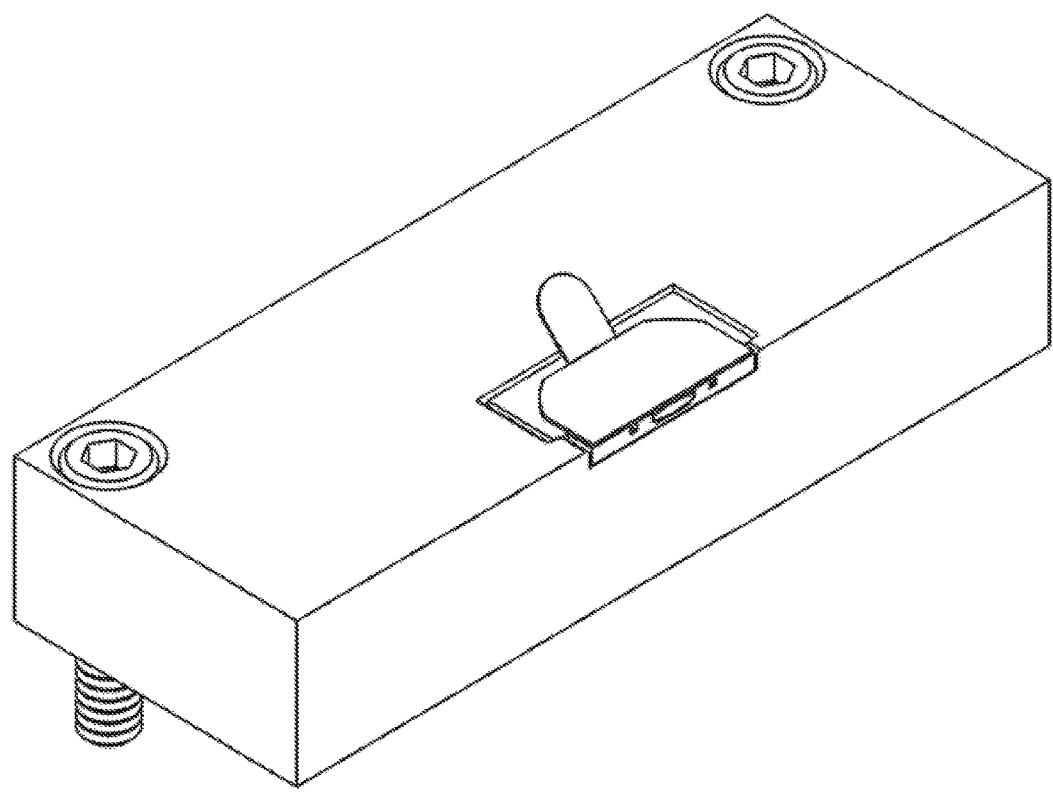
FIG. 20 illustrates a top right front perspective right section view of a preferred exemplary invention square SLC fixture embodiment with generic ophthalmic lens blank (OLB) installed.
Figure 21:
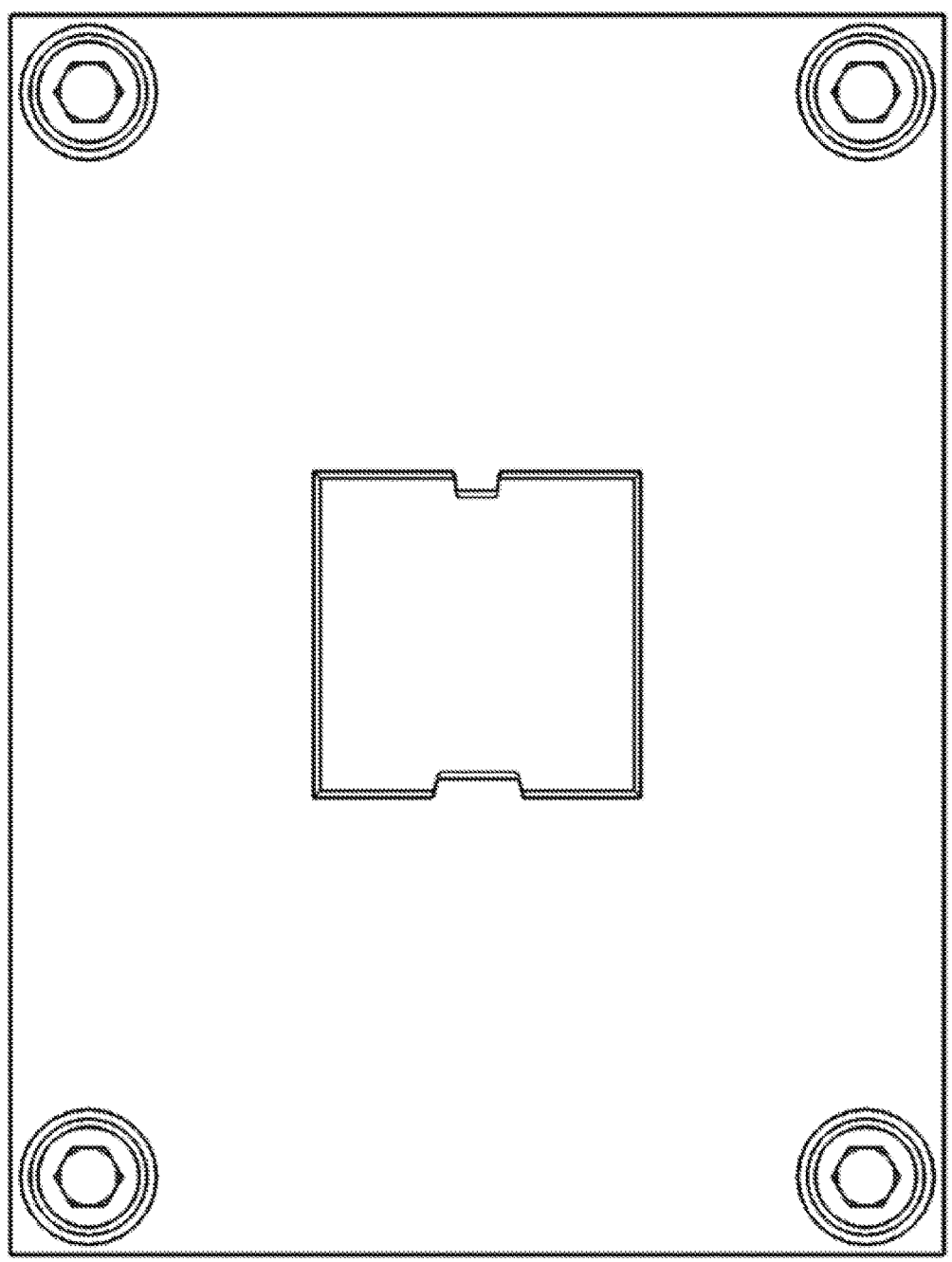
FIG. 21 illustrates a top view of a preferred exemplary invention square SLC fixture embodiment with generic ophthalmic lens blank (OLB) removed.
Figure 22:
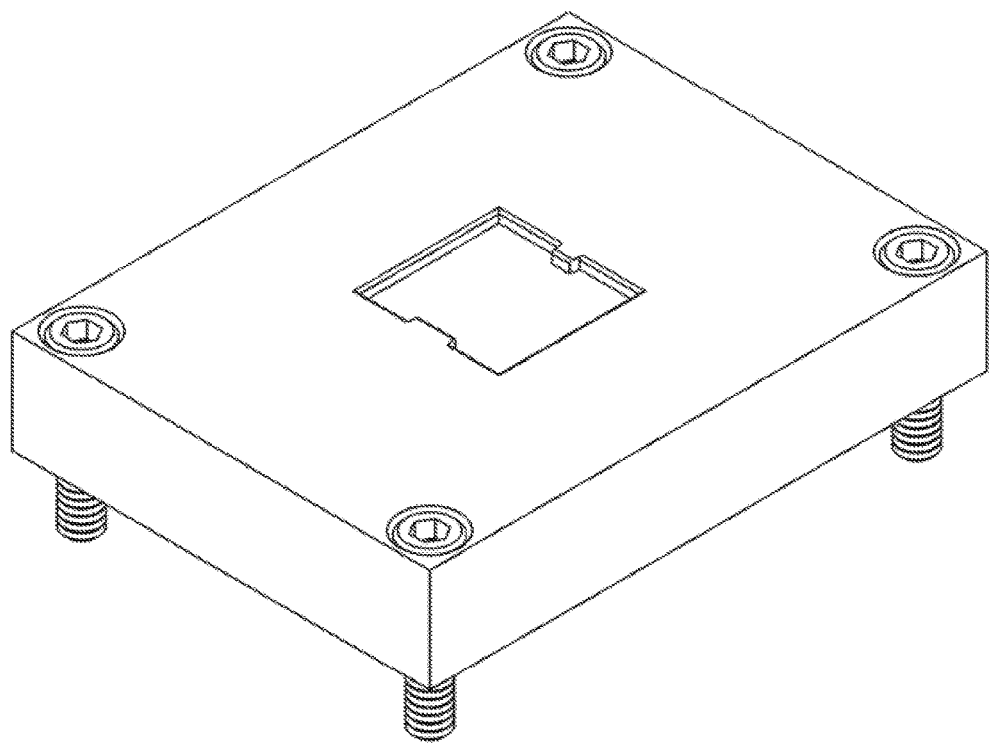
FIG. 22 illustrates a top right front perspective view of a preferred exemplary invention square SLC fixture embodiment with generic ophthalmic lens blank (OLB) removed.
Figure 23:
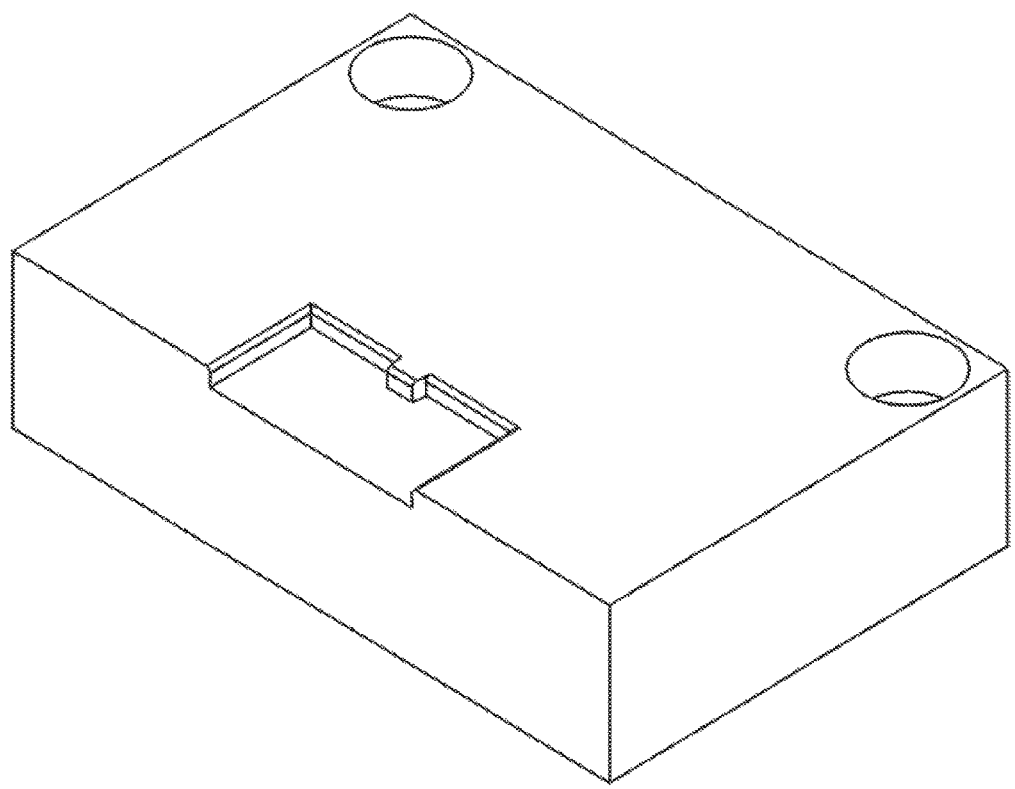
FIG. 23 illustrates a top right front perspective front section view of a preferred exemplary invention square SLC fixture embodiment with generic ophthalmic lens blank (OLB) removed.
Figure 24:
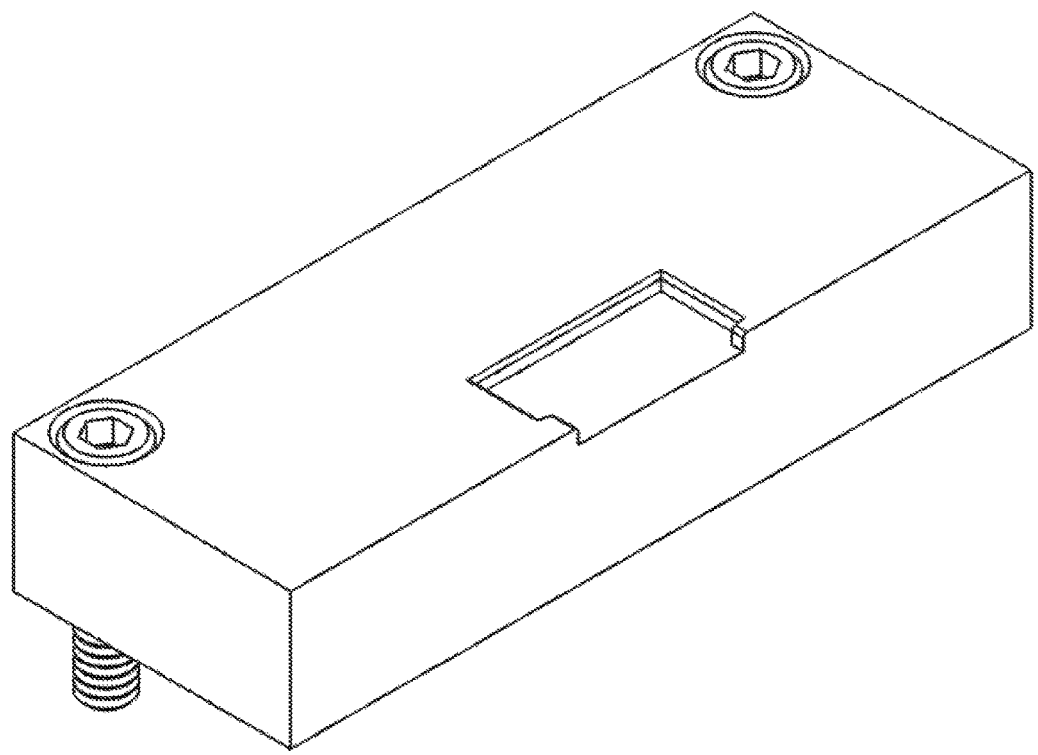
FIG. 24 illustrates a top right front perspective right section view of a preferred exemplary invention square SLC fixture embodiment with generic ophthalmic lens blank (OLB) removed.
Figure 25:
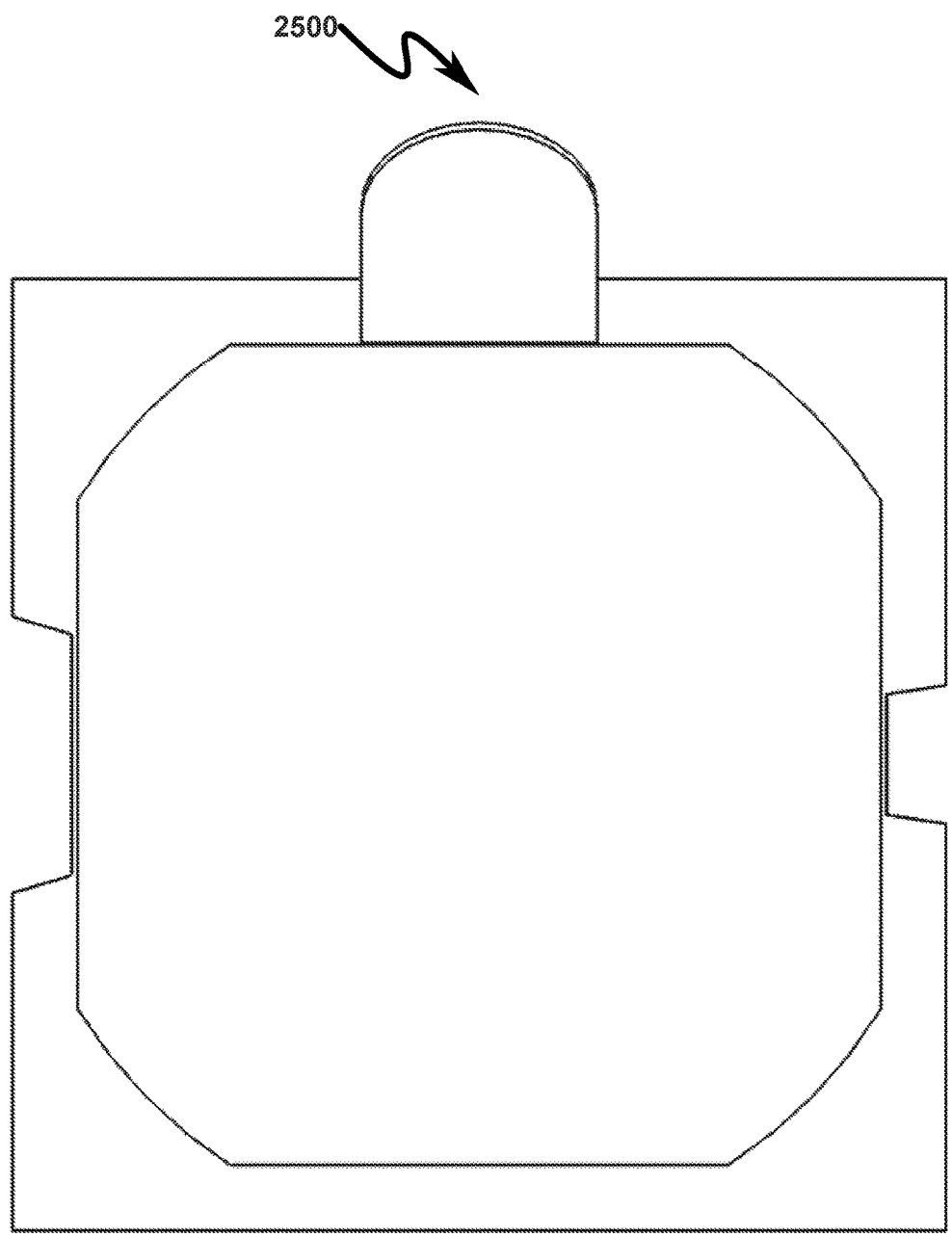
FIG. 25 illustrates a top view of a preferred exemplary invention square SLC ophthalmic lens blank (OLB) embodiment with hermetic seal installed.
Figure 26:
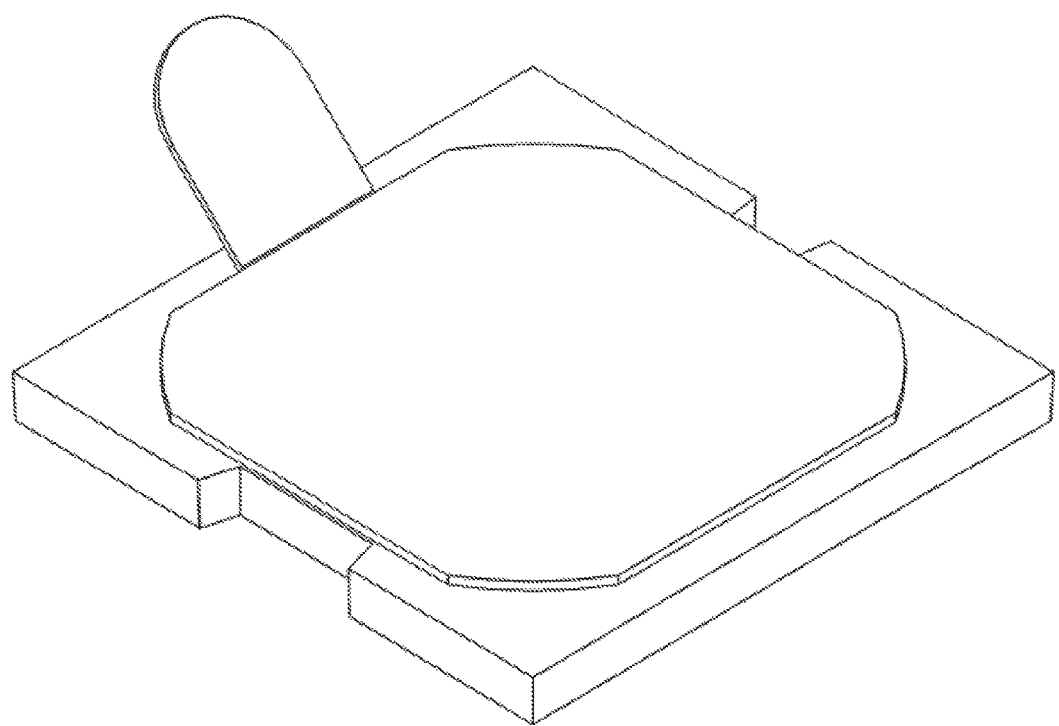
FIG. 26 illustrates a top right front perspective view of a preferred exemplary invention square SLC ophthalmic lens blank (OLB) embodiment with hermetic seal installed.
Figure 27:
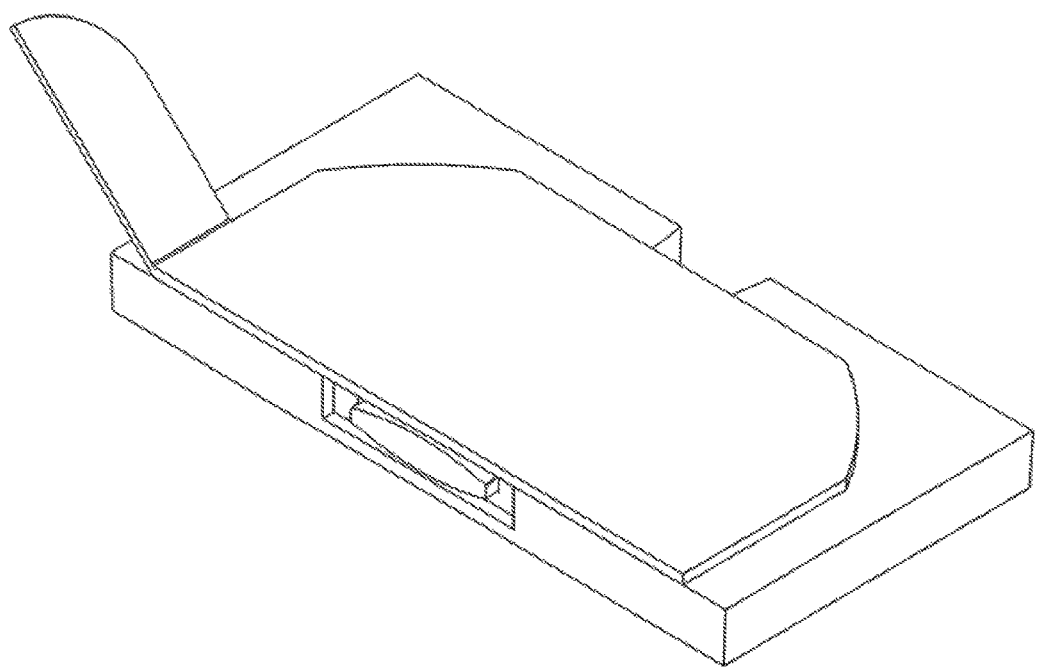
FIG. 27 illustrates a top right front perspective front section view of a preferred exemplary invention square SLC ophthalmic lens blank (OLB) embodiment with hermetic seal installed.
Figure 28:
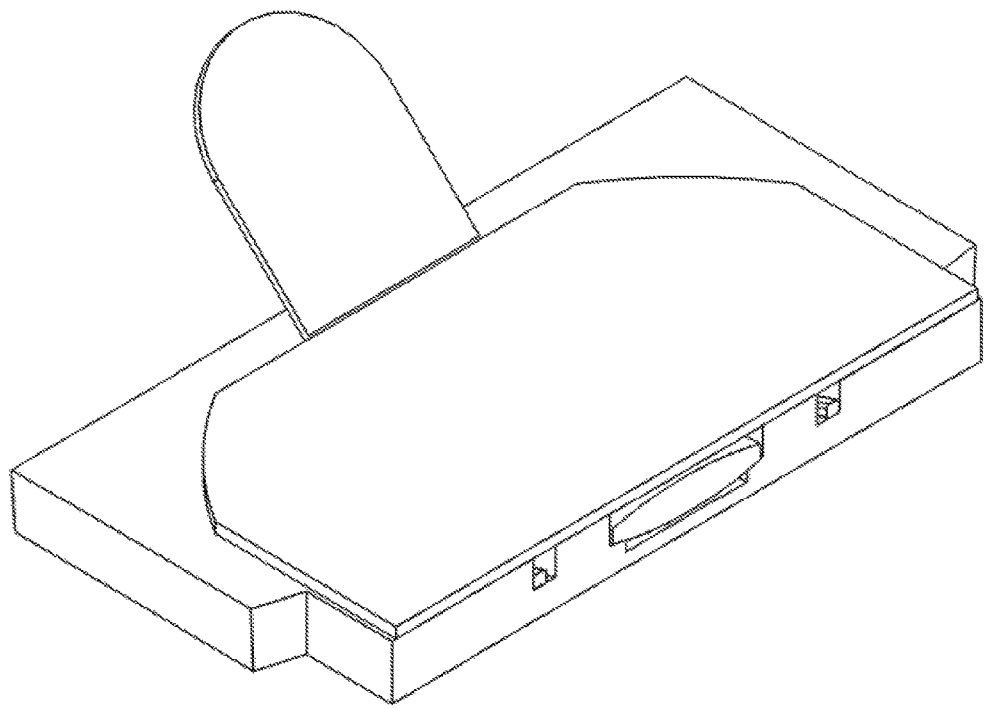
FIG. 28 illustrates a top right front perspective right section view of a preferred exemplary invention square SLC ophthalmic lens blank (OLB) embodiment with hermetic seal installed.
Figure 29:
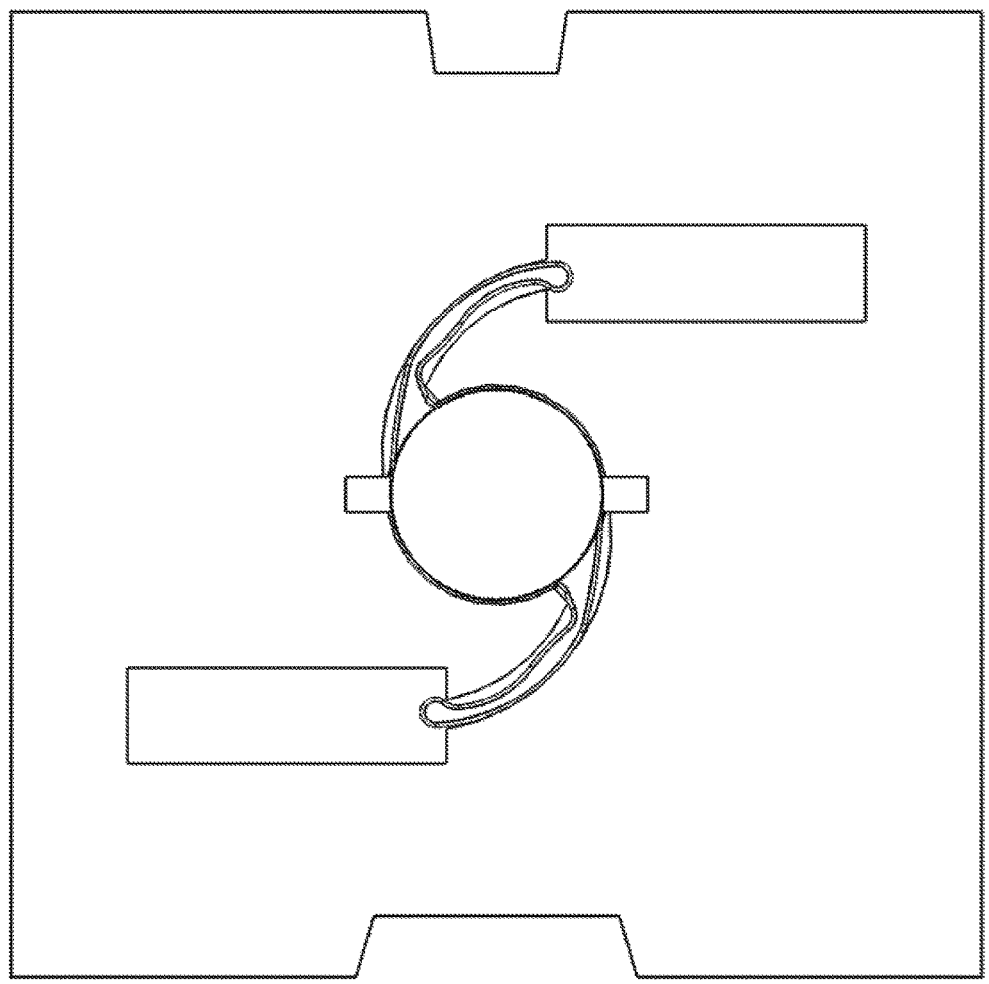
FIG. 29 illustrates a top view of a preferred exemplary invention square SLC ophthalmic lens blank (OLB) embodiment with hermetic seal removed.
Figure 30:
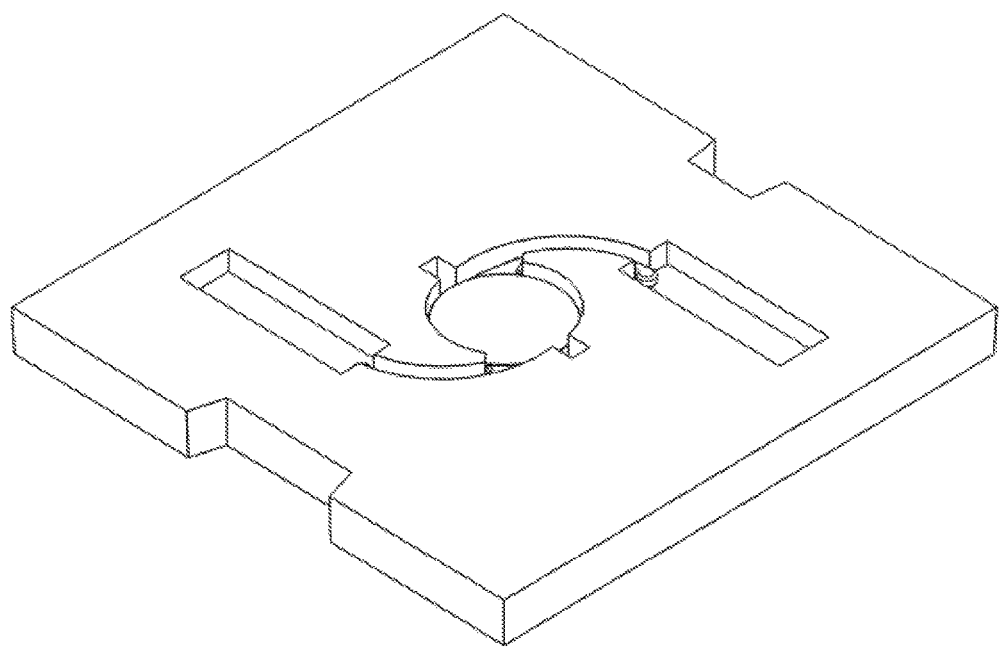
FIG. 30 illustrates a top right front perspective view of a preferred exemplary invention square SLC ophthalmic lens blank (OLB) embodiment with hermetic seal removed.
Figure 31:
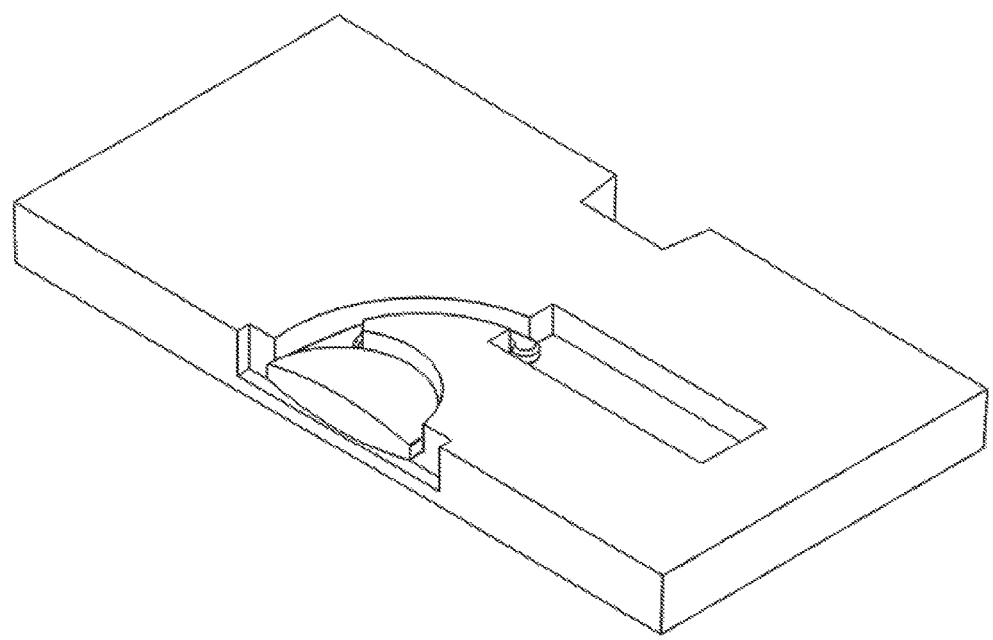
FIG. 31 illustrates a top right front perspective front section view of a preferred exemplary invention square SLC ophthalmic lens blank (OLB) embodiment with hermetic seal removed.
Figure 32:
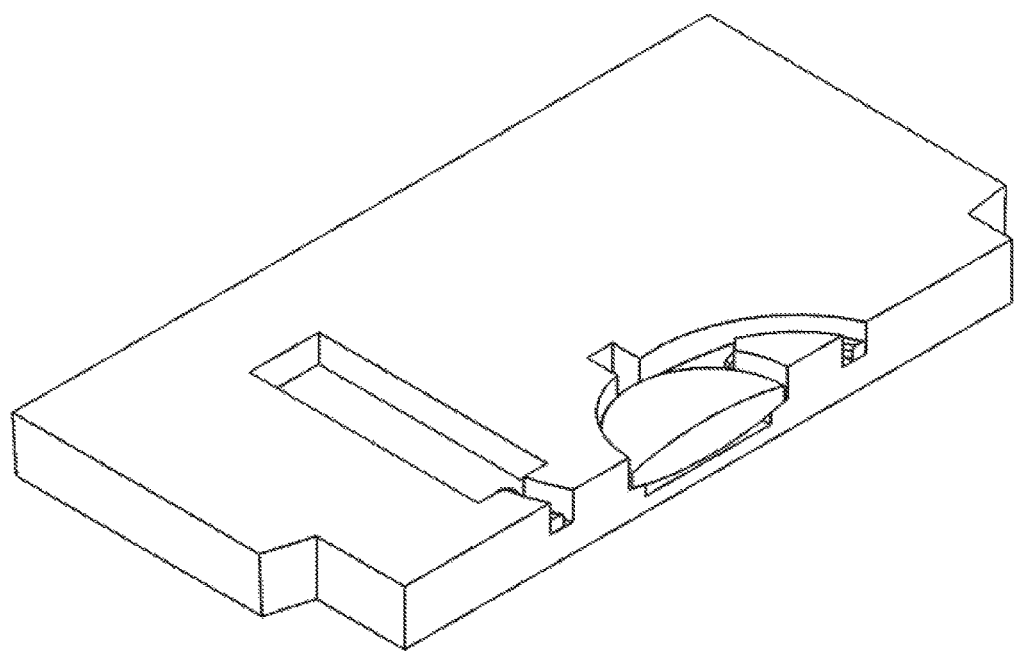
FIG. 32 illustrates a top right front perspective right section view of a preferred exemplary invention square SLC ophthalmic lens blank (OLB) embodiment with hermetic seal removed.

An exemplary square SLC embodiment is generally depicted in FIG. 17 (1700) FIG. 40 (4000). As depicted in FIG. 17 (1700) it can be seen that a baseplate fixture (1701) securely retains the square SLC (1702) to permit laser radiation to be focused on the OLB contained within the SLC (1702). Further detail of the interaction between the baseplate fixture (1701) and the square SLC (1702) can be seen by inspection of FIG. 17 (1700)-FIG. 24 (2400), Detail views of the SLC with OLB installed are depicted in FIG. 25 (2500)-FIG. 32 (3200). The cavity in which the OLB is retained within the SLC is generally filled with a fluid suitable for transmission of laser radiation to the OLB during the customization process. This fluid may include but is not limited to distilled water and/or deionized water and/or a physiological saline solution.

Figure 33:
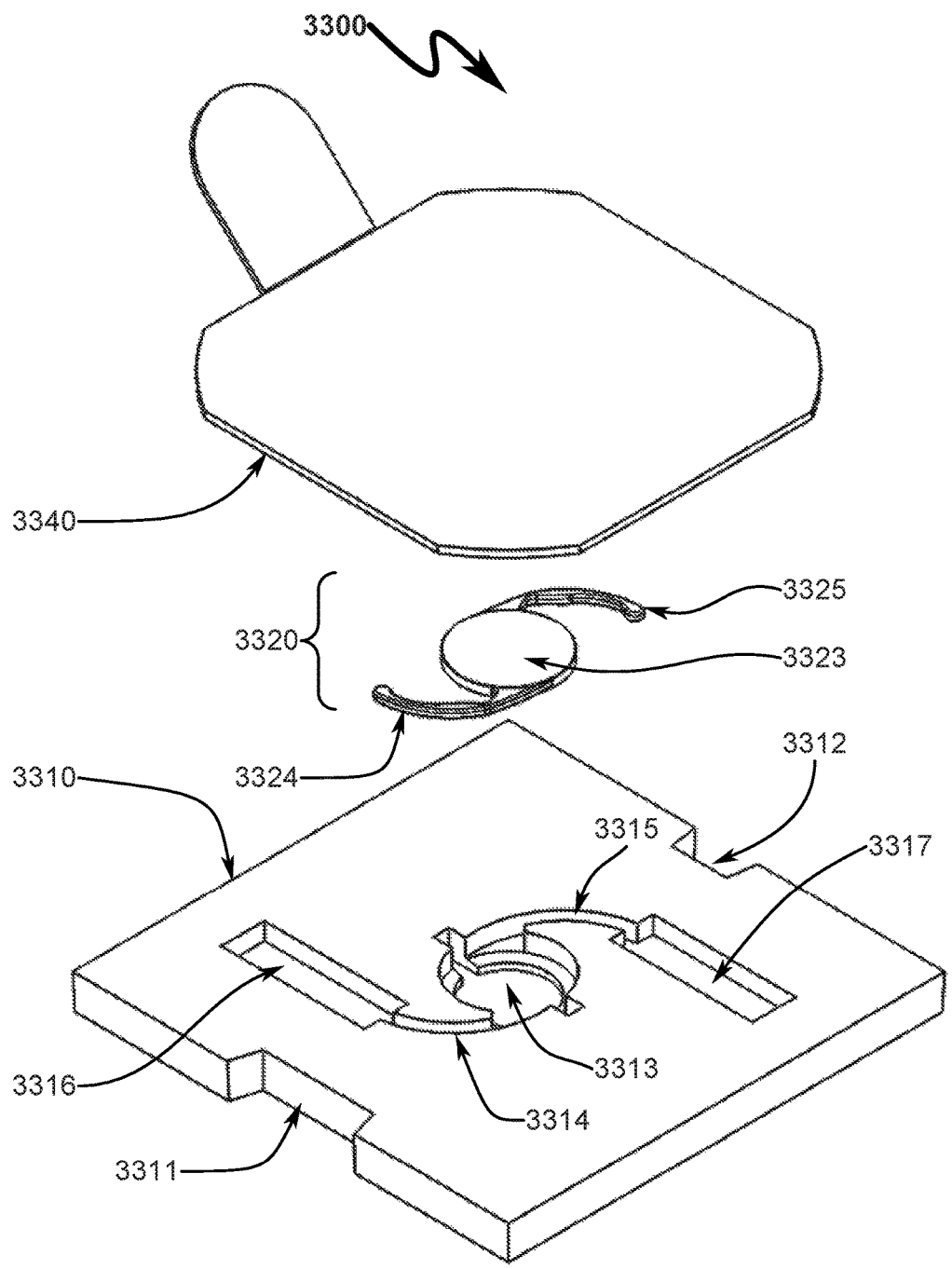
FIG. 33 illustrates a top right front perspective assembly view of a preferred exemplary invention square SLC ophthalmic lens blank (OLB) embodiment.
Figure 34:
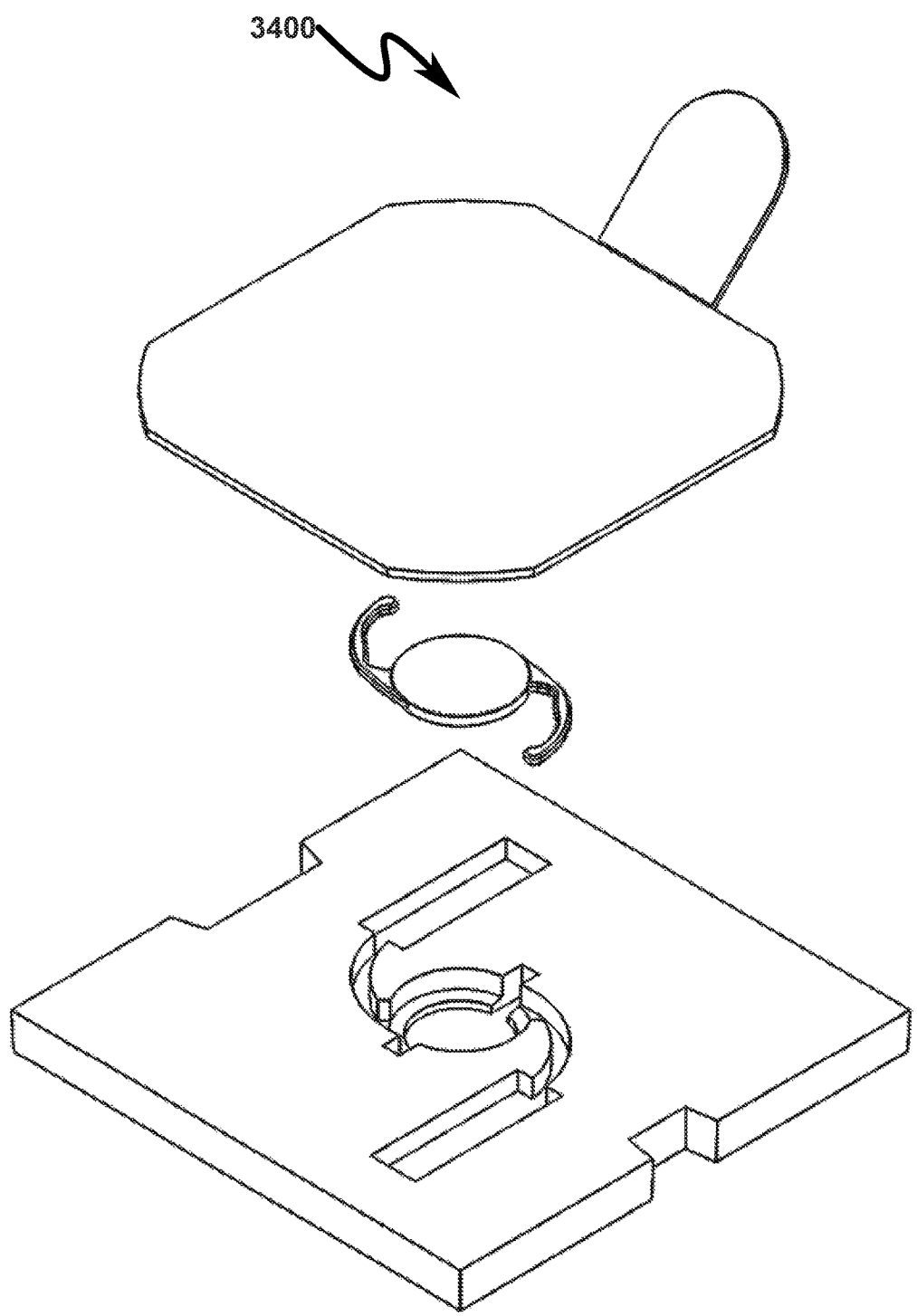
FIG. 34 illustrates a top right rear perspective assembly view of a preferred exemplary invention square SLC ophthalmic lens blank (OLB) embodiment.
Figure 35:
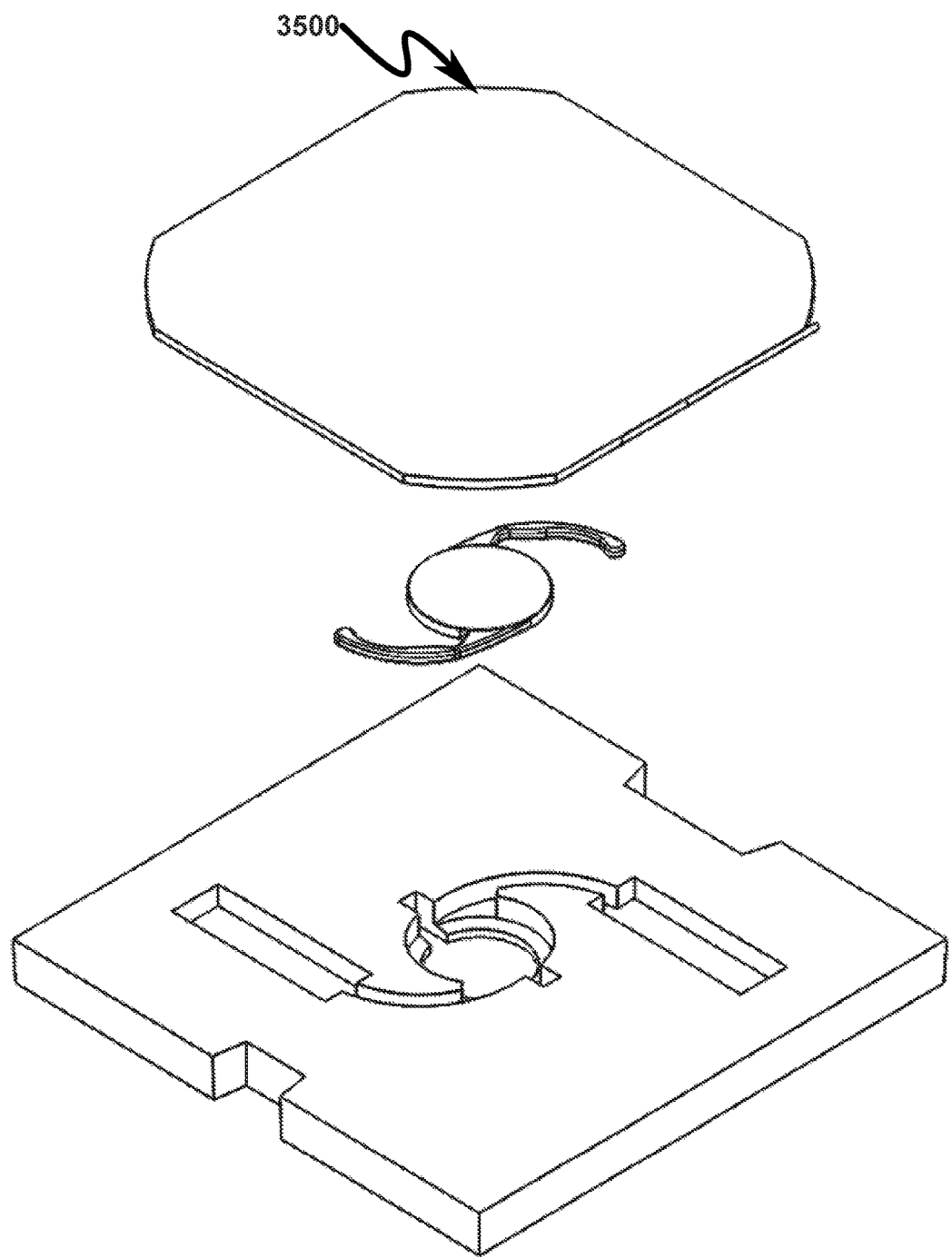
FIG. 35 illustrates a top left rear perspective assembly view of a preferred exemplary invention square SLC ophthalmic lens blank (OLB) embodiment.
Figure 36:
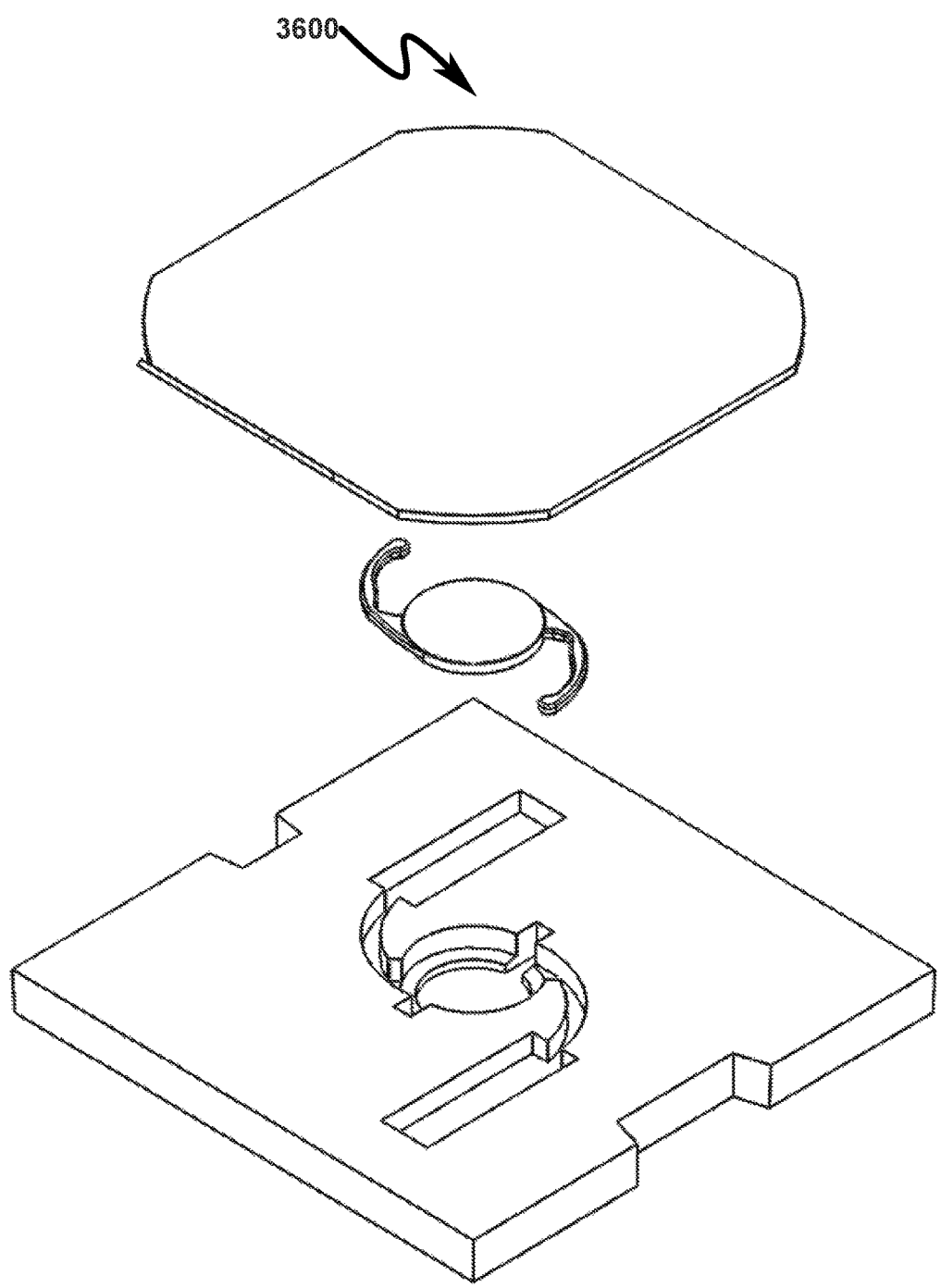
FIG. 36 illustrates a top left front perspective assembly view of a preferred exemplary invention square SLC ophthalmic lens blank (OLB) embodiment.
Figure 37:
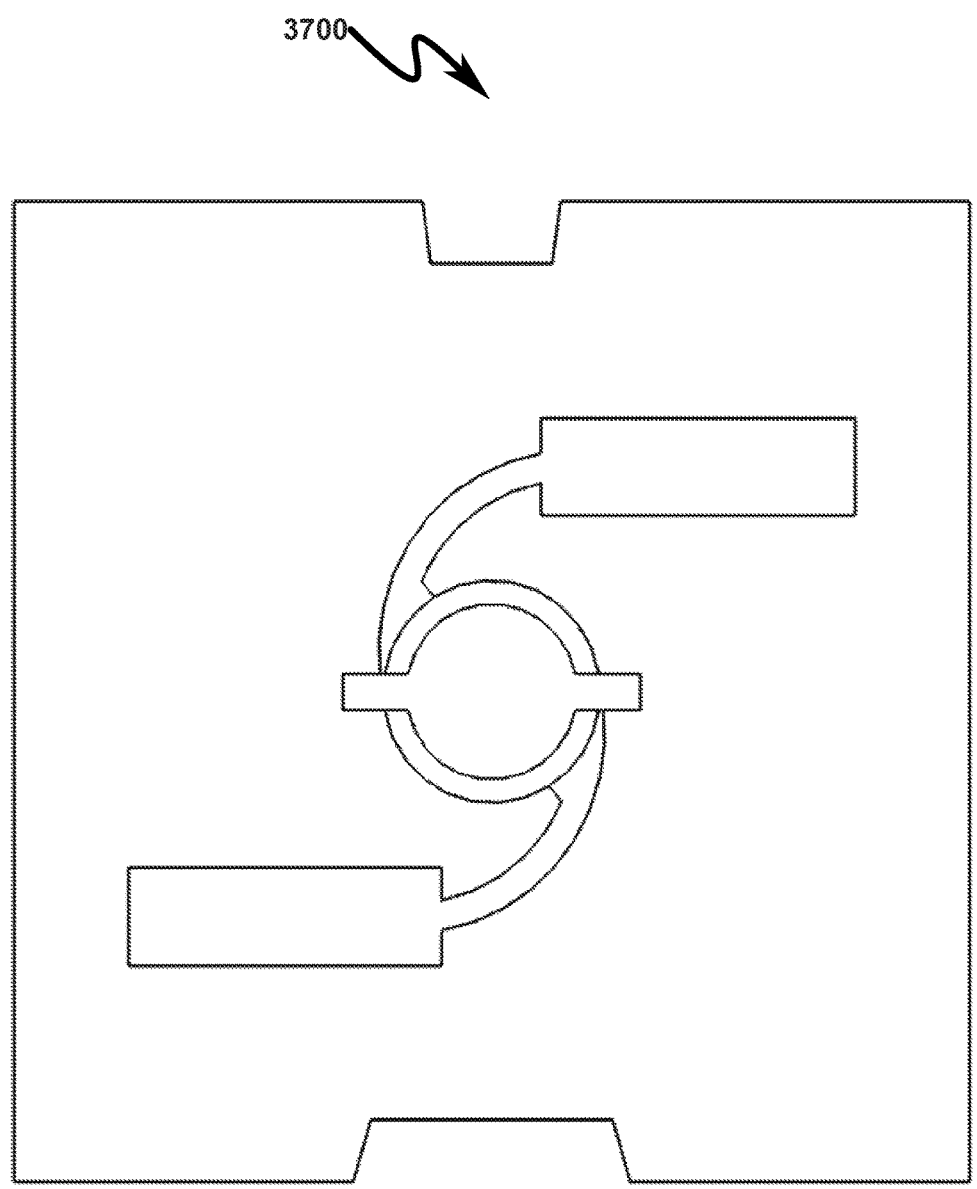
FIG. 37 illustrates a top view of a preferred exemplary invention square SLC fixture embodiment.
Figure 38:
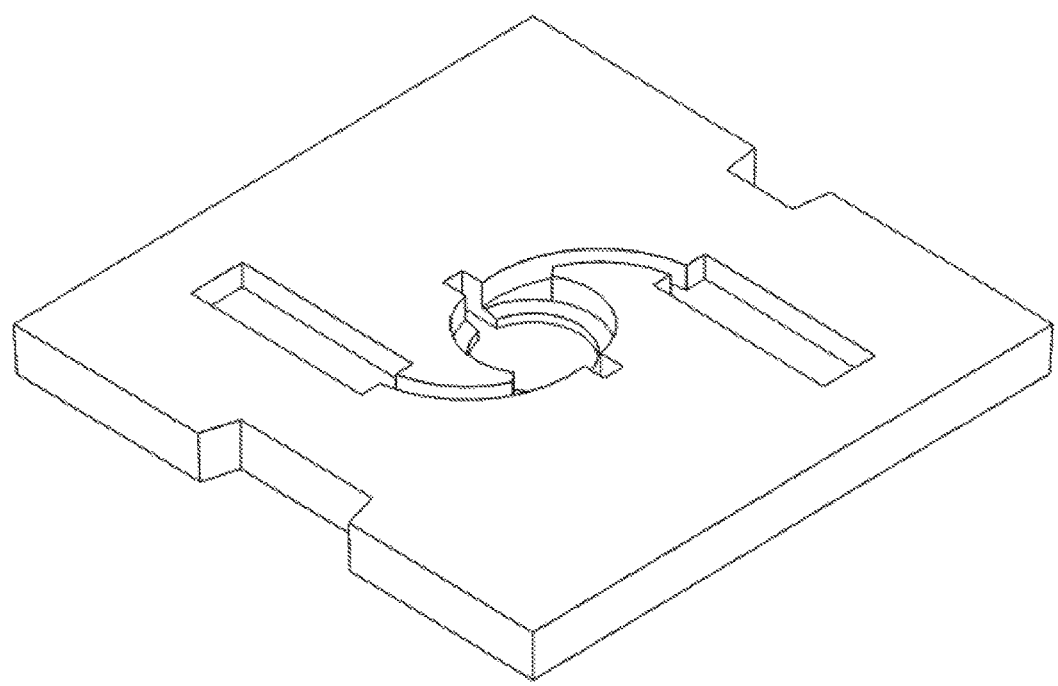
FIG. 38 illustrates a top right front perspective view of a preferred exemplary invention square SLC fixture embodiment.
Figure 39:
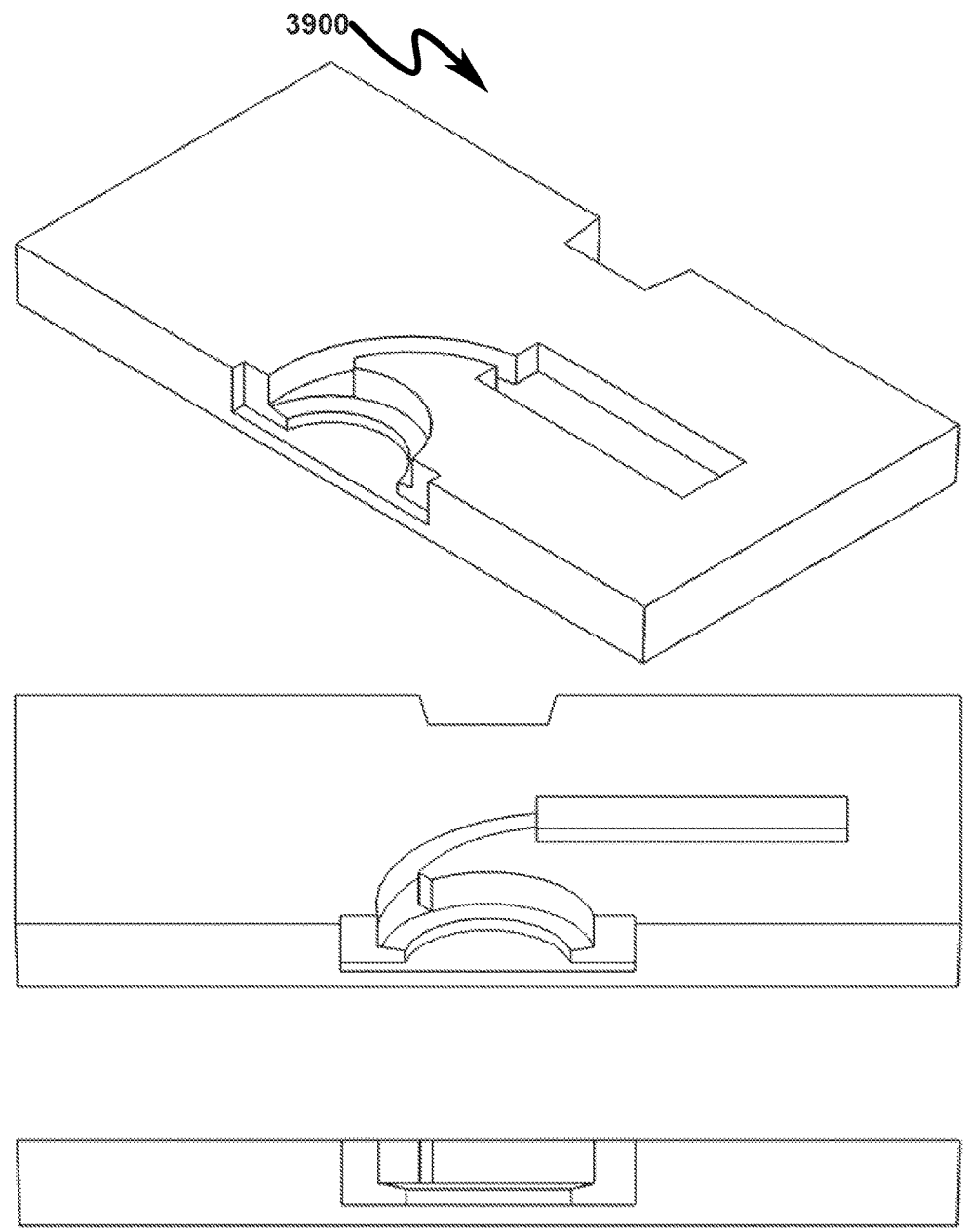
FIG. 39 illustrates top right front perspective front section views of a preferred exemplary invention square SLC fixture embodiment.

Additional detail of the exemplary SLC and OLB can be seen by inspecting FIG. 33 (3300)-FIG. 40 (4000) in which the SLC (3310) is depicted having one or more lens position identifier (LPI) (3311, 3312) features to ensure that the OLB (3320) is properly oriented and secured for laser irradiation when installed in the baseplate fixture (1701). A lens cavity (3313) and corresponding haptic retainers (3314, 3315) are provided within the SLC to secure the OLB (3320) lens (3323) and corresponding lens haptics (3324, 3325). Haptic: access ports (3316, 3317) located at the distal ends of the haptic retainers (3314, 3315) allow the lens (3320) to be extracted from the SLC using the lens haptics (3324, 3325) via tweezers or other suitable tool after the customization process is completed.

A sealing lid (3340) is provided to seal the SLC (3310) and permit the SLC (3310)/OLB (3320) combination to be sterilized after assembly. In this configuration the sealing lid (3340) may be configured to transmit laser radiation through the liquid covering the OLB (3320) or in some circumstances the sealing lid (3340) may be removed prior to customization in which case the laser radiation is directly impinges the liquid covering the OLB (3320) and then impinges the OLB (3320) to affect refractive index changes in the OLB (3320) to generate a custom lens structure. If laser radiation is to be directed through the sealing lid (3340), the sealing lid (3340) will be constructed of material having a refractive index in the range of 1.05 to 1.65.

Exemplary Rectangular Cartridge SLC Embodiment (4100)-(6400)

Figure 41:
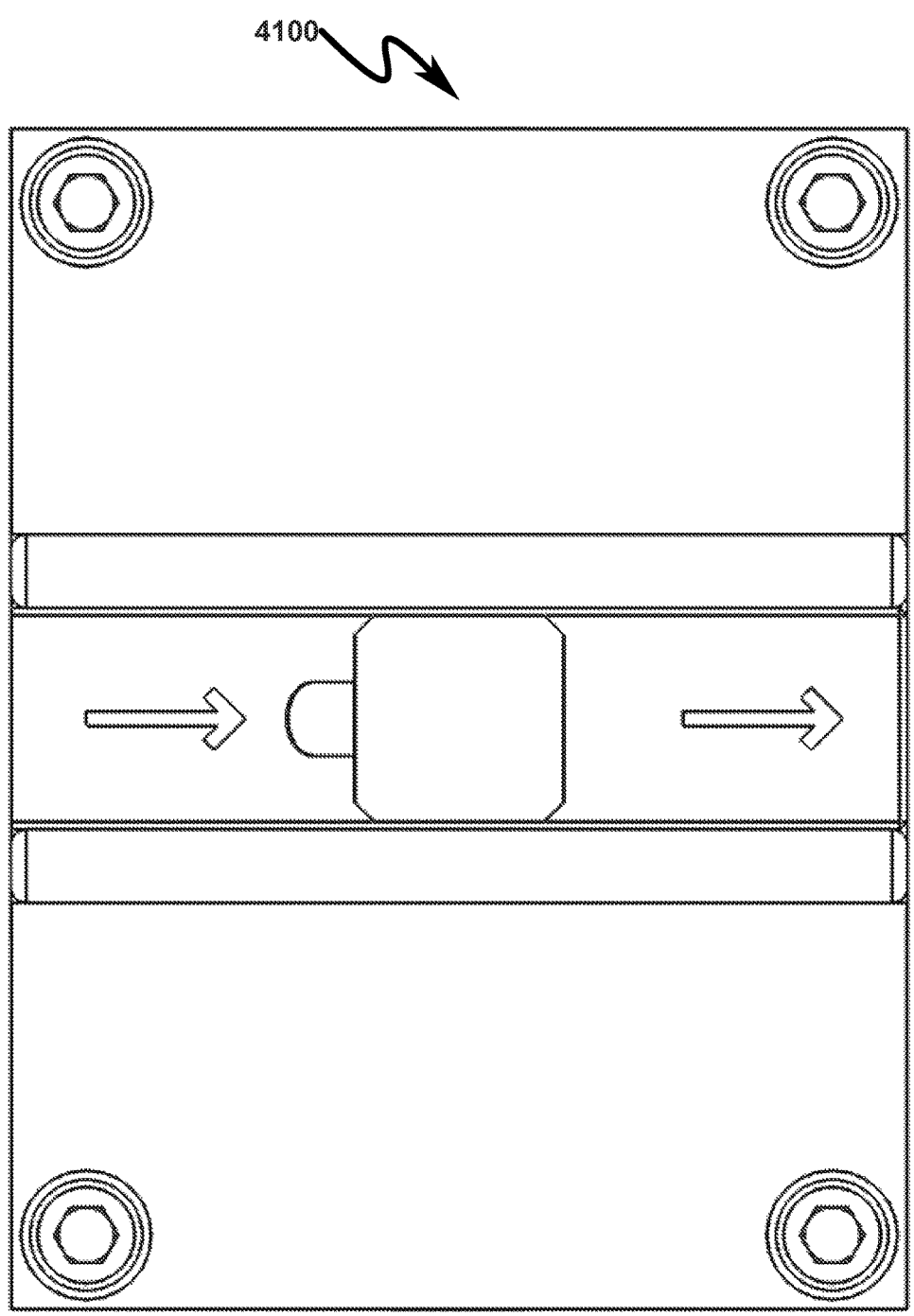
FIG. 41 illustrates a top view of a preferred exemplary invention rectangular cartridge SLC fixture embodiment with generic ophthalmic lens blank (OLB) installed.
Figure 42:
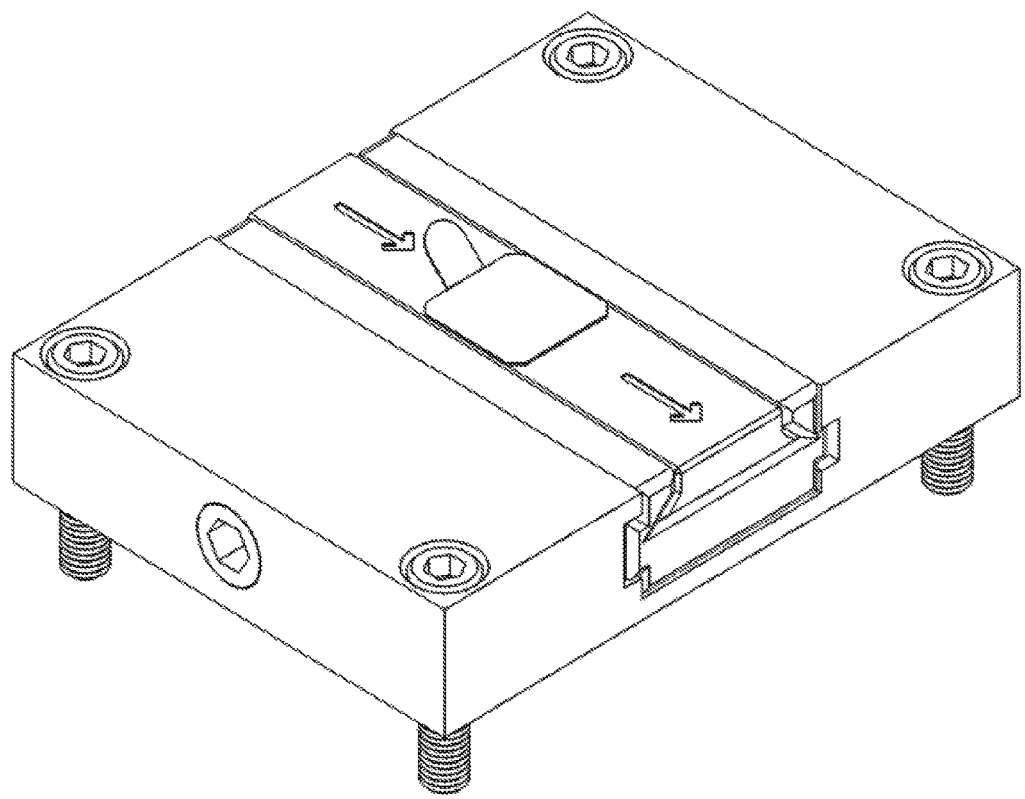
FIG. 42 illustrates a top right front perspective view of a preferred exemplary invention rectangular cartridge SLC fixture embodiment with generic ophthalmic lens blank (OLB) installed.
Figure 43:
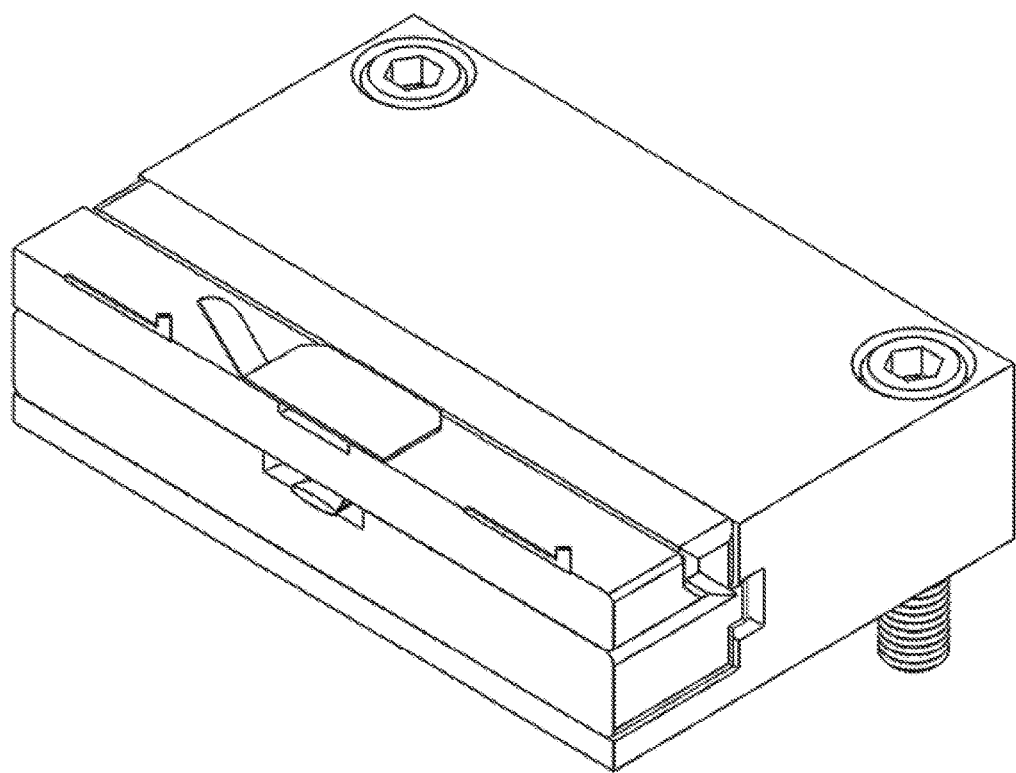
FIG. 43 illustrates a top right front perspective front section view of a preferred exemplary invention rectangular cartridge SLC fixture embodiment with generic ophthalmic lens blank (OLB) installed.
Figure 44:
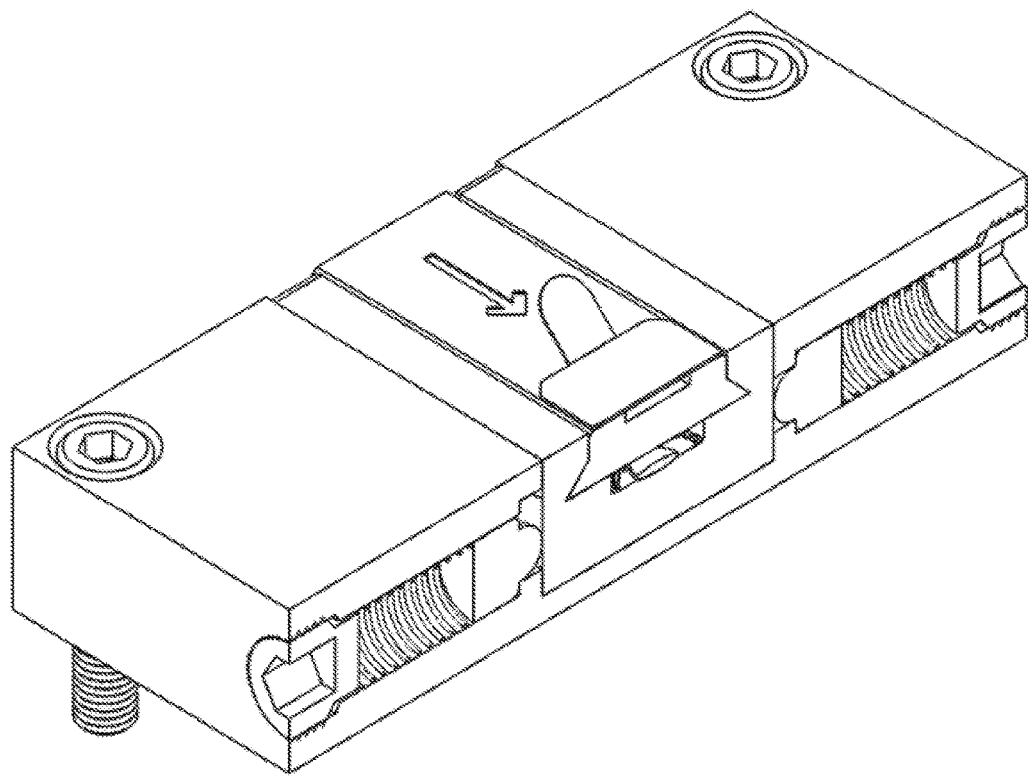
FIG. 44 illustrates a top right front perspective right section view of a preferred exemplary invention rectangular cartridge SLC fixture embodiment with generic ophthalmic lens blank (OLB) installed.
Figure 45:
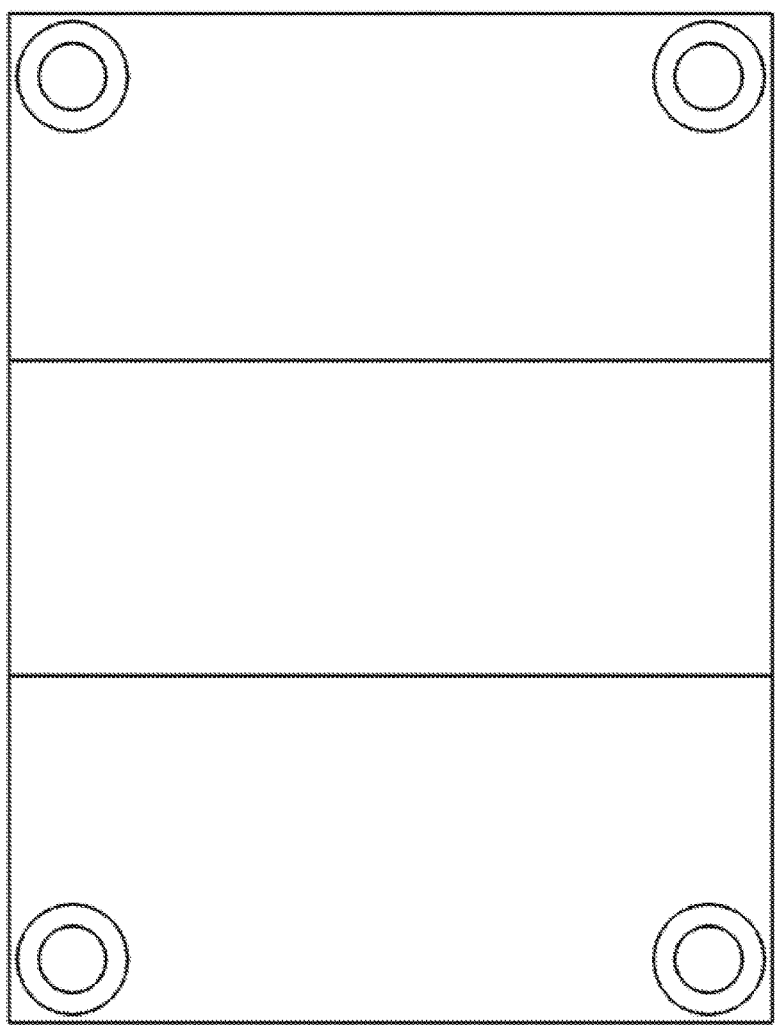
FIG. 45 illustrates a top view of a preferred exemplary invention rectangular cartridge SLC fixture embodiment with generic ophthalmic lens blank (OLB) removed.
Figure 46:
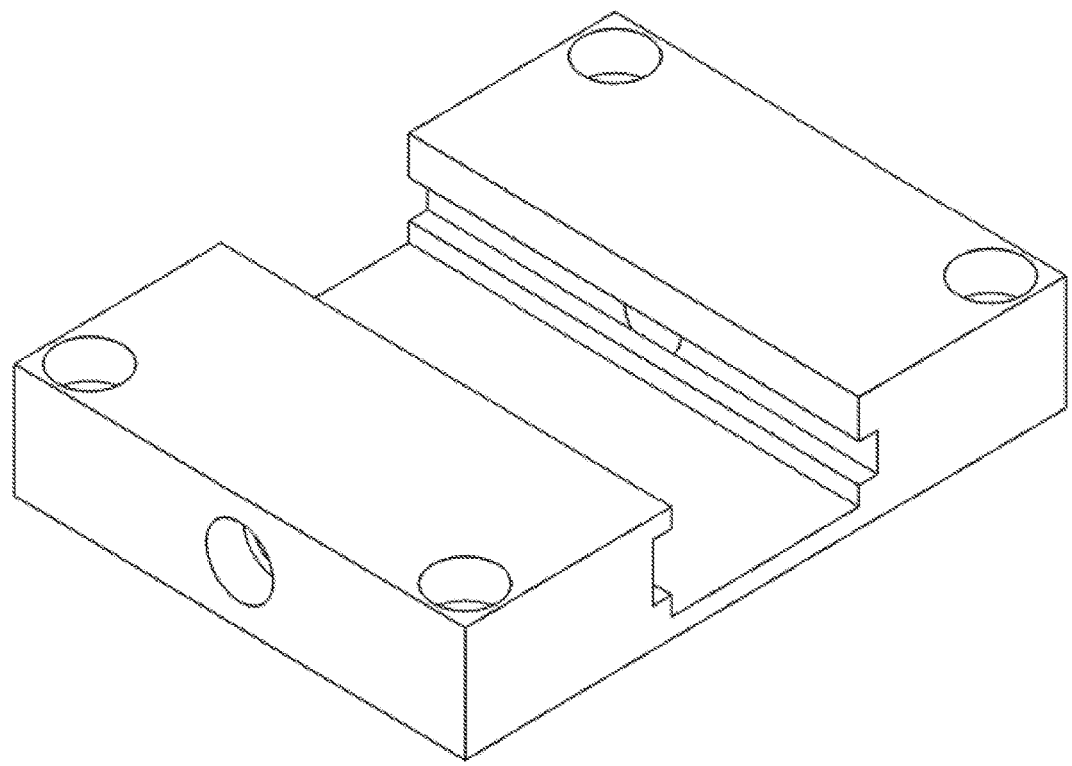
FIG. 46 illustrates a top right front perspective view of a preferred exemplary invention rectangular cartridge SLC fixture embodiment with generic ophthalmic lens blank (OLB) removed.
Figure 47:
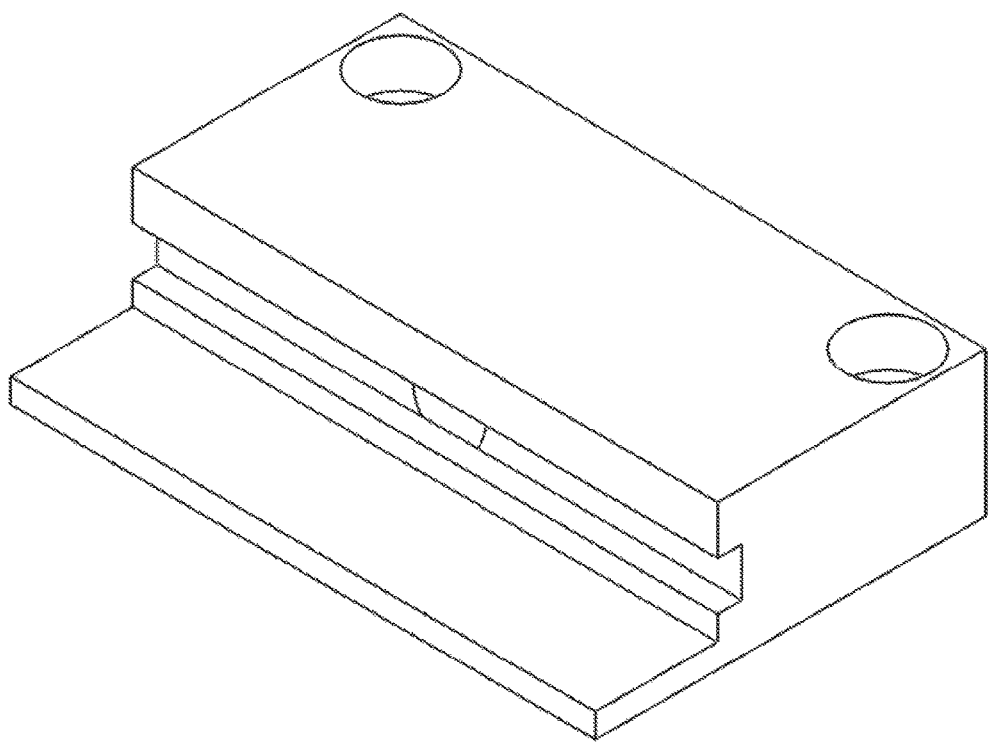
FIG. 47 illustrates a top right front perspective front section view of a preferred exemplary invention rectangular cartridge SLC fixture embodiment with generic ophthalmic lens blank (OLB) removed.
Figure 56:
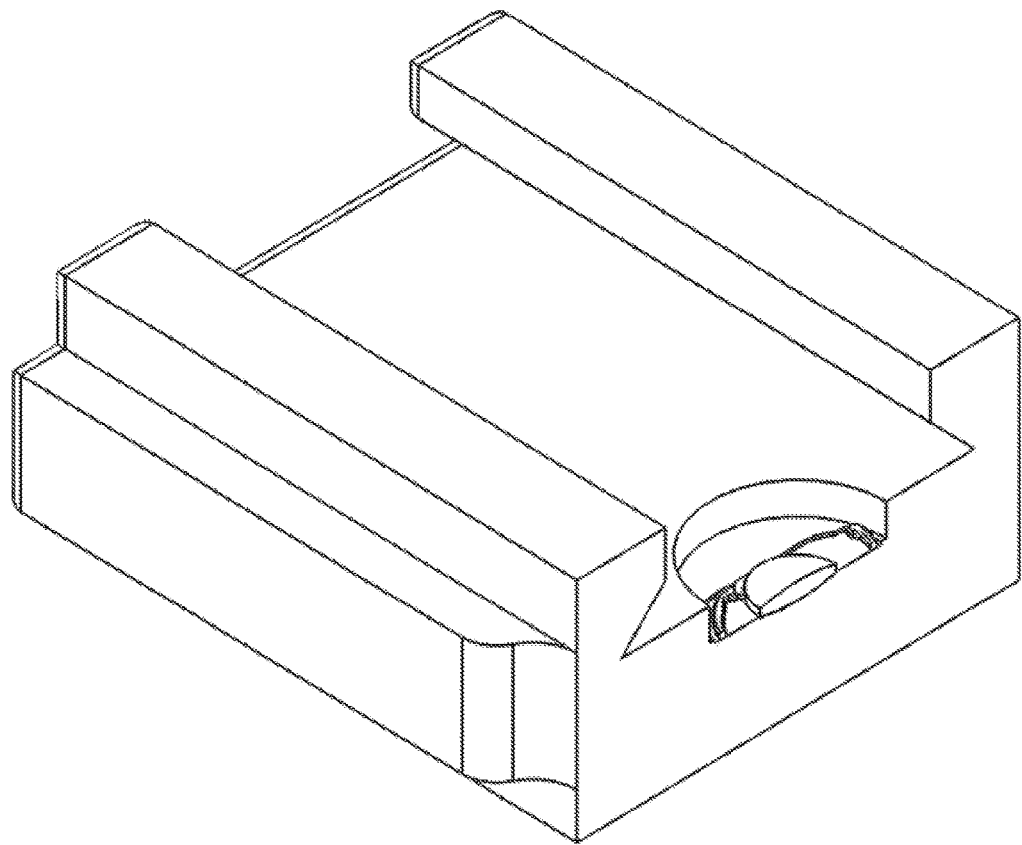
FIG. 56 illustrates a top right front perspective right section view of a preferred exemplary invention rectangular cartridge SLC ophthalmic lens blank (OLB) embodiment with hermetic seal removed.

An exemplary rectangular cartridge SLC embodiment is generally depicted in FIG. 41 (4100)-FIG. 64 (6400). As depicted in FIG. 41 (4100) it can be seen that a baseplate fixture (4101) securely retains the rectangular cartridge SLC (4102) to permit laser radiation to be focused on the OLB contained within the SLC (4102). Further detail of the interaction between the baseplate fixture (4101) and the square SLC (4102) can be seen by inspection of FIG. 41 (4100)-FIG. 48 (4800). Detail views of the SLC with OLB installed are depicted in FIG. 49 (4900)-FIG. 56 (5600). The cavity in which the OLB is retained within the SLC is generally filled with a fluid suitable for transmission, of laser radiation to the OLB during the customization process. This fluid may include but is not limited to distilled water and/or deionized water and/or a physiological saline solution.

Figure 57:
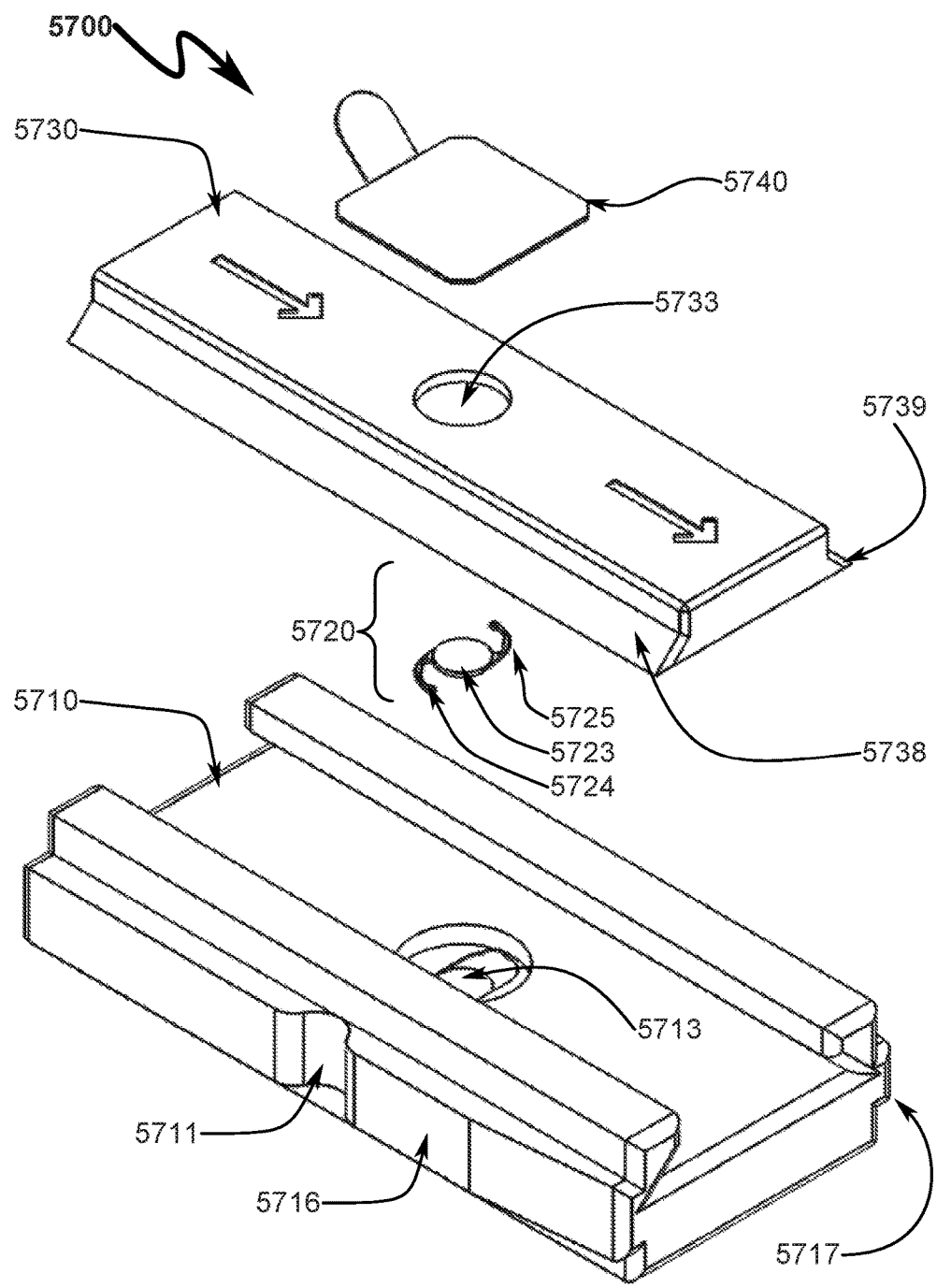
FIG. 57 illustrates a top right front perspective assembly view of a preferred exemplary invention rectangular cartridge SLC ophthalmic lens blank (OLB) retainer embodiment.
Figure 58:
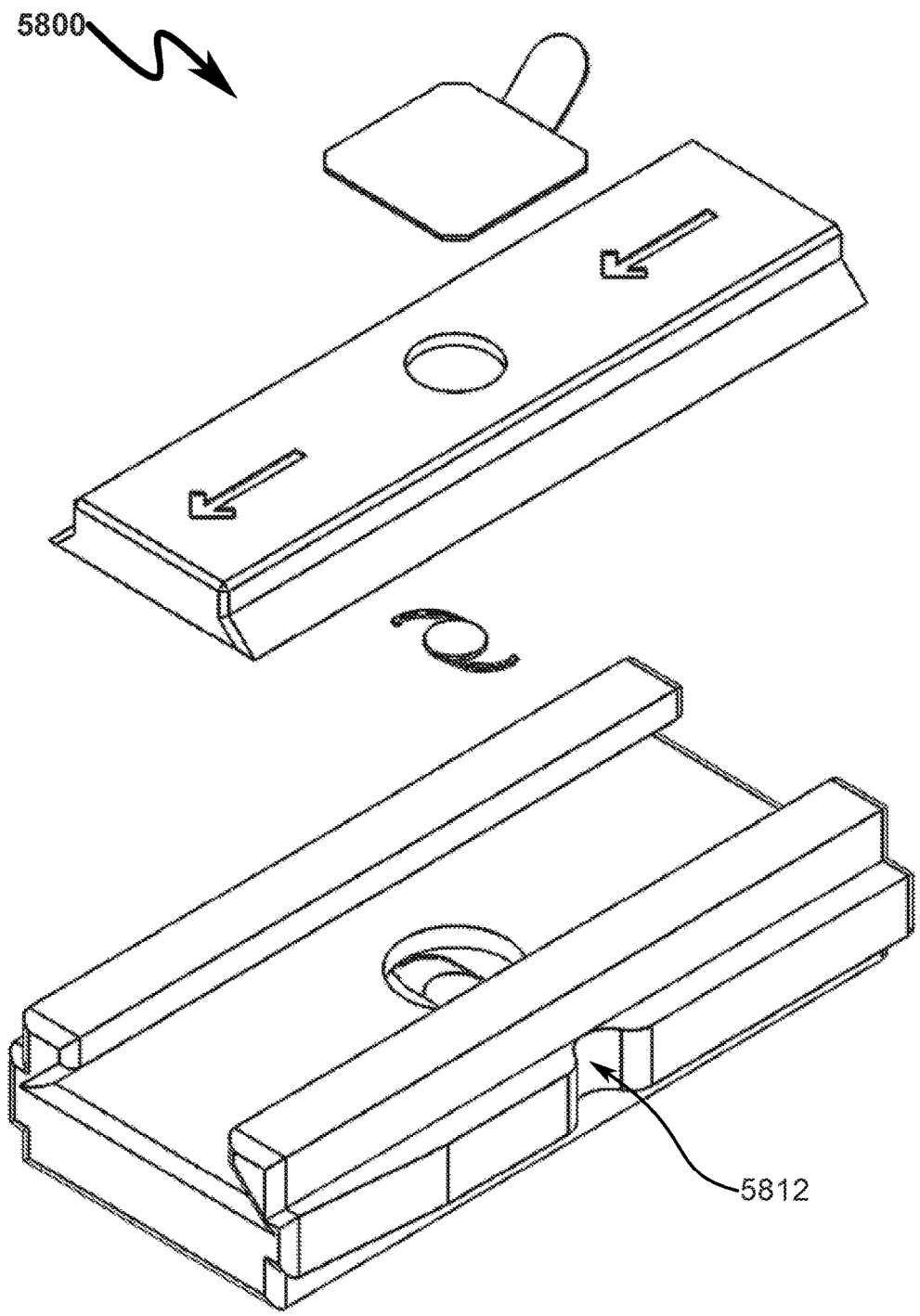
FIG. 58 illustrates a top right rear perspective assembly view of a preferred exemplary invention rectangular cartridge SLC ophthalmic lens blank (OLB) retainer embodiment.
Figure 59:
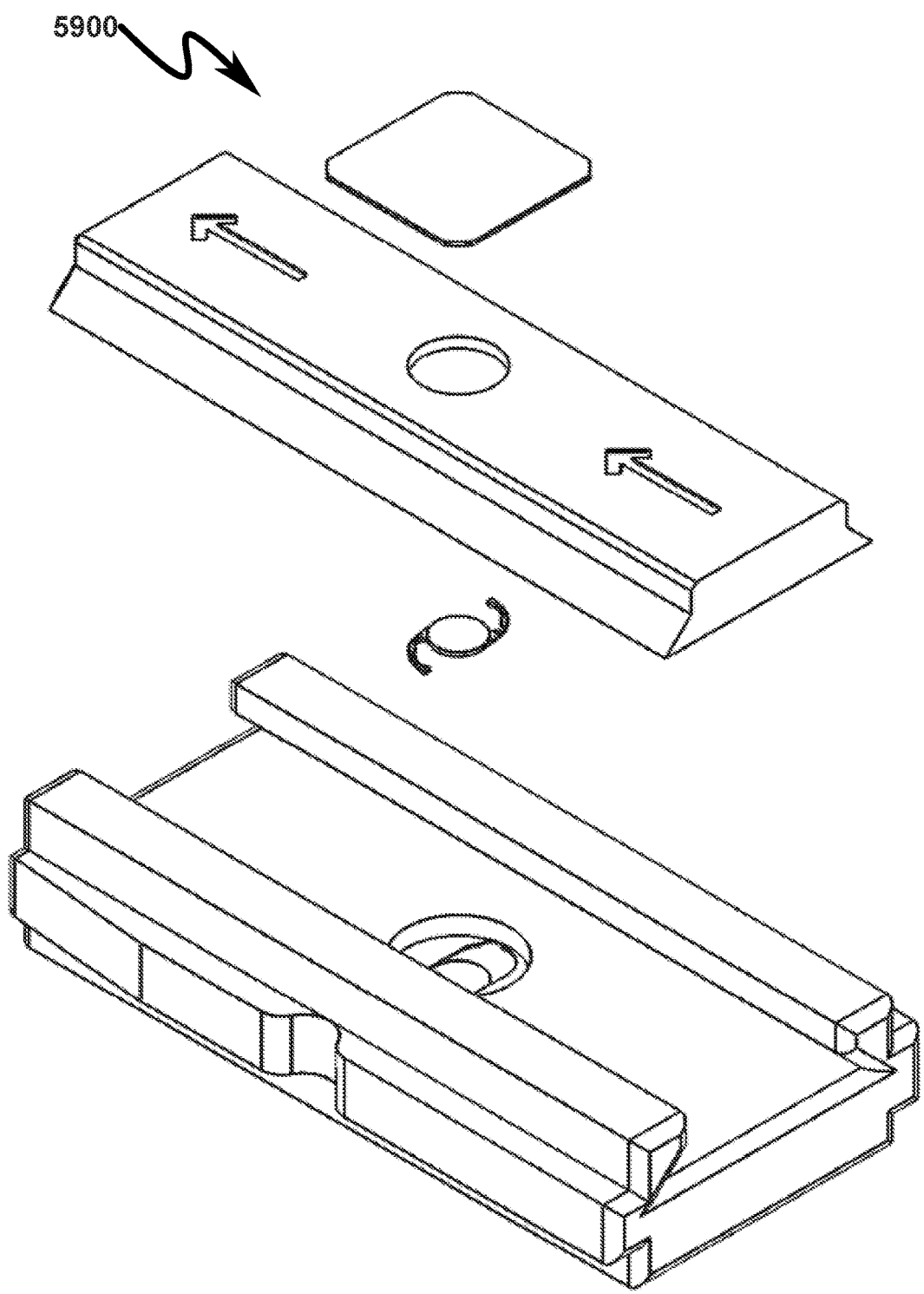
FIG. 59 illustrates a top left rear perspective assembly view of a preferred exemplary invention rectangular cartridge SLC ophthalmic lens blank (OLB) retainer embodiment.
Figure 60:
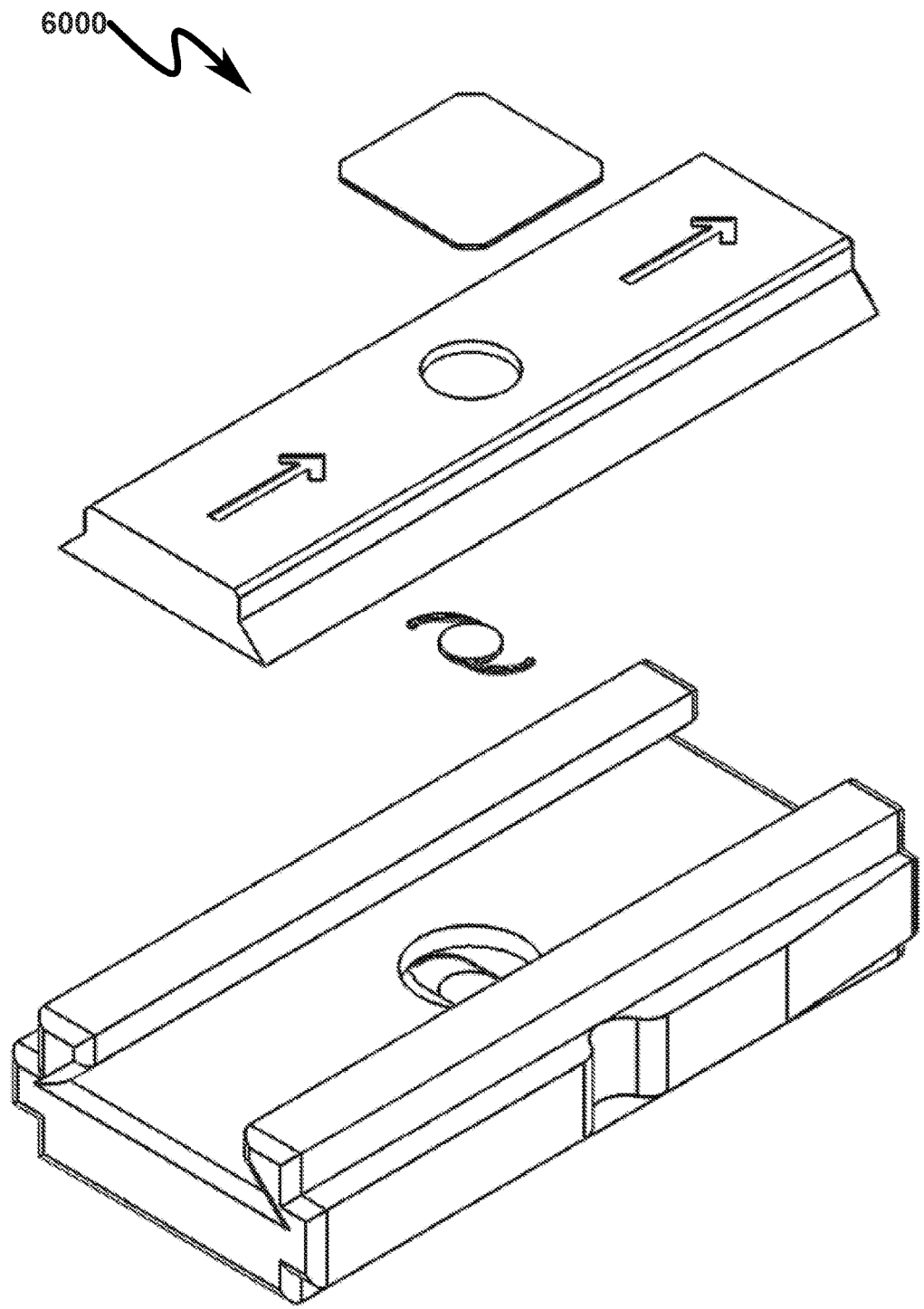
FIG. 60 illustrates a top left front perspective assembly view of a preferred exemplary invention rectangular cartridge SLC ophthalmic lens blank (OLB) retainer embodiment.
Figure 61:
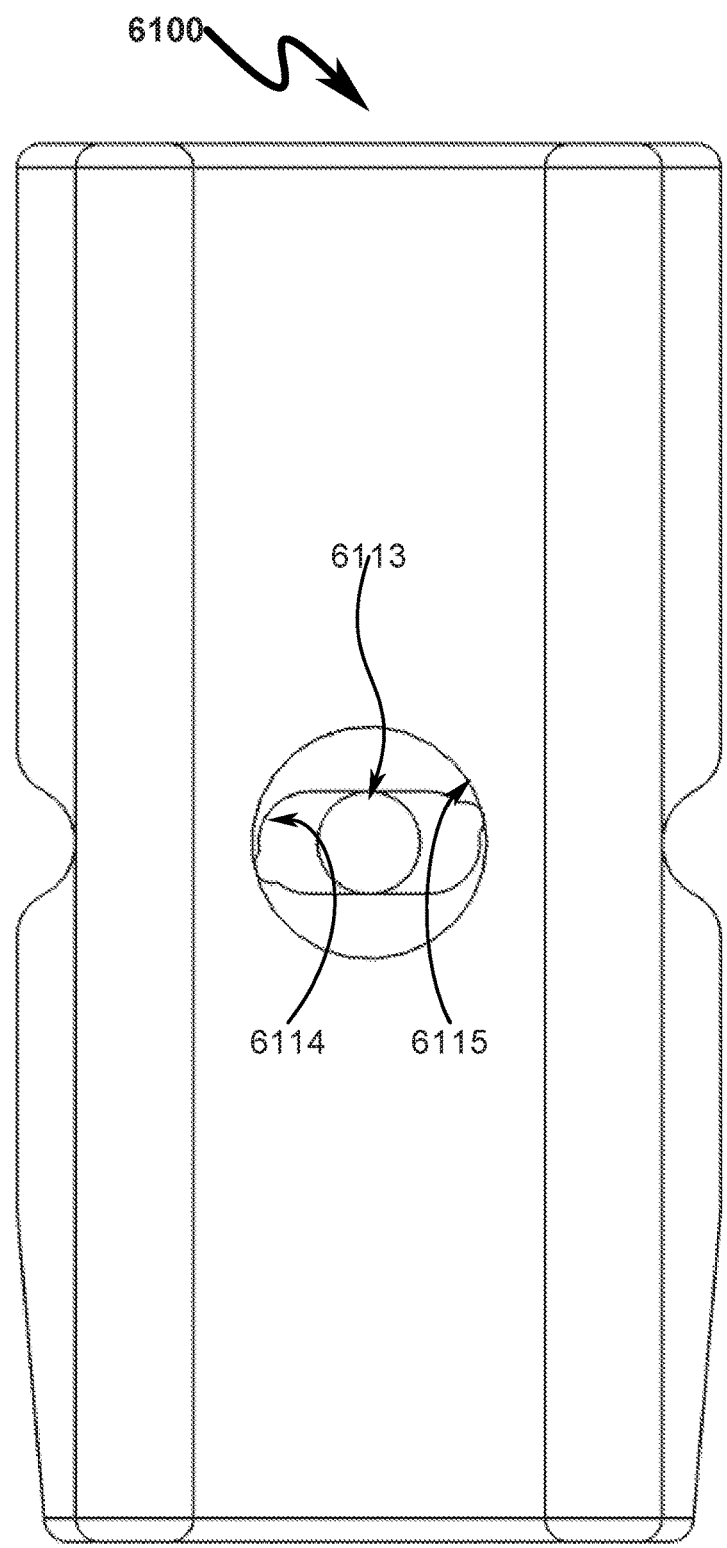
FIG. 61 illustrates a top view of a preferred exemplary invention rectangular cartridge SLC fixture embodiment.
Figure 62:
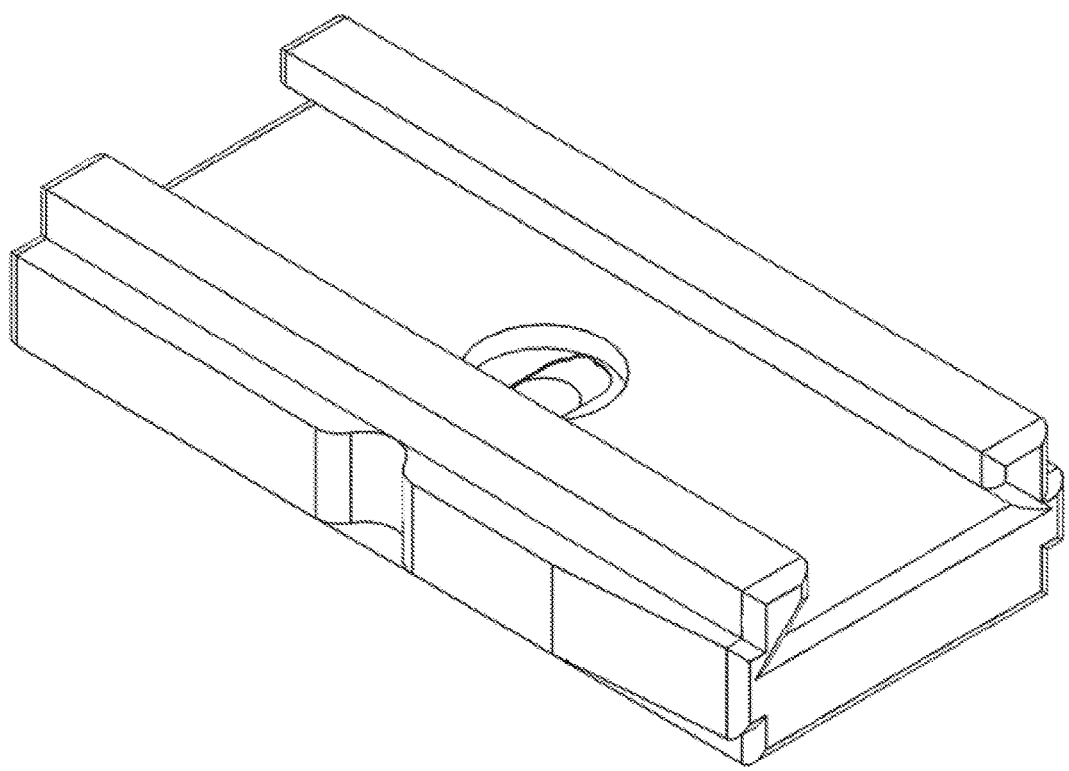
FIG. 62 illustrates a top right front perspective view of a preferred exemplary invention rectangular cartridge SLC fixture embodiment.
Figure 63:
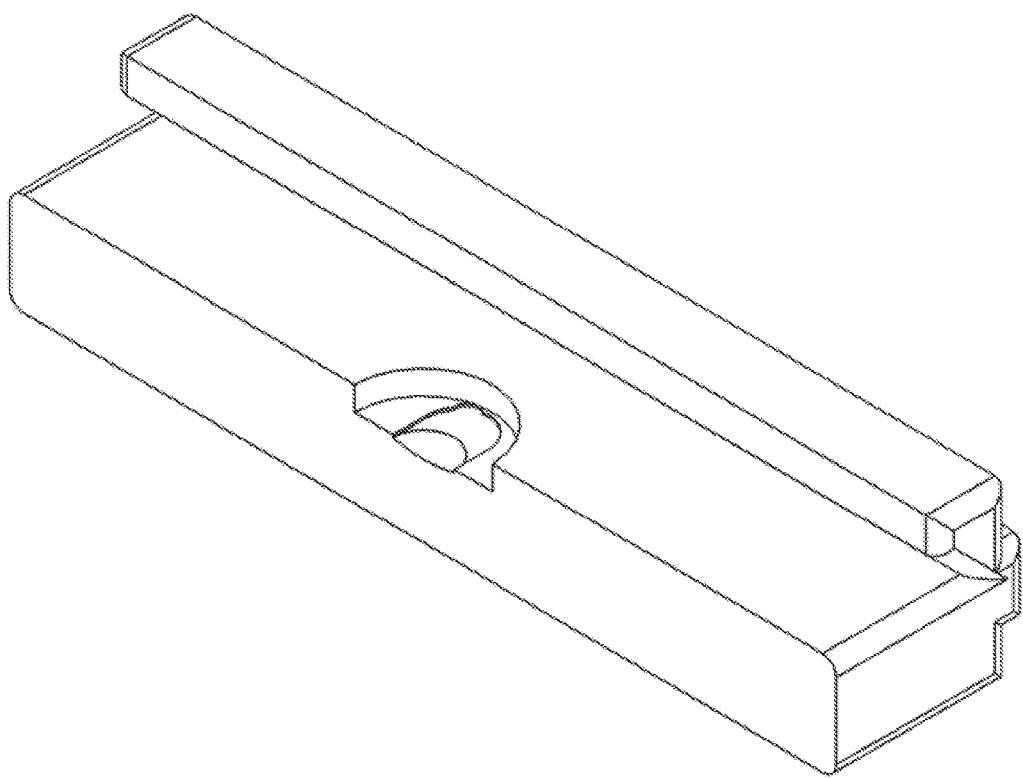
FIG. 63 illustrates top right front perspective front section views of a preferred exemplary invention rectangular cartridge SLC fixture embodiment.

Additional detail of the exemplary SLC and OLB can be seen by inspecting FIG. 57 (5700)-FIG. 64 (6400) in which the SLC carrier (5710) is depicted having one or more lens position identifier (LPI) (5711, 5812) features to ensure that the OLB (5720) is properly oriented and secured for laser irradiation when installed in the baseplate fixture (4101). The lens position identifier (LPI) (5711, 5812) features may include keys (5716, 5717) of differing widths on either side of the SLC carrier (5710) to permit defined alignment orientation of the SLC carrier (5710) with the baseplate fixture (4101). A lens cavity (5713, 6113) and corresponding haptic retainers (6114, 6115) are provided within the SLC carrier (5710) to secure the OLB (5720) lens (5723) and corresponding lens haptics (5724, 5725). A sliding retaining cover (5730) mates with the SLC carrier (5710) to hermetically seal the OLB (5720) within the lens cavity (5713) of the SLC carrier (5710). Dovetails (5738, 5739) or equivalent securing mechanisms in the sliding retaining cover (5730) ensure a hermetic seal of the sliding retaining cover (5730) to the SLC carrier (5710) when the sliding retaining cover (5730) is inserted within the corresponding recess of the SLC carrier (5710). A laser access window (5733) may be provided to allow laser radiation to be transmitted to the OLB (5720) for customization. If laser radiation is to be directed through the sliding retaining cover (5730), the sliding retaining cover (5730) will be constructed of material having a refractive index in the range of 1.05 to 1.65.

A sealing lid (5740) is provided to seal the SLC (5710) and permit the SLC (5710)/OLB (5720) combination to be sterilized after assembly. This sealing lid (5740) may also serve as a dust cover for the sliding retaining cover (5730) and/or laser access window (5733). In this configuration the sealing lid (5740) may be configured to transmit laser radiation through to the liquid covering the OLB (5720) or in some circumstances the sealing lid (5740) may be removed prior to customization in which case the laser radiation is directly impinges the sliding retaining cover (5730) and then impinges the OLB (5720) to affect refractive index changes in the OLB (5720) to generate a custom lens structure. If laser radiation is to be directed through the sealing lid (5740), the sealing lid (5740) will be constructed of material having a refractive index in the range of 1.05 to 1.65.

Figure 48:
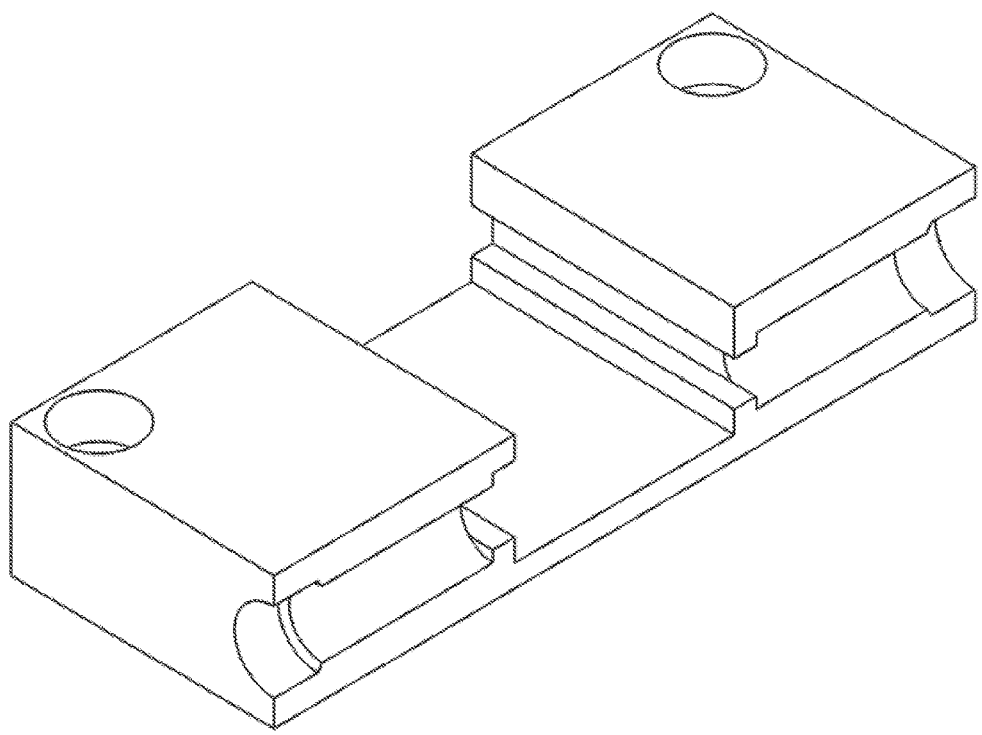
FIG. 48 illustrates a top right front perspective right section view of a preferred exemplary invention rectangular cartridge SLC fixture embodiment with generic ophthalmic lens blank (OLB) removed.
Figure 49:
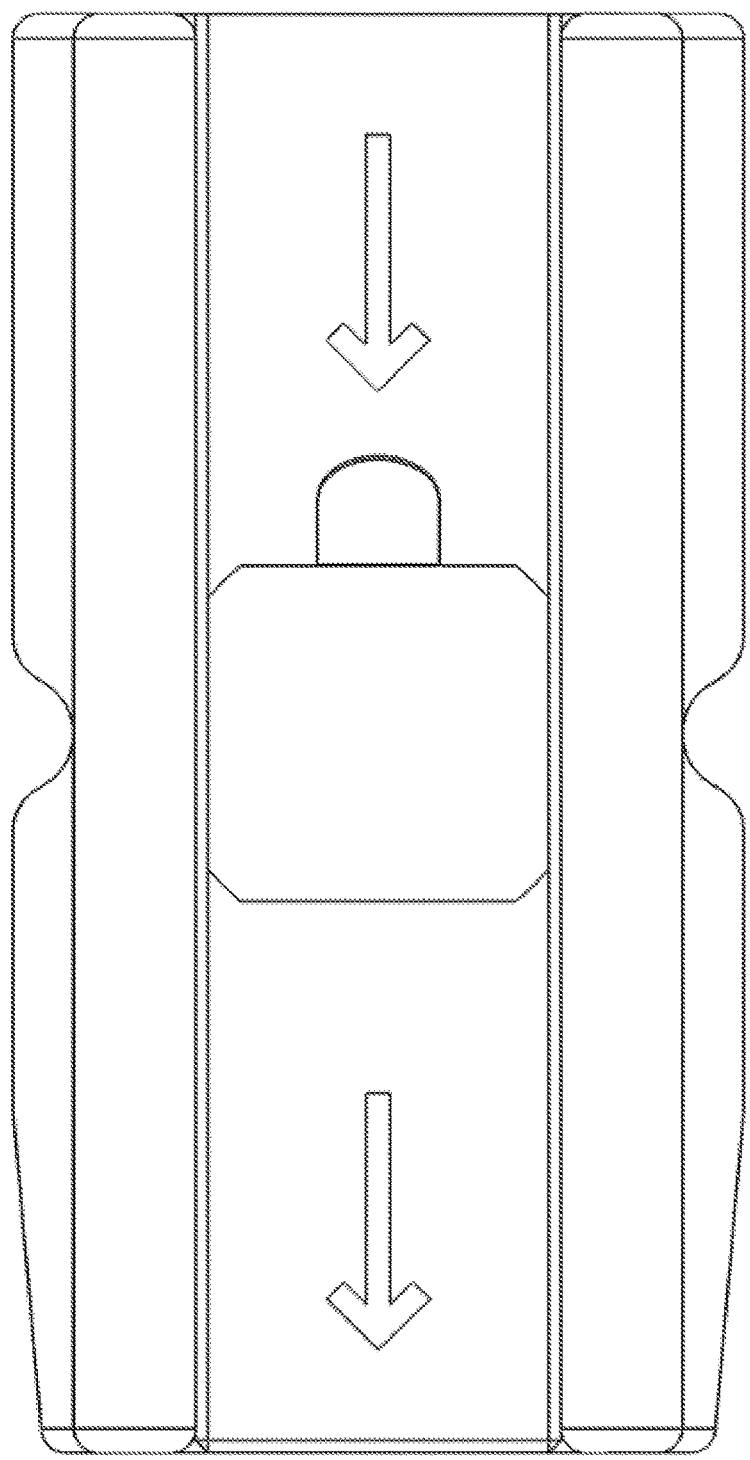
FIG. 49 illustrates a top view of a preferred exemplary invention rectangular cartridge SLC ophthalmic lens blank (OLB) embodiment with hermetic seal installed.
Figure 50:
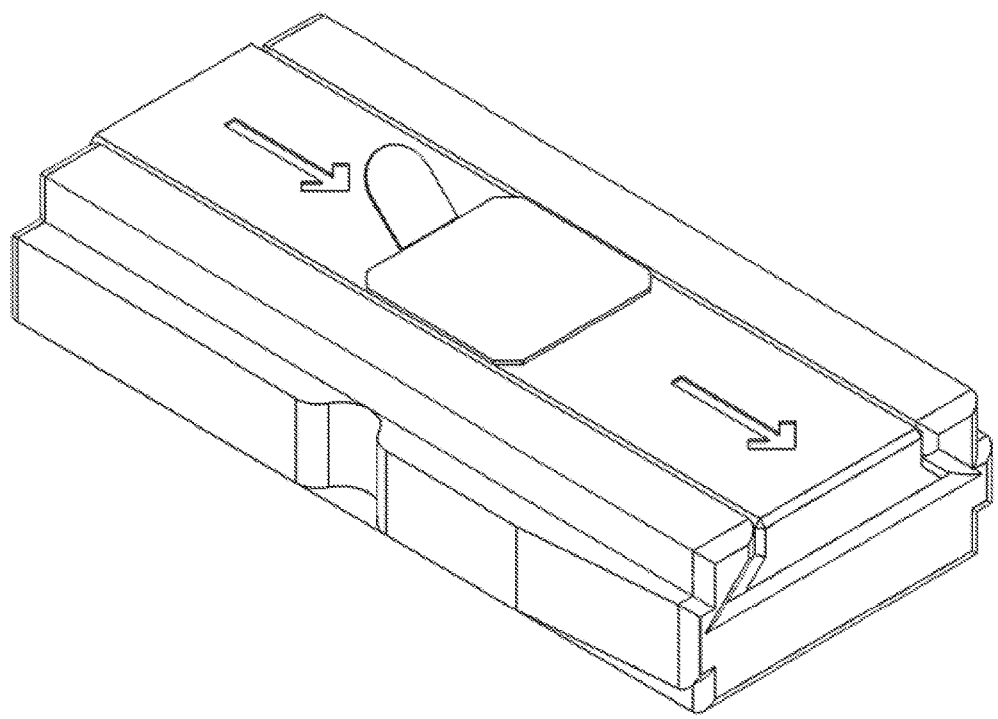
FIG. 50 illustrates a top right front perspective view of a preferred exemplary invention rectangular cartridge SLC ophthalmic lens blank (OLB) embodiment with hermetic seal installed.
Figure 51:
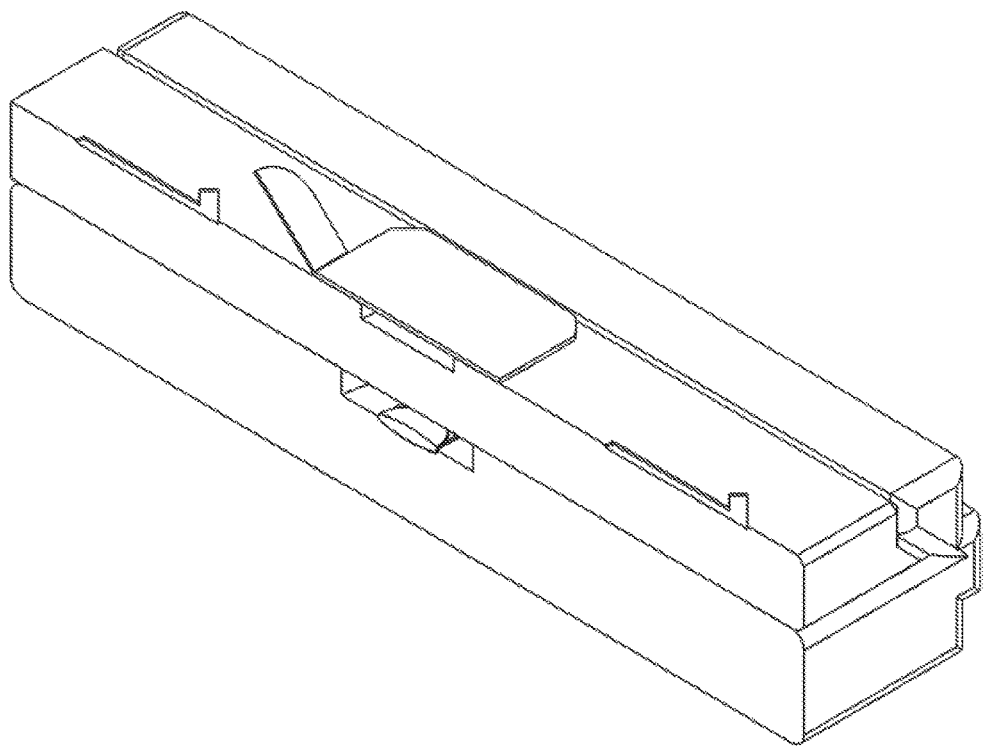
FIG. 51 illustrates a top right front perspective front section view of a preferred exemplary invention rectangular cartridge SLC ophthalmic lens blank (OLB) embodiment with hermetic seal installed.
Figure 52:
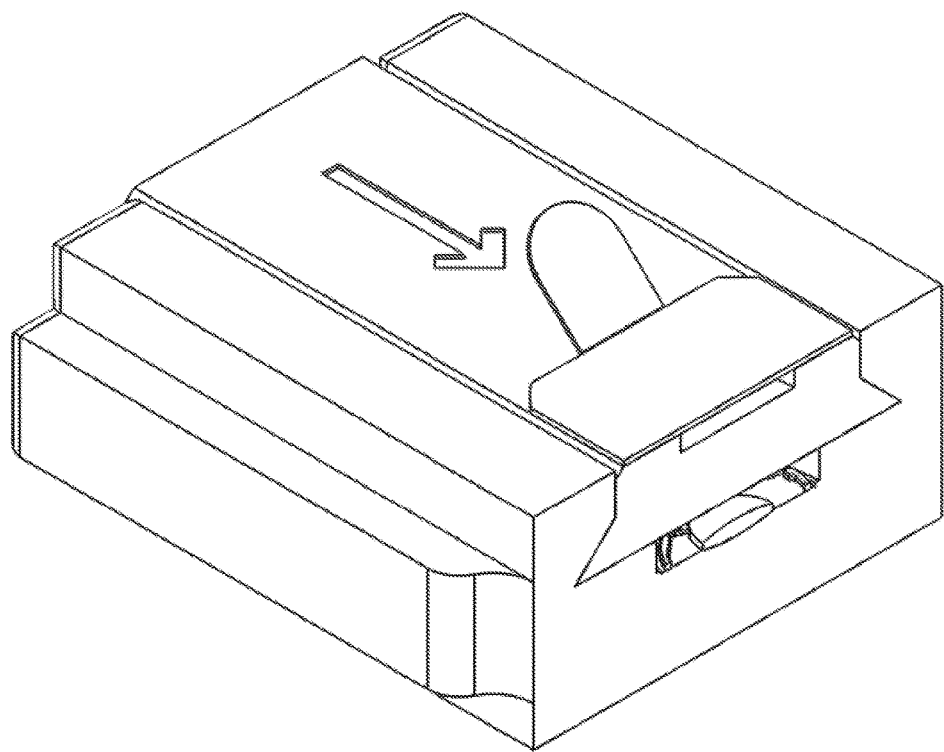
FIG. 52 illustrates a top right front perspective right section view of a preferred exemplary invention rectangular cartridge SLC ophthalmic lens blank (OLB) embodiment with hermetic seal, installed.
Figure 53:
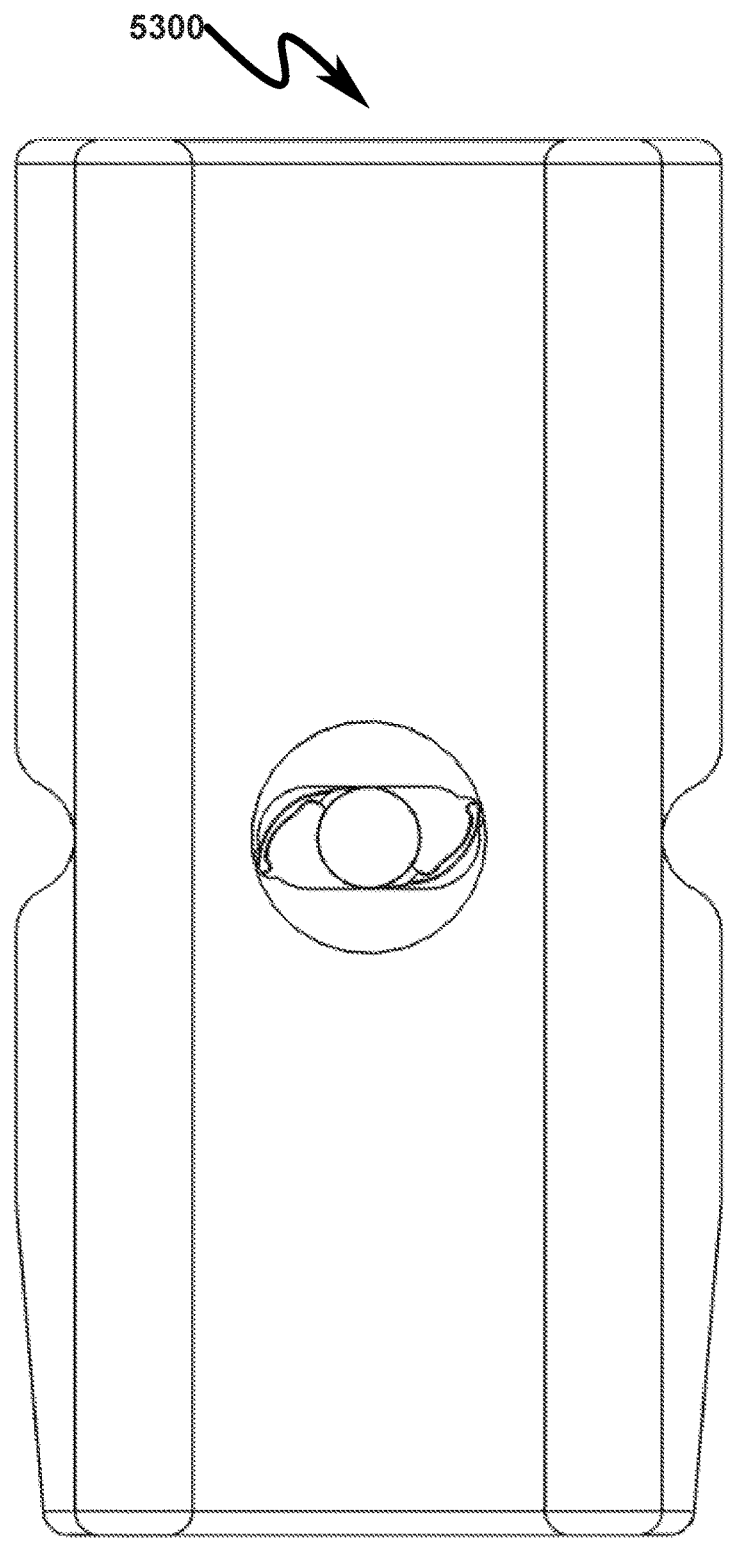
FIG. 53 illustrates a top view of a preferred exemplary invention rectangular cartridge SLC ophthalmic lens blank (OLB) embodiment with hermetic seal removed.
Figure 54:
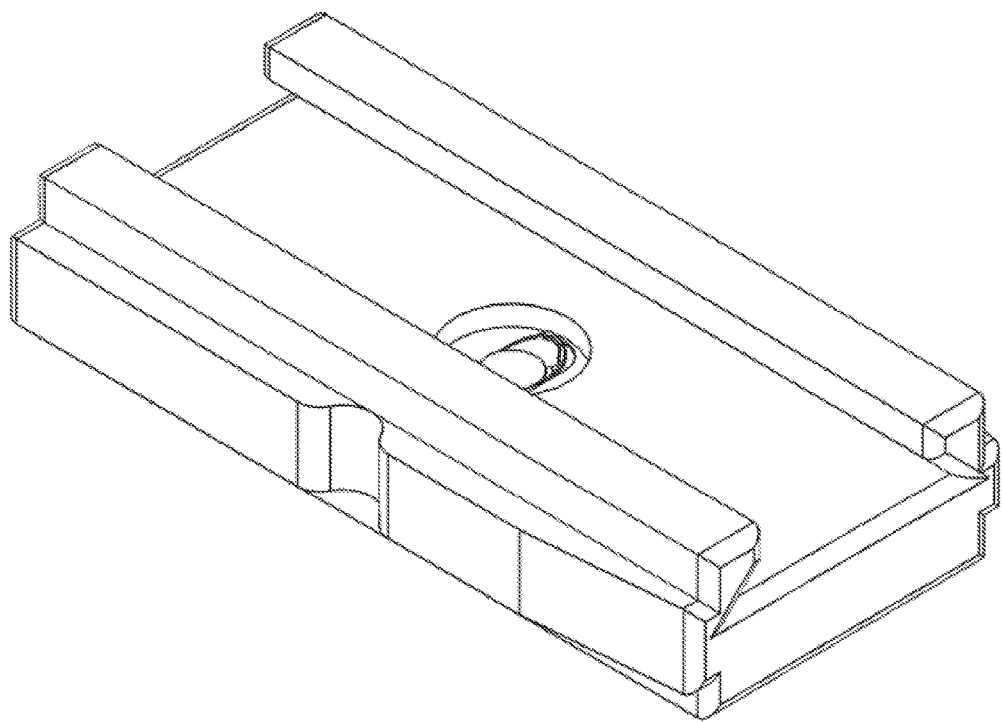
FIG. 54 illustrates a top right front perspective view of a preferred exemplary invention rectangular cartridge SLC ophthalmic lens blank (OLB) embodiment with hermetic seal removed.
Figure 55:
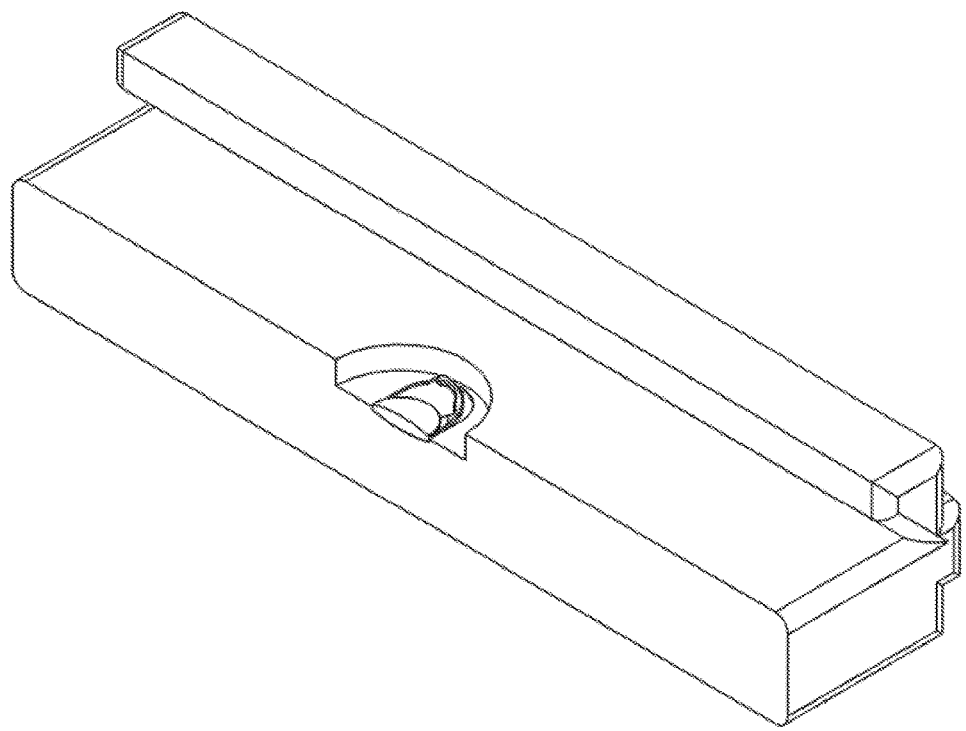
FIG. 55 illustrates a top right front perspective front section view of a preferred exemplary invention rectangular cartridge SLC ophthalmic lens blank (OLB) embodiment with hermetic seal removed.

As generally depicted in FIG. 41 (4100)-FIG. 48 (4800), the SLC may be securely captured and registered within the baseplate fixture via the use of spring loaded pins positioned within the baseplate fixture that mate with corresponding detents in the SLC fixture as it slides into the baseplate fixture. Note the examples shown provide tapered insertion on one end of the SLC to ensure that the mating spring/pin combinations can be depressed sufficiently to allow secure mating of the SLC and baseplate when the two are coupled together via sliding insertion of the SLC into the baseplate frame.

Exemplary Cylindrical Cartridge SLC Embodiment (6500)-(9600)

Figure 65:
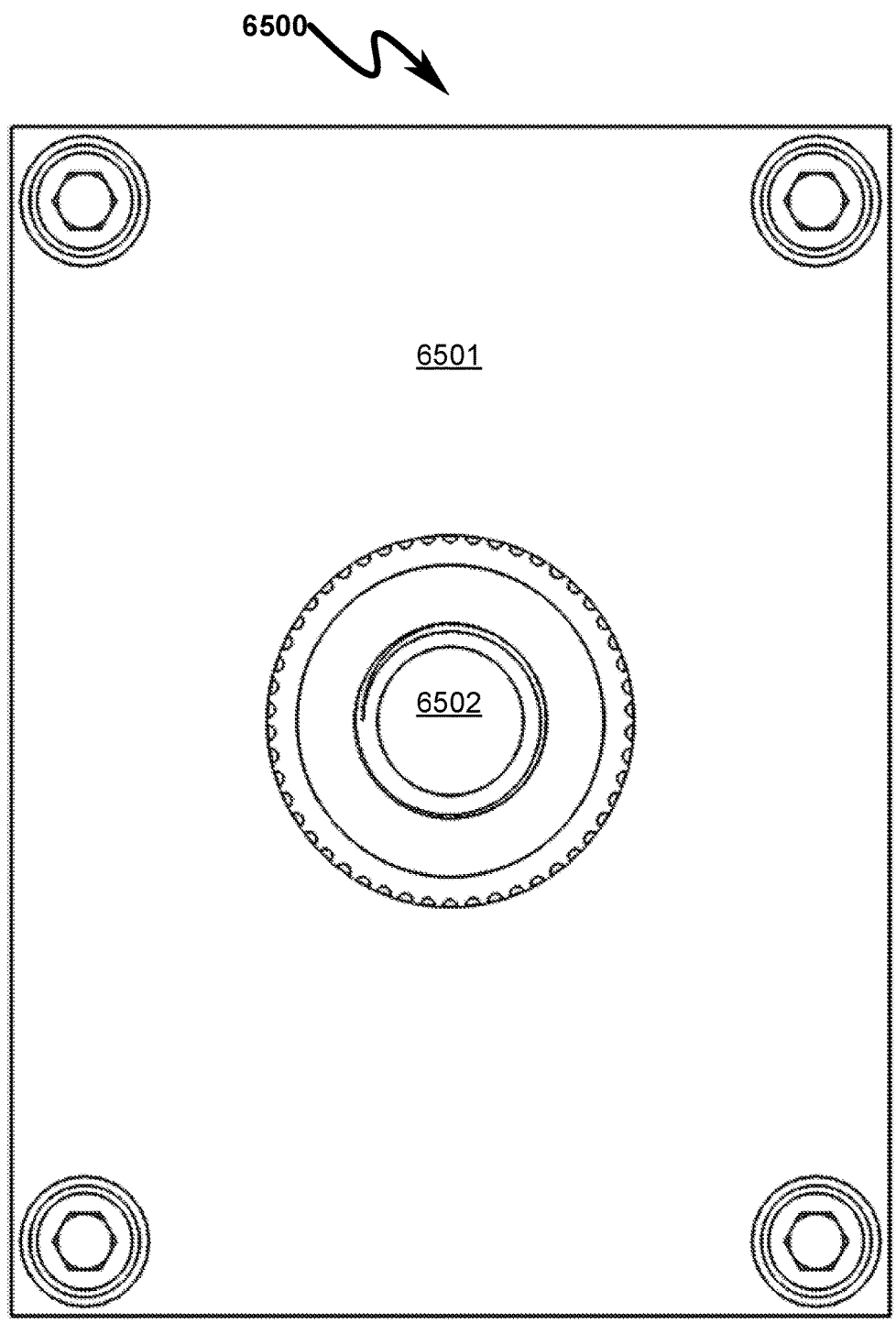
FIG. 65 illustrates a top view of a preferred exemplary invention cylindrical cartridge SLC fixture embodiment with generic ophthalmic lens blank (OLB) installed.
Figure 66:
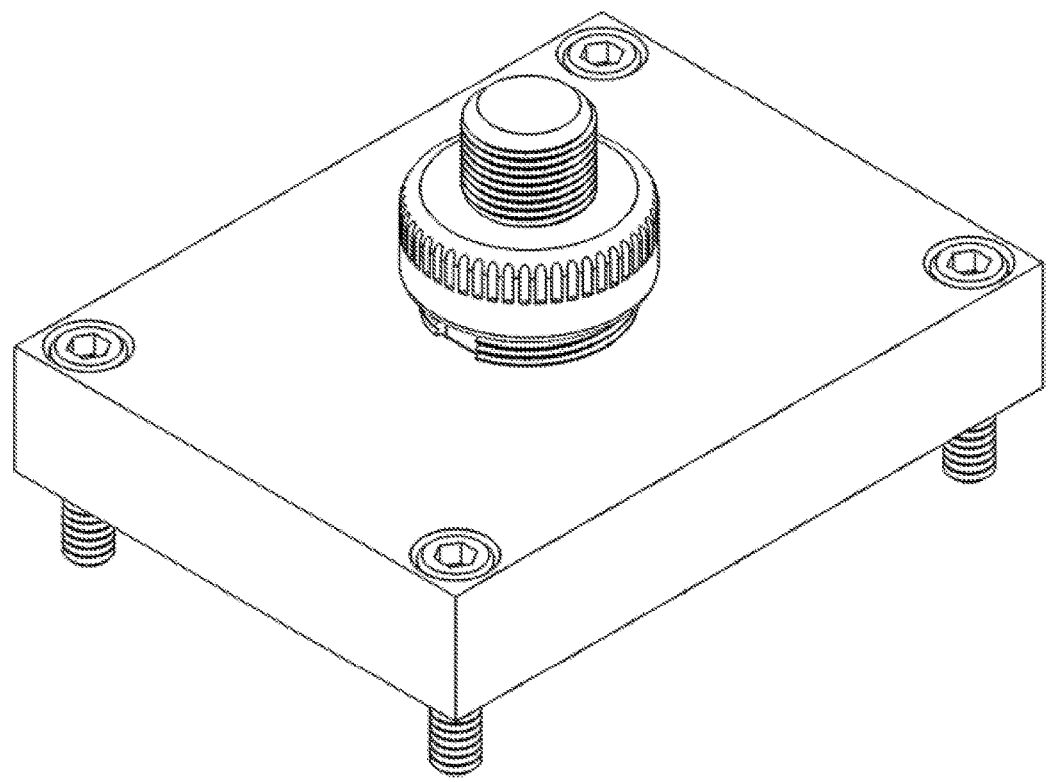
FIG. 66 illustrates a top right front perspective view of a preferred exemplary invention cylindrical cartridge SLC fixture embodiment with generic ophthalmic lens blank (OLB) installed.
Figure 67:
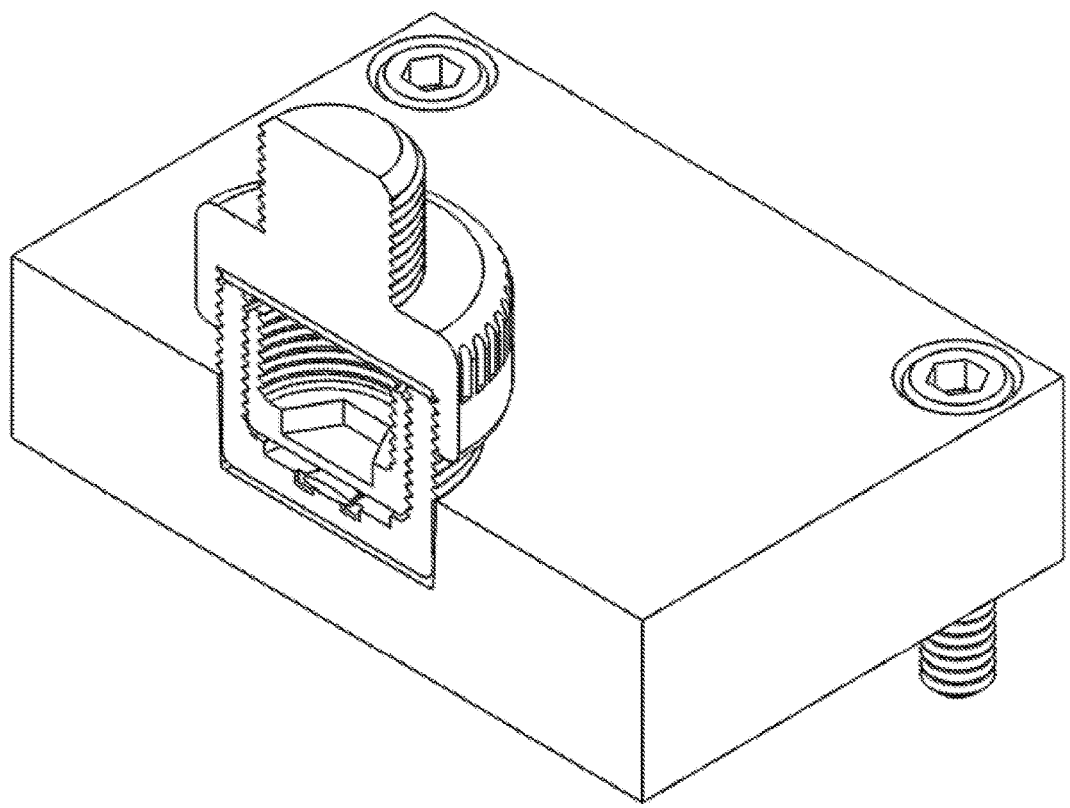
FIG. 67 illustrates a top right front perspective front section view of a preferred exemplary invention cylindrical cartridge SLC fixture embodiment with generic ophthalmic lens blank (OLB) installed.
Figure 68:
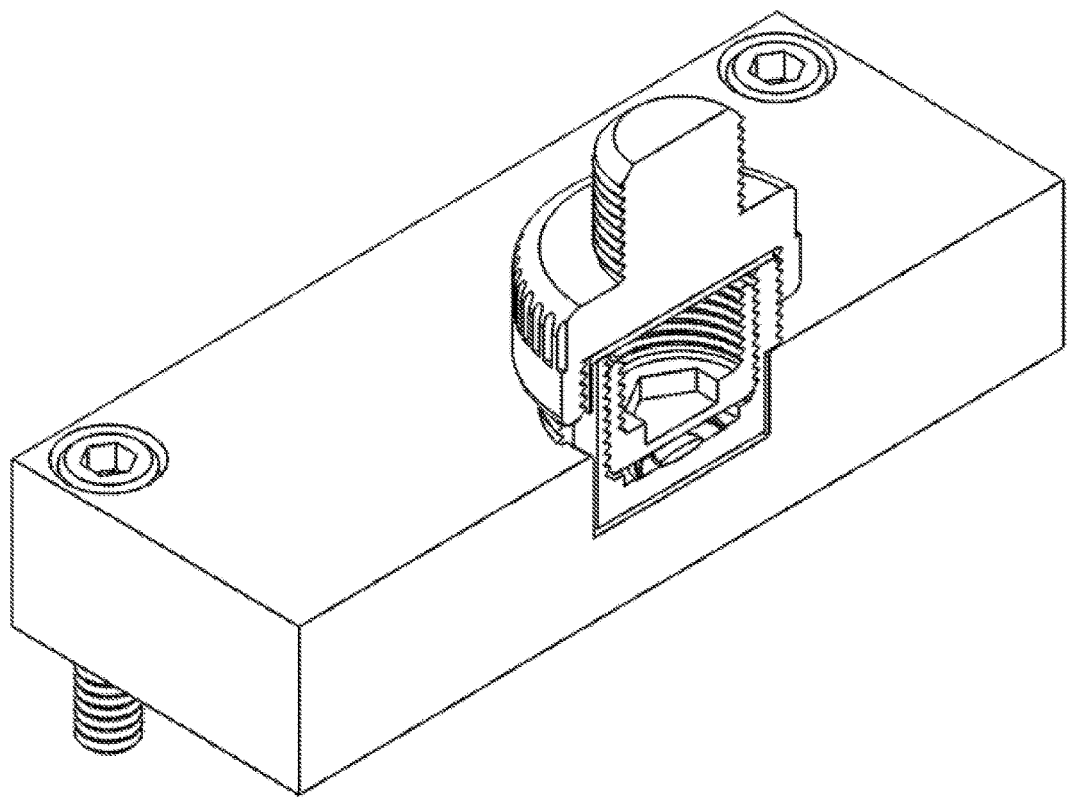
FIG. 68 illustrates a top right front perspective right section view of a preferred exemplary invention cylindrical cartridge SLC fixture embodiment with generic ophthalmic lens blank (OLB) installed.
Figure 69:
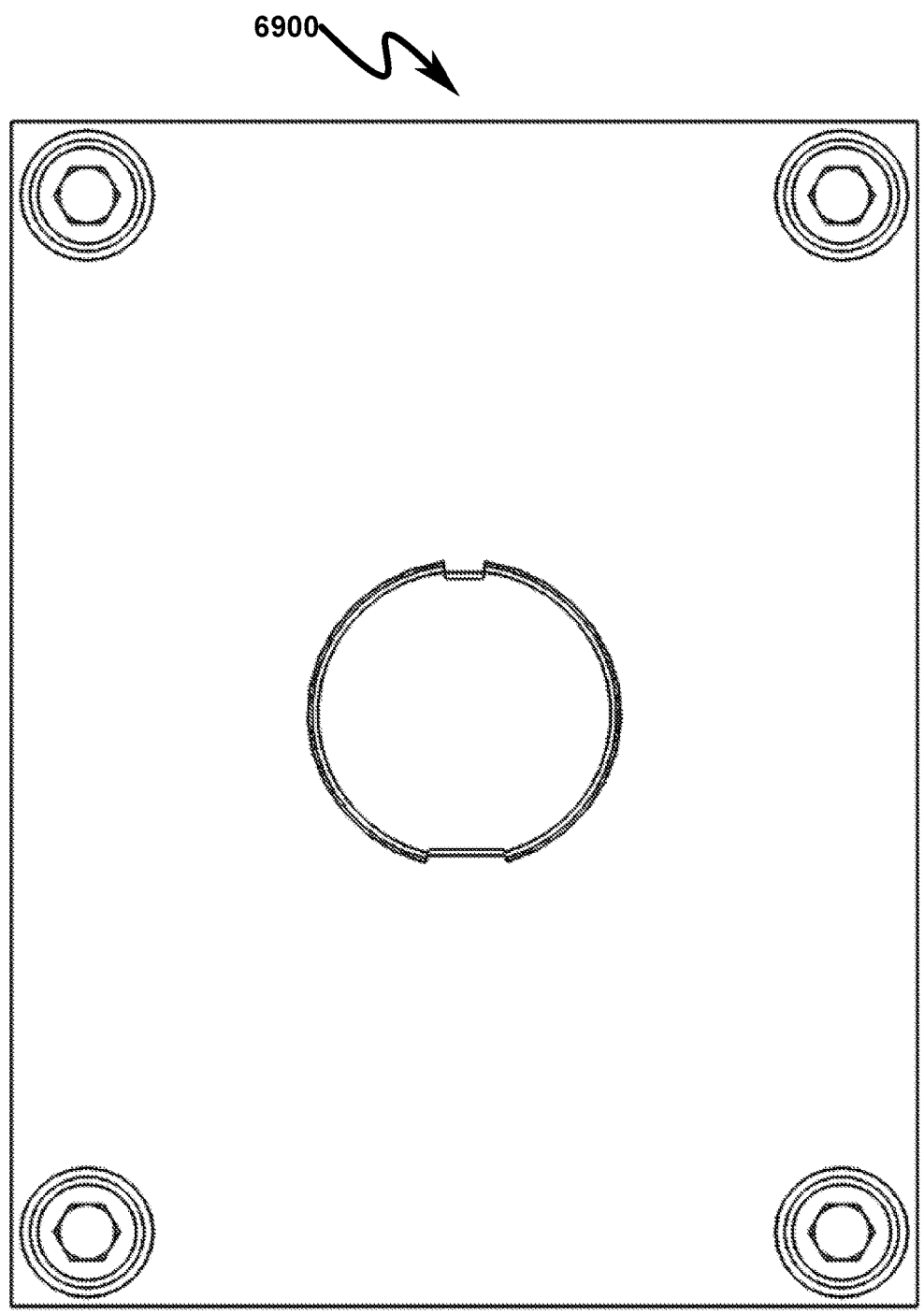
Figure 70:
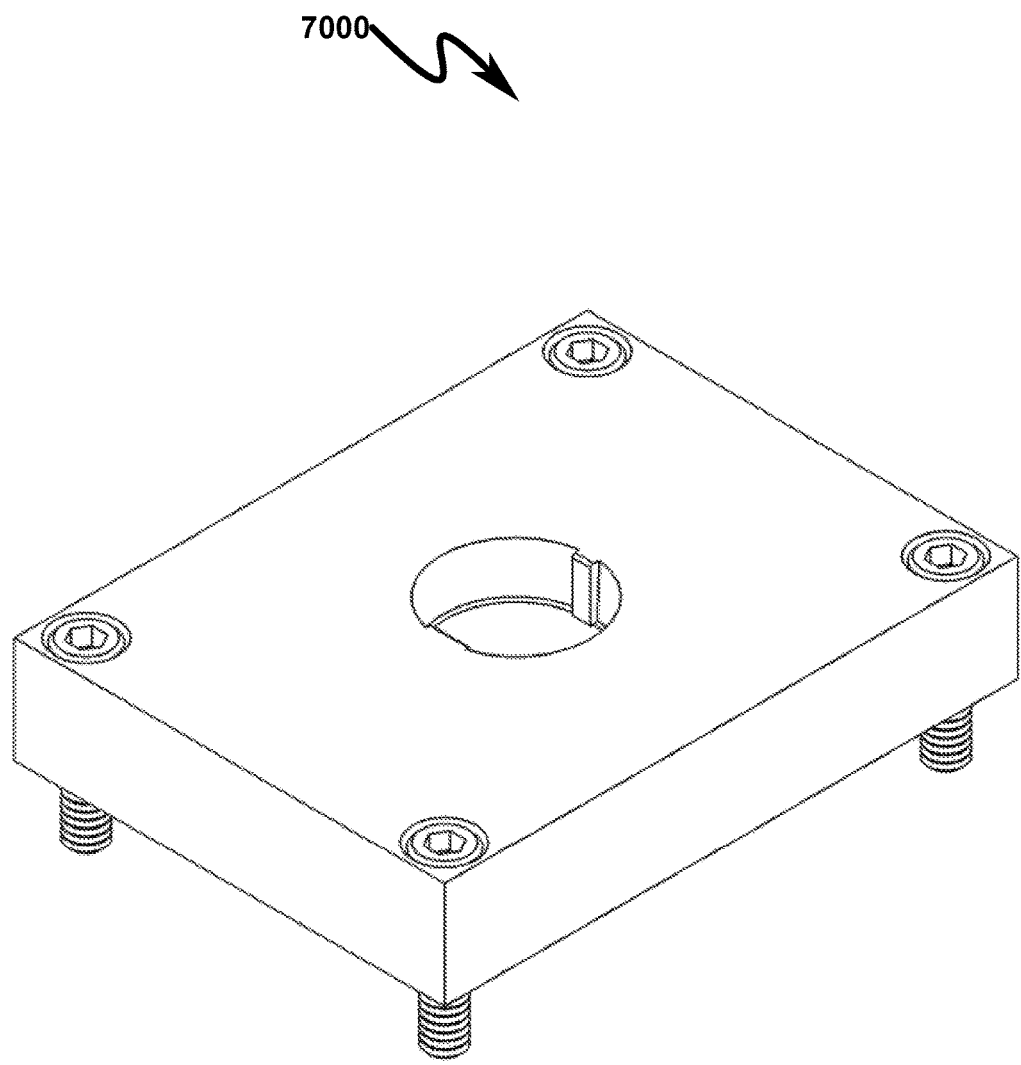
FIG. 70 illustrates a top right front perspective view of a preferred exemplary invention cylindrical cartridge SLC fixture embodiment with generic ophthalmic lens blank (OLB) removed.
Figure 71:
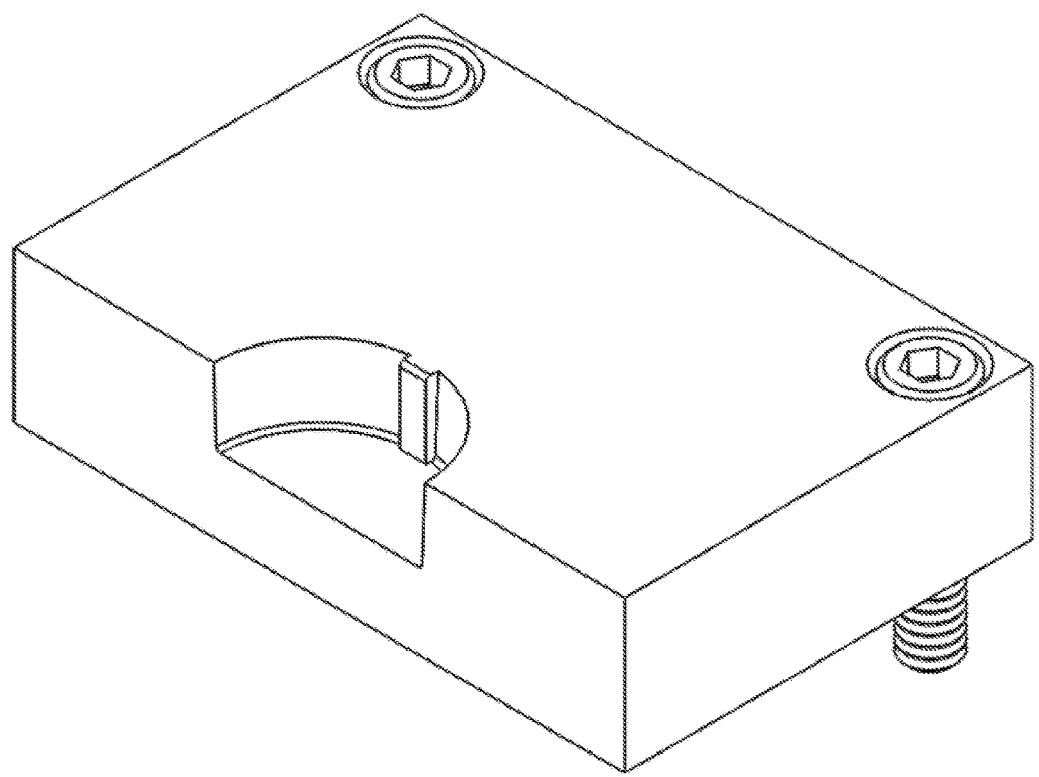
FIG. 71 illustrates a top right front perspective front section view of a preferred exemplary invention cylindrical cartridge SLC fixture embodiment with generic ophthalmic lens blank (OLB) removed.
Figure 72:
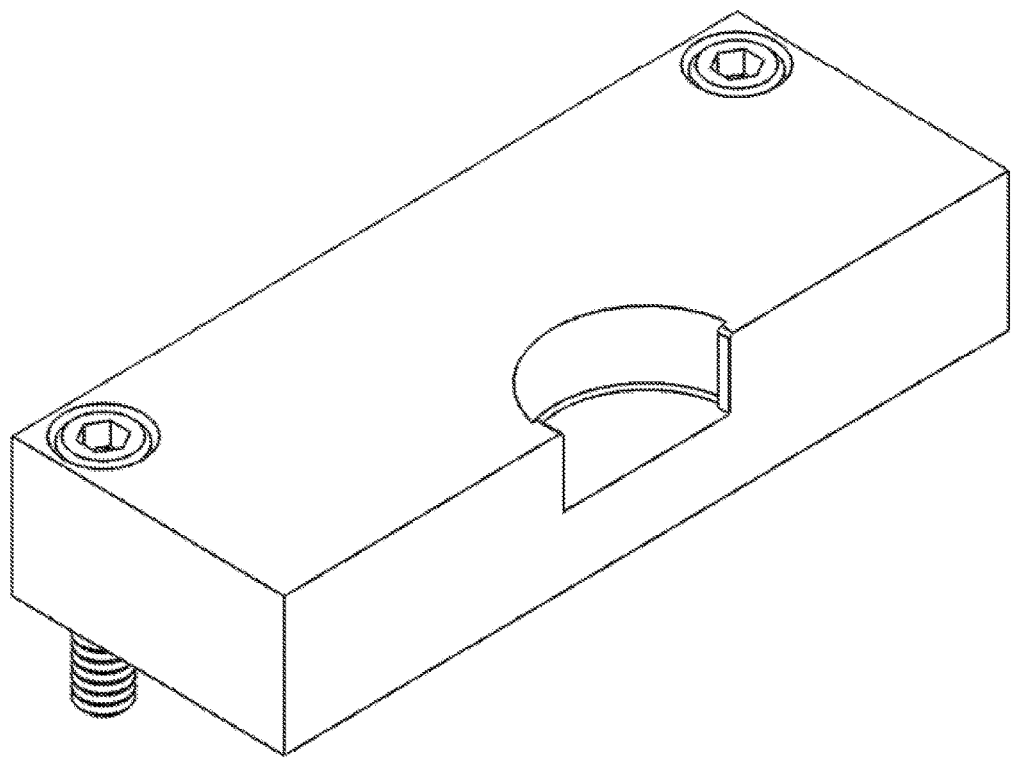
FIG. 72 illustrates a top right front perspective right section view of a preferred exemplary invention cylindrical cartridge SLC fixture embodiment with generic ophthalmic lens blank (OLB) removed.
Figure 73:
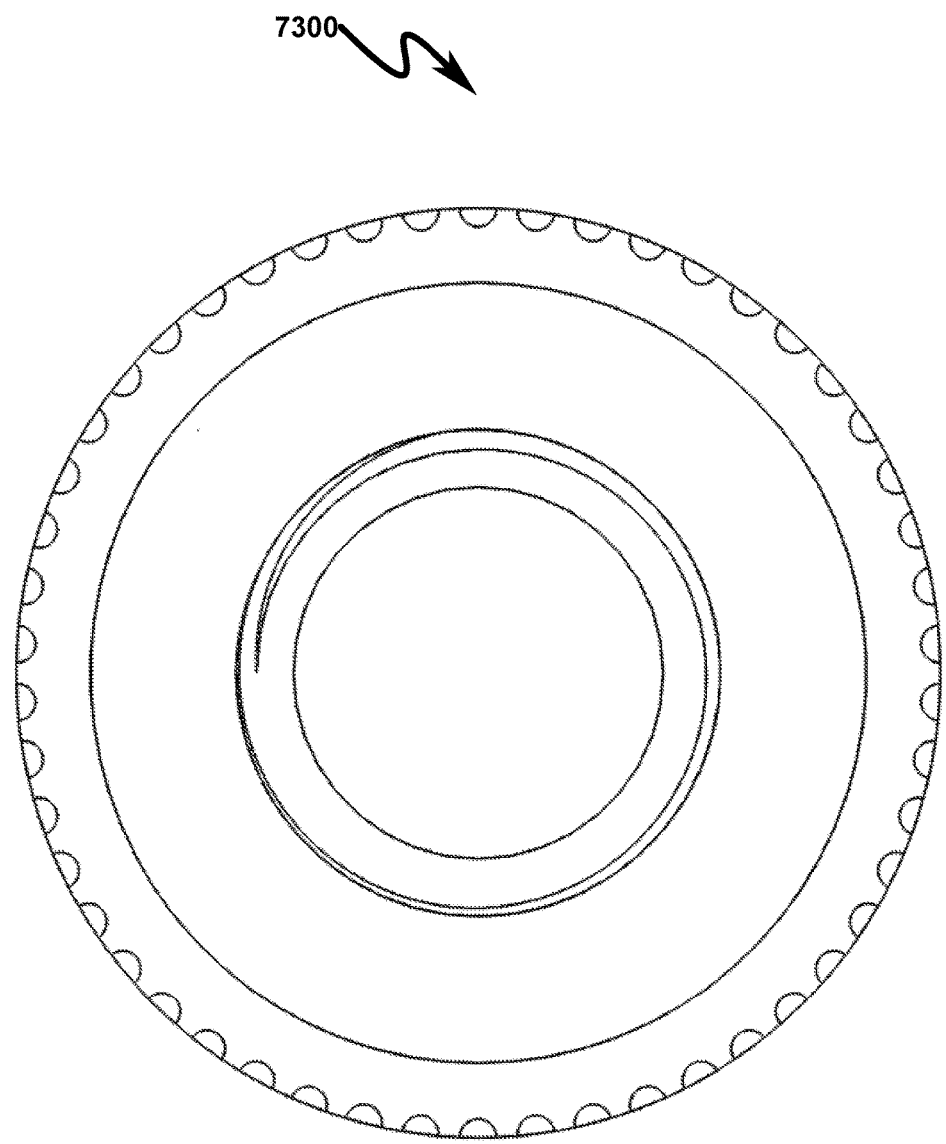
FIG. 73 illustrates a top view of a preferred exemplary invention cylindrical cartridge SLC ophthalmic lens blank (OLB) embodiment with hermetic seal installed.
Figure 74:
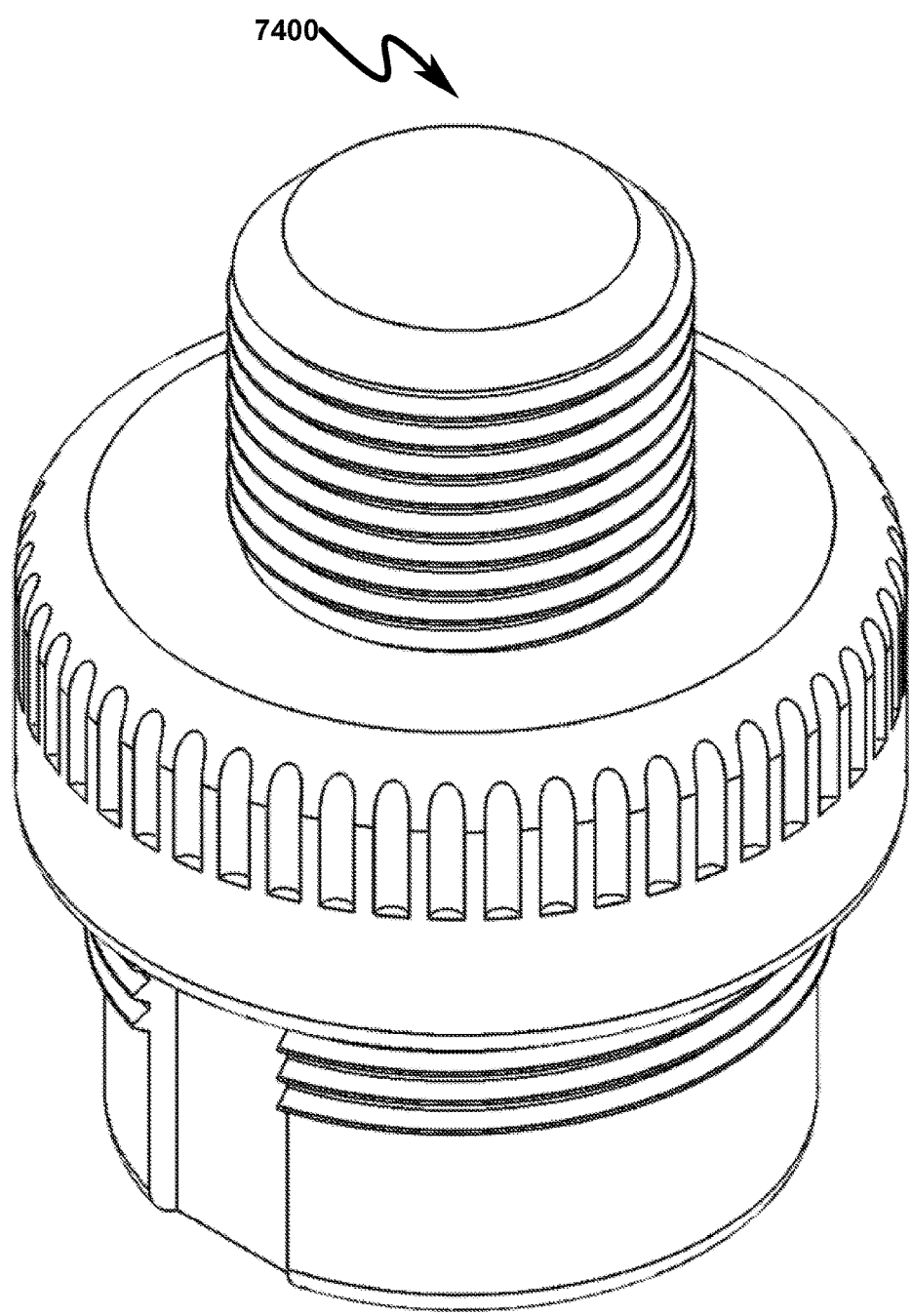
FIG. 74 illustrates a top right front perspective view of a preferred exemplary invention cylindrical cartridge SLC ophthalmic lens blank (OLB) embodiment with hermetic seal installed.
Figure 75:
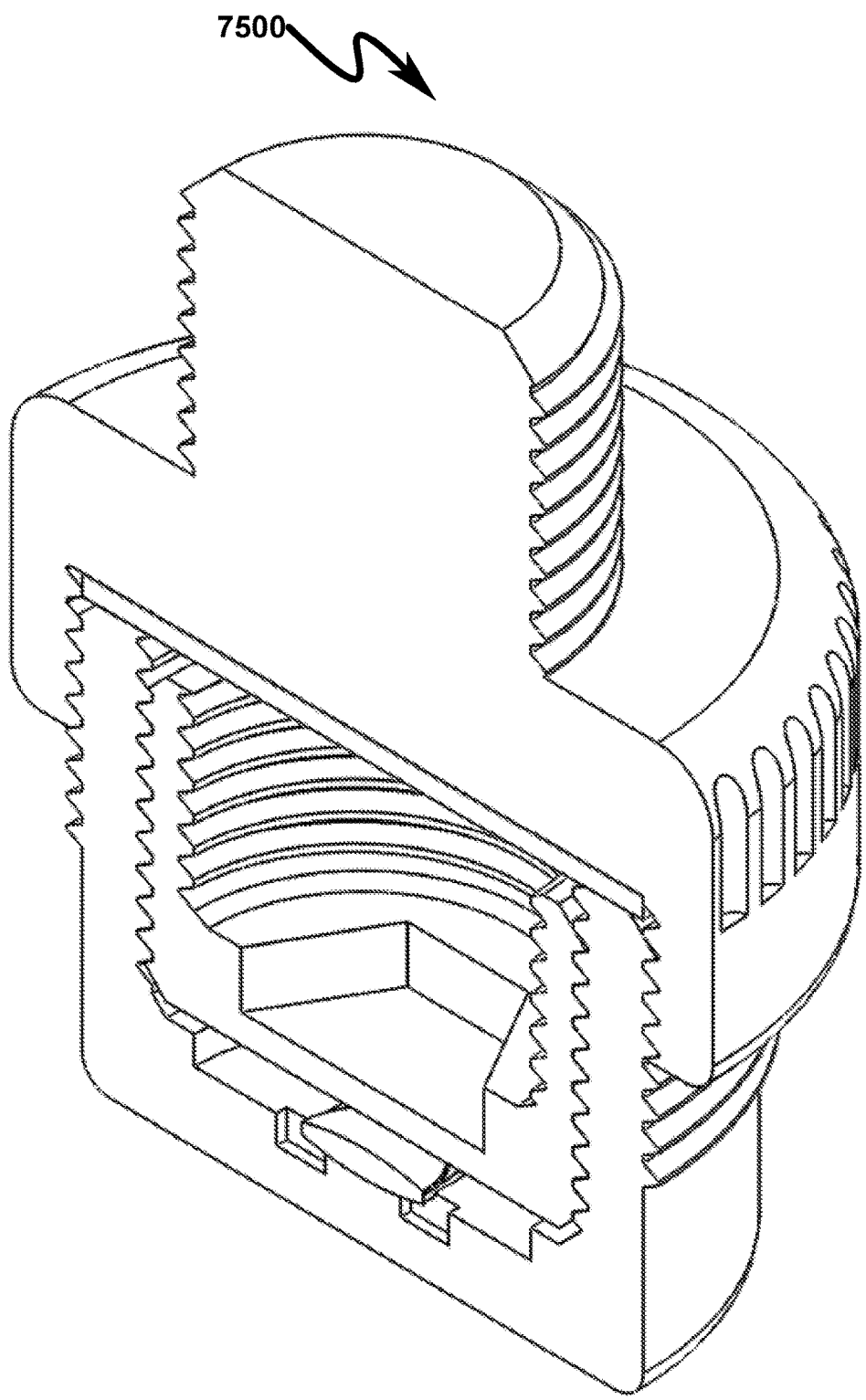
FIG. 75 illustrates a top right front perspective front section view of a preferred exemplary invention cylindrical cartridge SLC ophthalmic lens blank (OLB) embodiment with hermetic seal installed.
Figure 76:
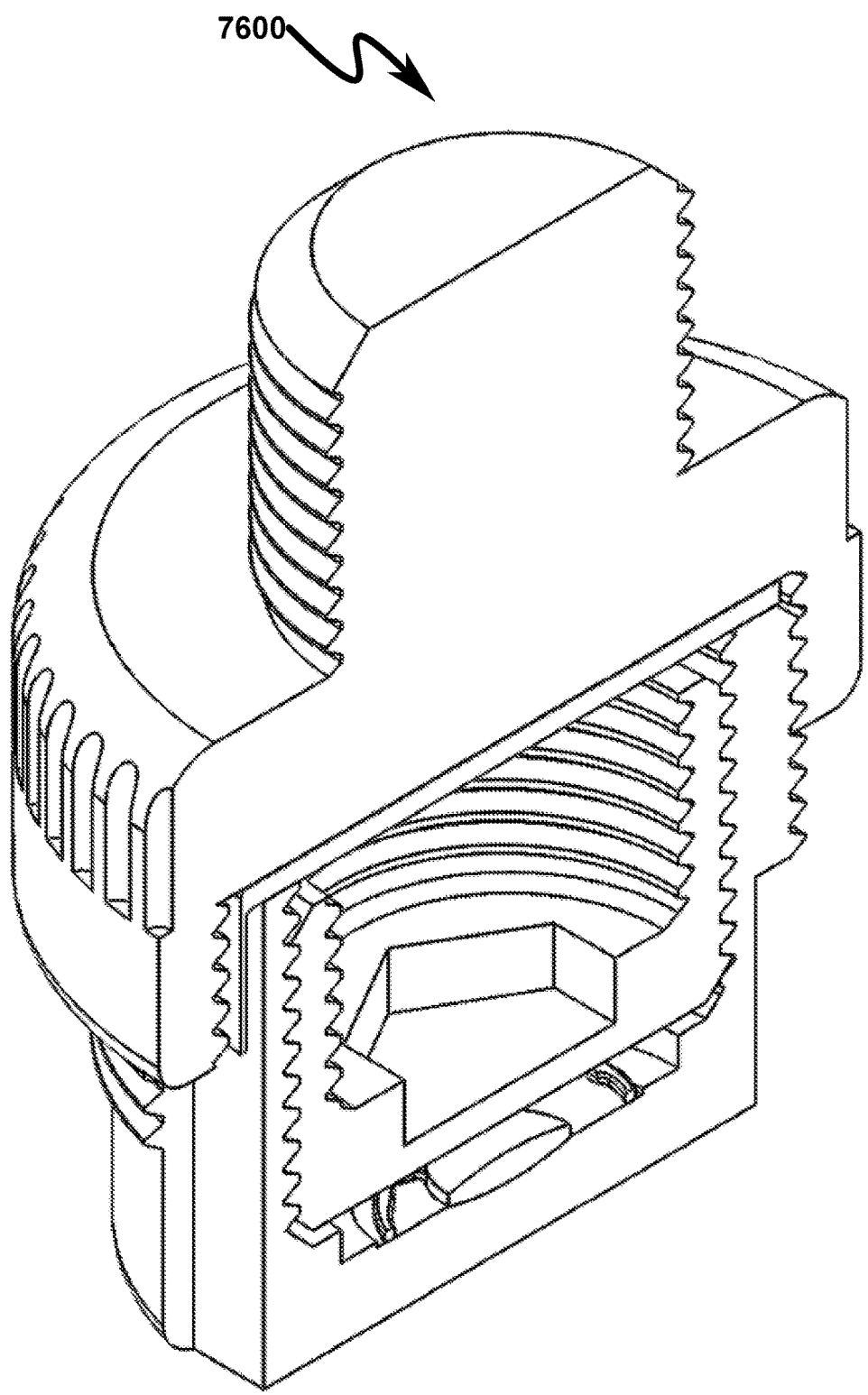
FIG. 76 illustrates a top right front perspective right section view of a preferred exemplary invention cylindrical cartridge SLC ophthalmic lens blank (OLB) embodiment with hermetic seal installed.
Figure 77:
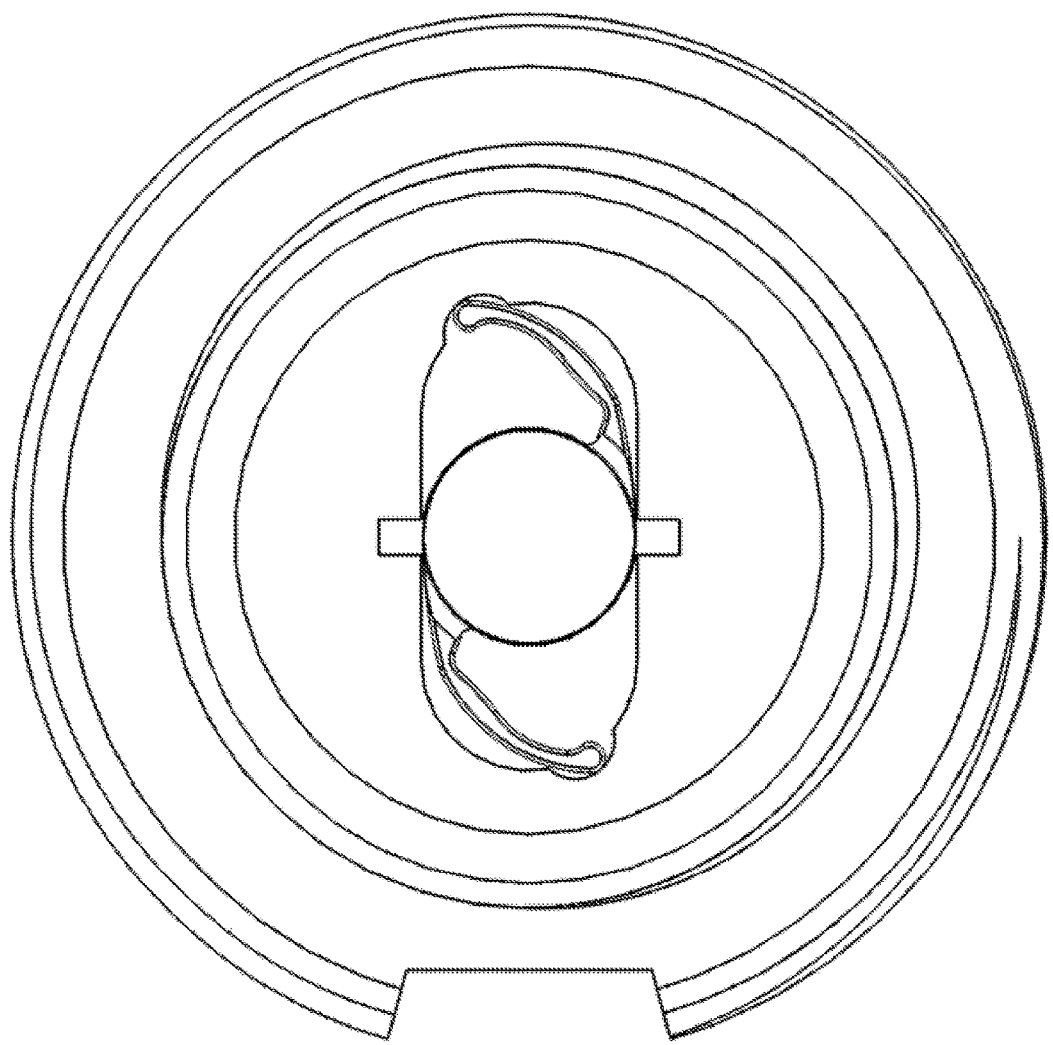
FIG. 77 illustrates a top view of a preferred exemplary invention cylindrical cartridge SLC ophthalmic lens blank (OLB) embodiment with hermetic seal removed.
Figure 78:
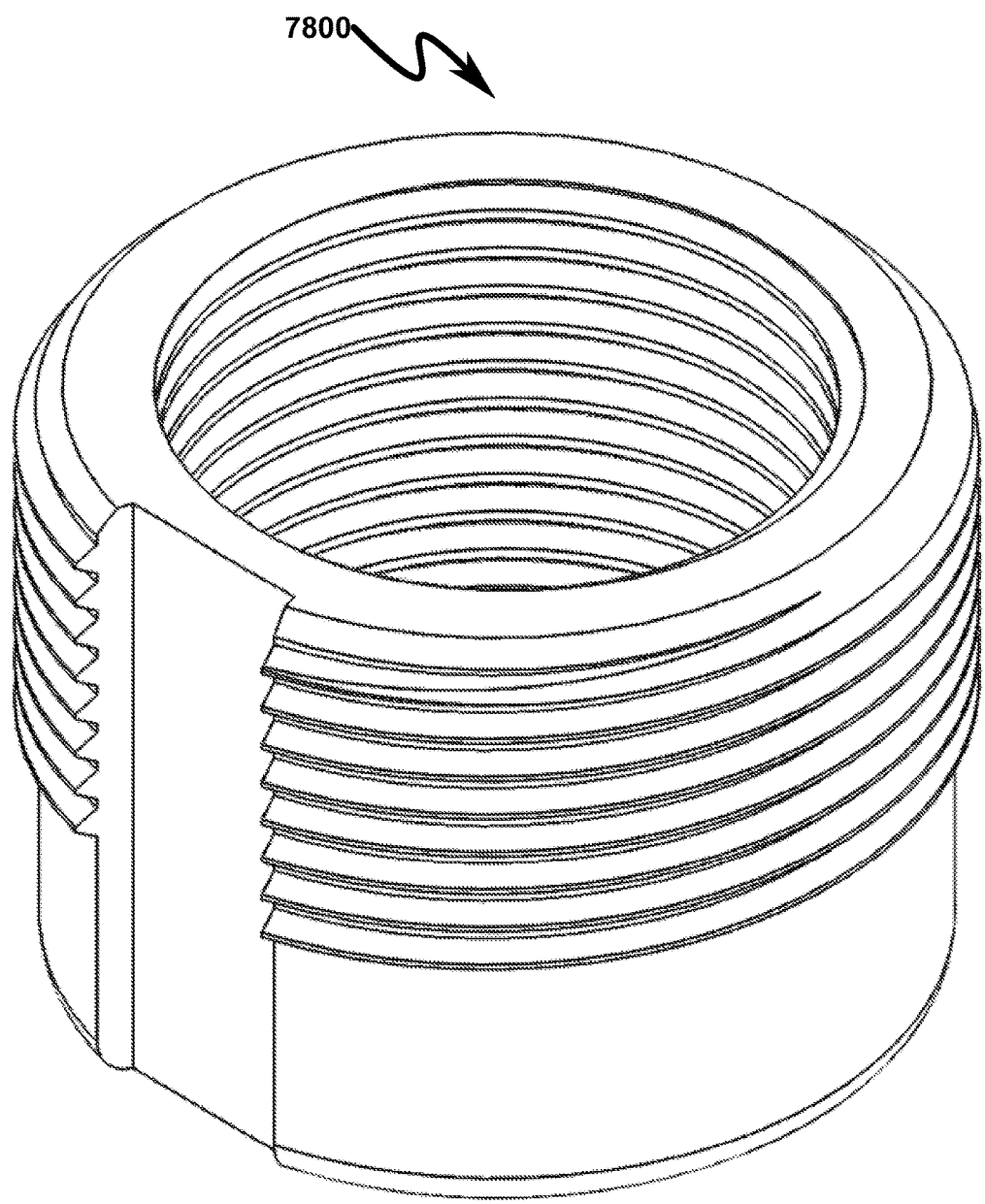
FIG. 78 illustrates a top right front perspective view of a preferred exemplary invention cylindrical cartridge SLC ophthalmic lens blank (OLB) embodiment with hermetic seal removed.
Figure 79:
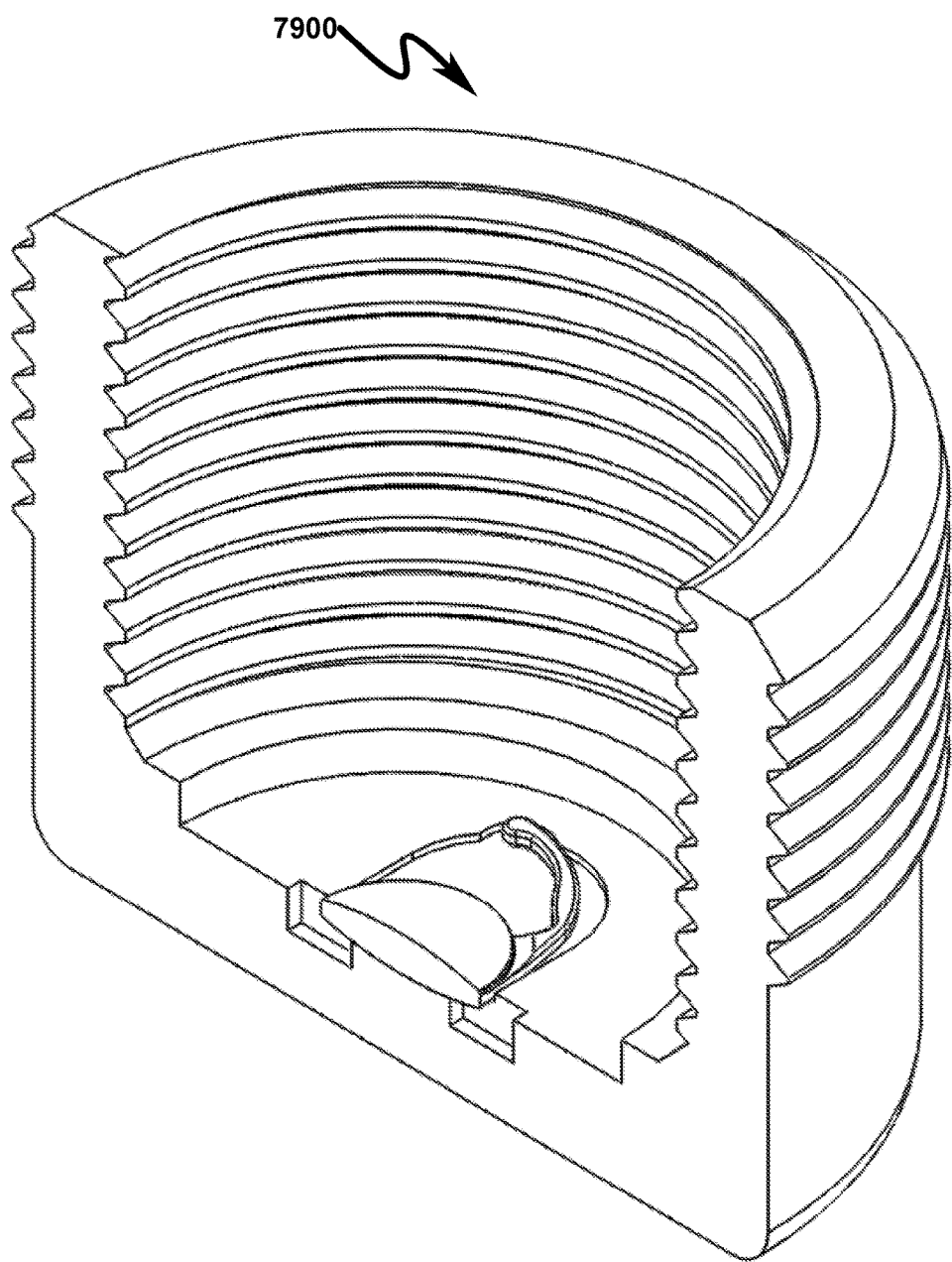
FIG. 79 illustrates a top right front perspective front section view of a preferred exemplary invention cylindrical cartridge SLC ophthalmic lens blank (OLB) embodiment with hermetic seal removed.
Figure 80:
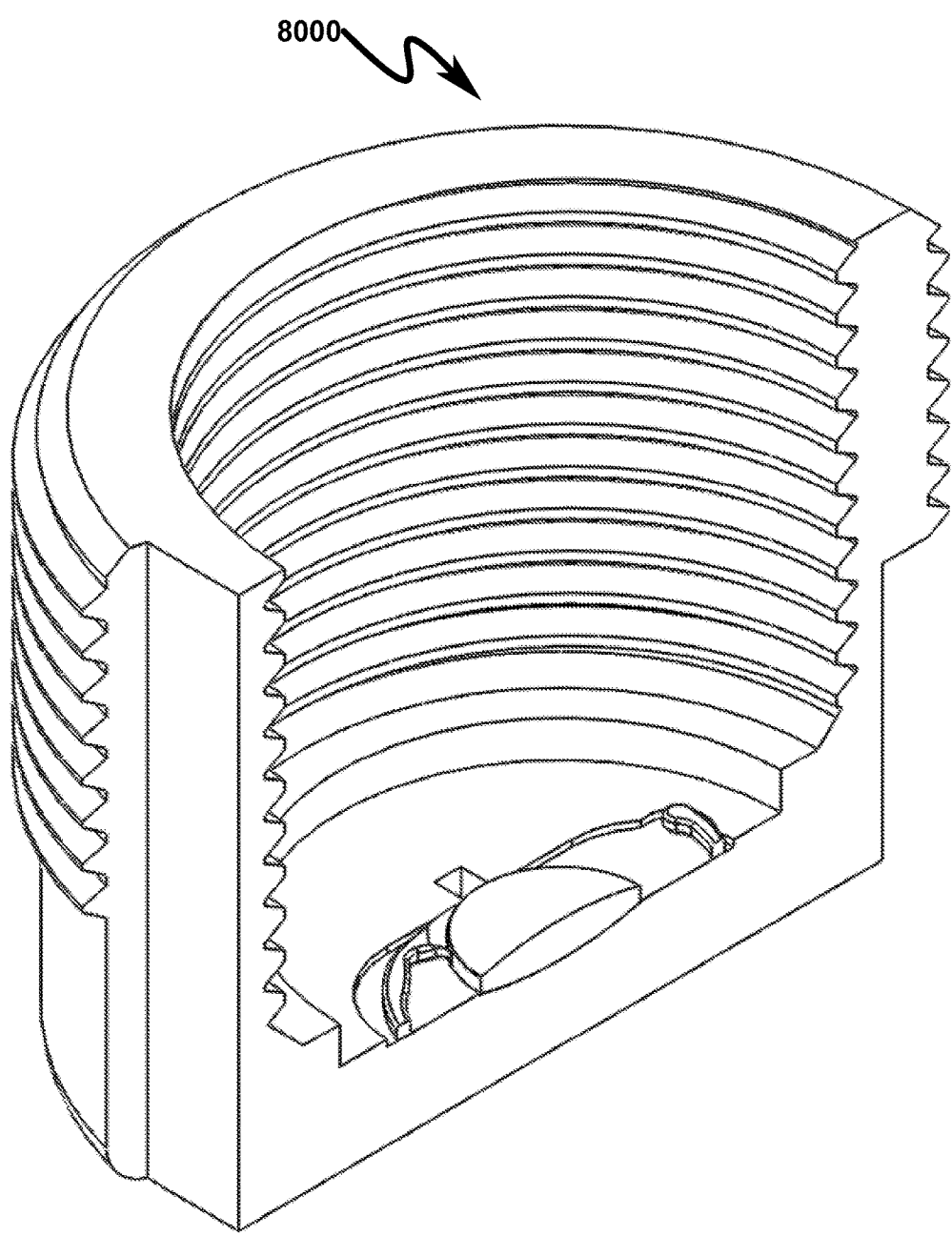
FIG. 80 illustrates a top right front perspective right section view of a preferred exemplary invention cylindrical cartridge SLC ophthalmic lens blank (OLB) embodiment with hermetic seal removed.
Figure 96:
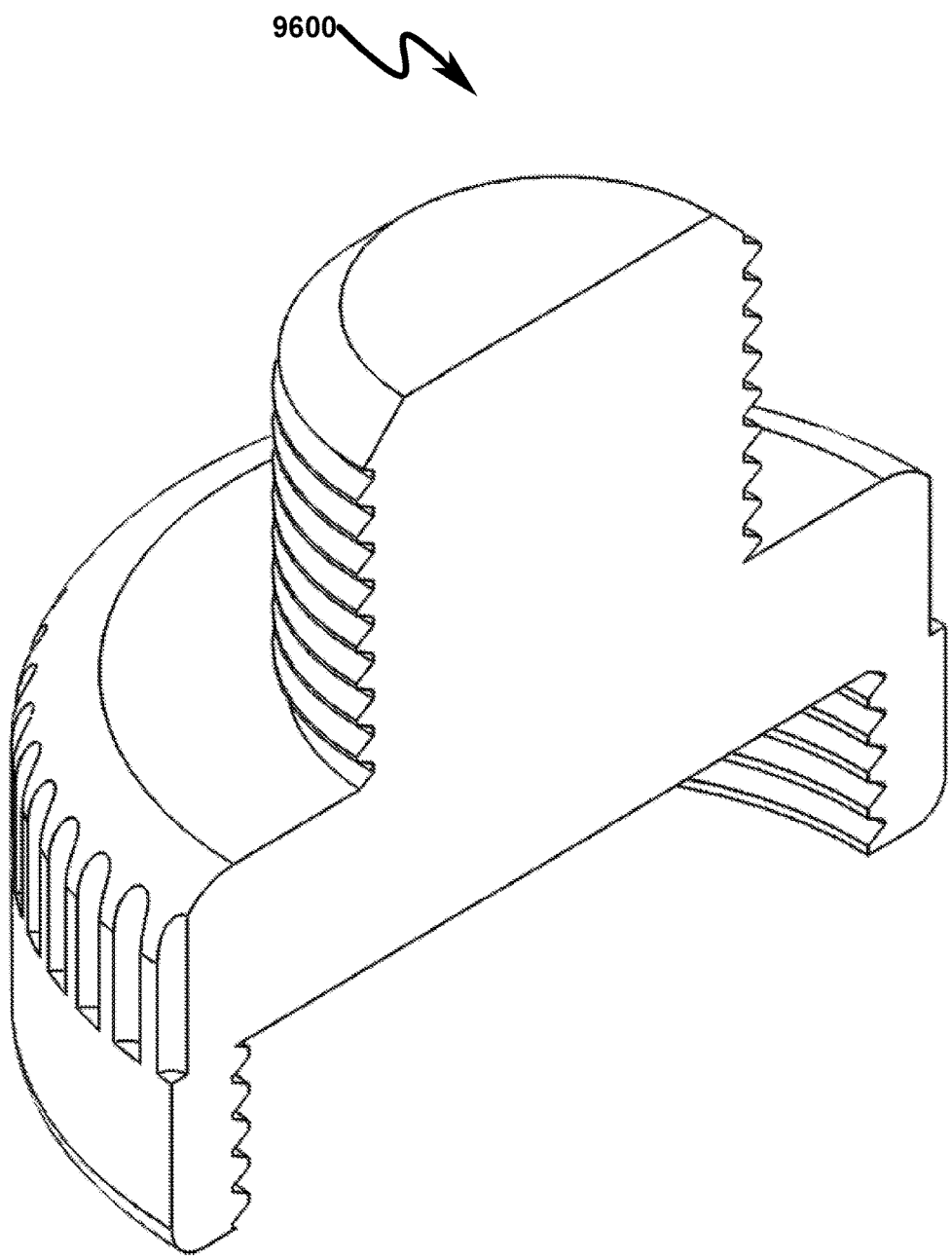
FIG. 96 illustrates top right front perspective right section views of a preferred exemplary invention cylindrical cartridge SLC enclosure cap (SEC) embodiment.

An exemplary cylindrical cartridge SLC embodiment is generally depicted in FIG. 65 (6500)-FIG. 96 (9600). As depicted in FIG. 65 (6500) it can be seen that a baseplate fixture (6501) securely retains the cylindrical cartridge SLC (6502) to permit laser radiation to be focused on the OLB contained within the SLC (6502). Further detail of the interaction between the baseplate fixture (6501) and the square SLC (6502) can be seen by inspection of FIG. 65 (6500)-FIG. 72 (7200). Detail views of the SLC with OLB installed are depicted in FIG. 73 (7300)-FIG. 80 (8000). The cavity in which the OLB is retained within the SLC is generally filled with a fluid suitable for transmission of laser radiation to the OLB during the customization process. This fluid may include but is not limited to distilled water and/or deionized water and/or a physiological saline solution.

Figure 81:
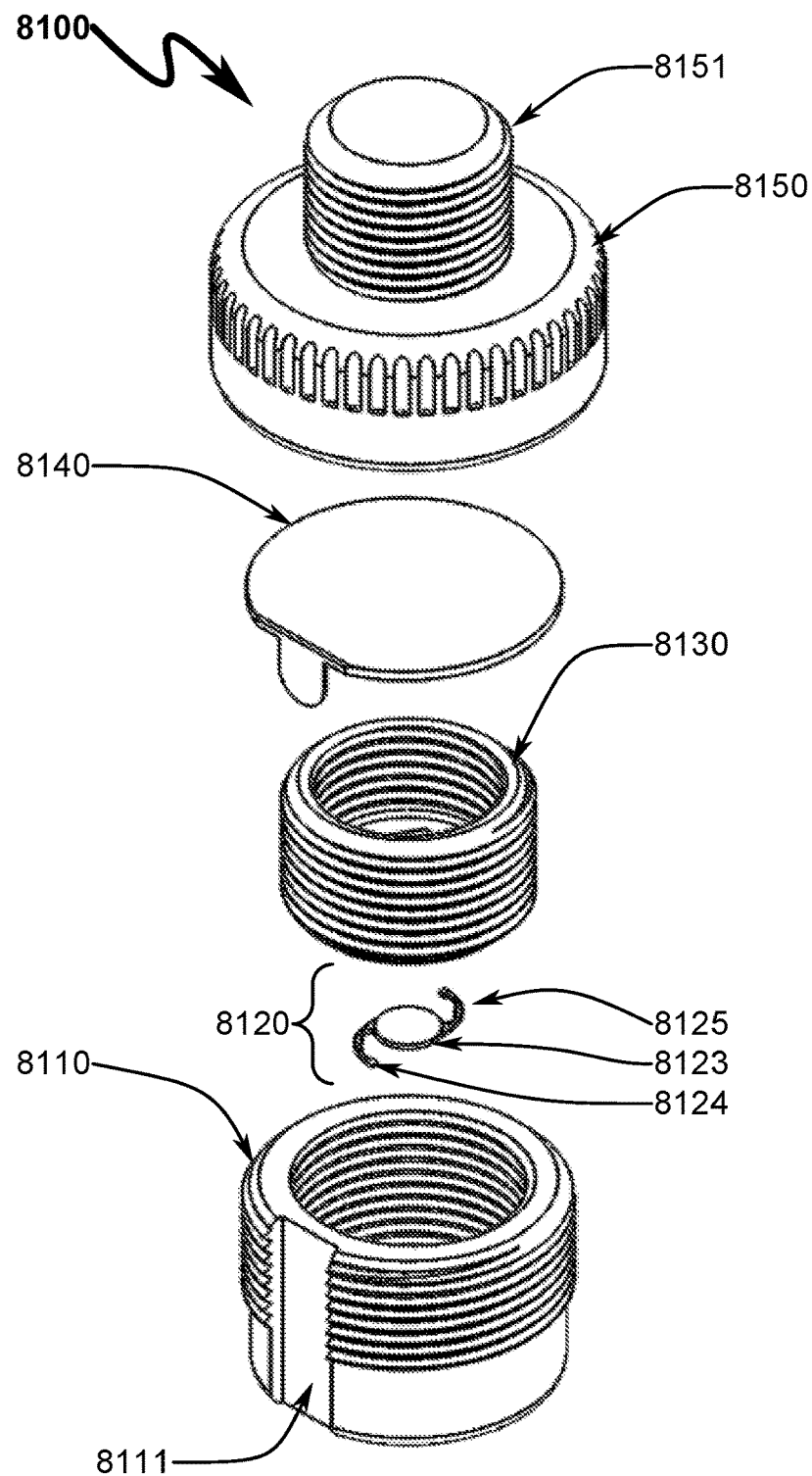
FIG. 81 illustrates a top right front perspective assembly view of a preferred exemplary invention cylindrical cartridge SLC ophthalmic lens blank (OLB) retainer embodiment.
Figure 82:
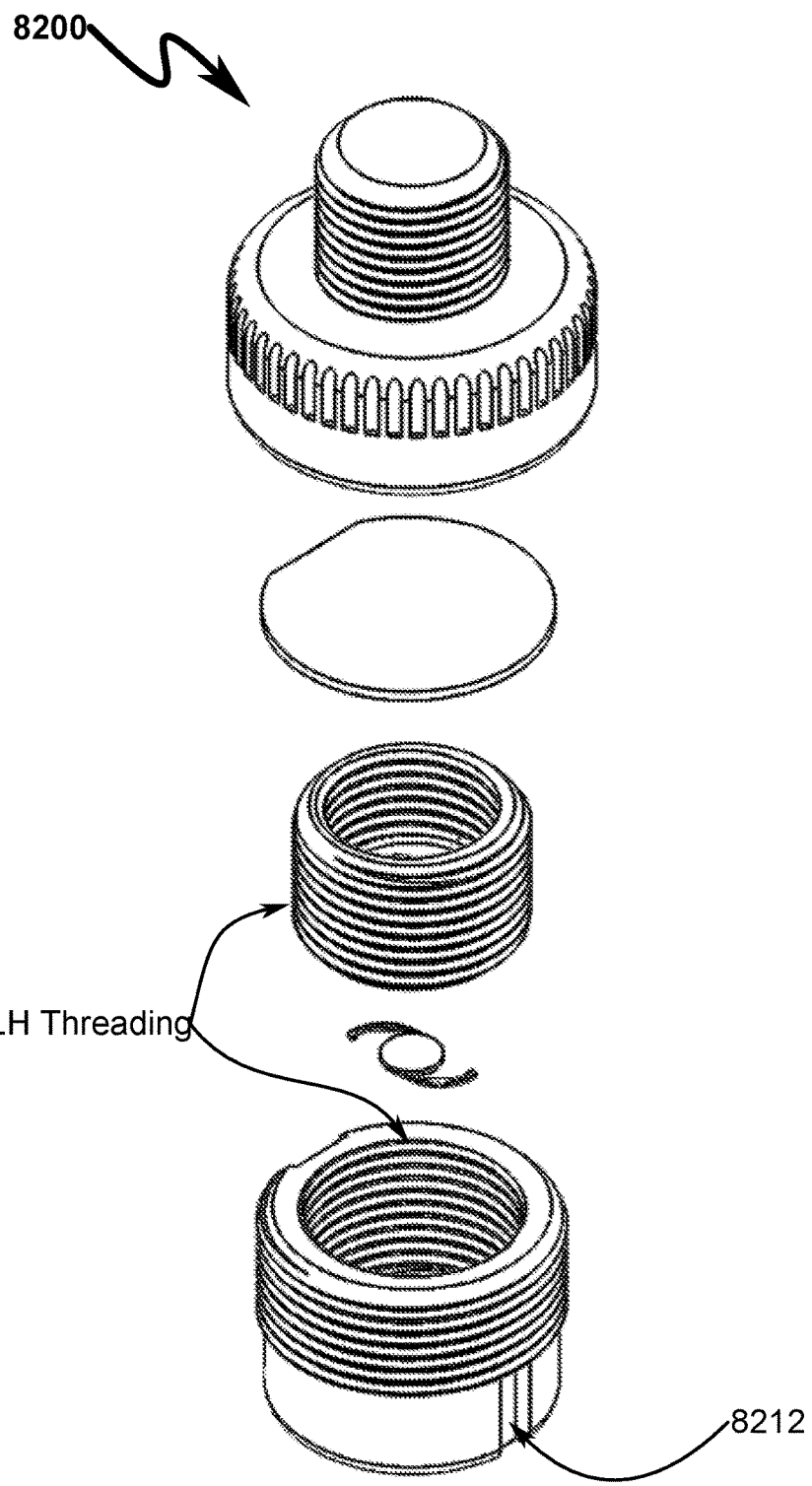
FIG. 82 illustrates a top right rear perspective assembly view of a preferred exemplary invention cylindrical cartridge SLC ophthalmic lens blank (OLB) retainer embodiment.
Figure 83:
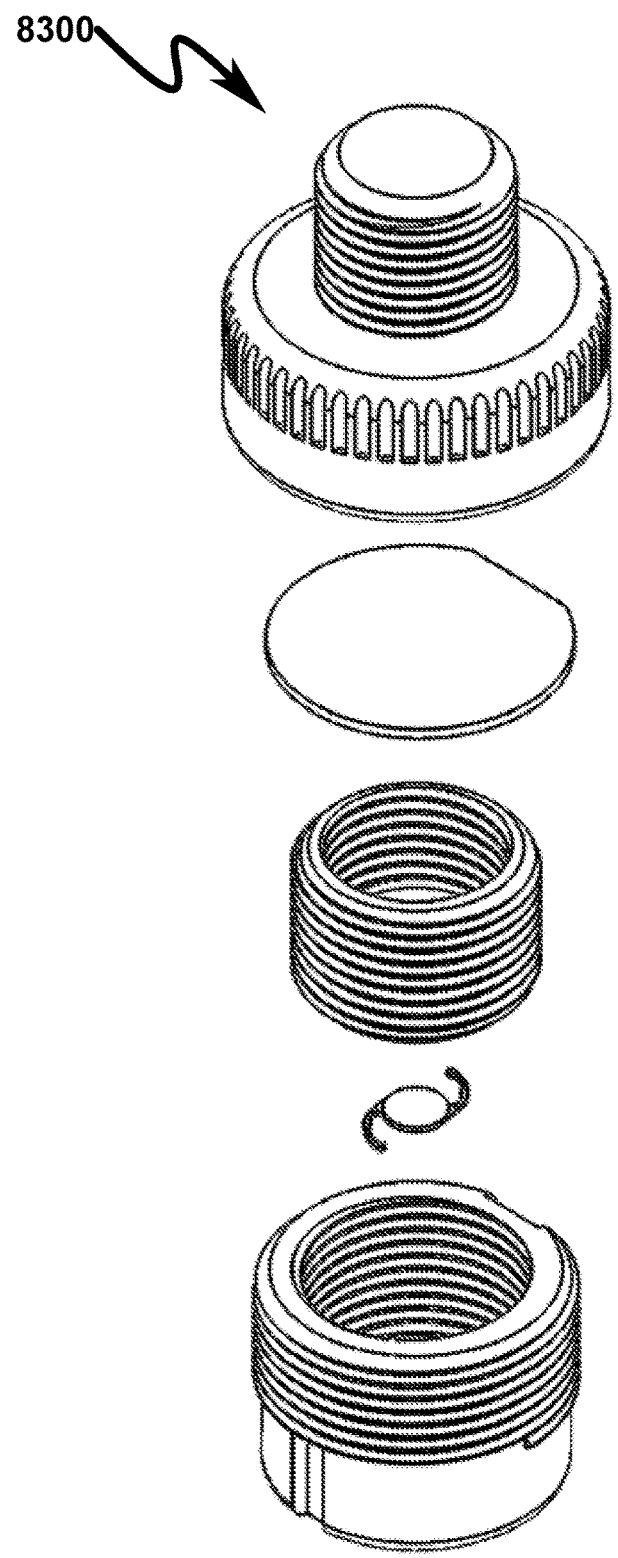
FIG. 83 illustrates a top left rear perspective assembly view of a preferred exemplary invention cylindrical cartridge SLC ophthalmic lens blank (OLB) retainer embodiment.
Figure 84:
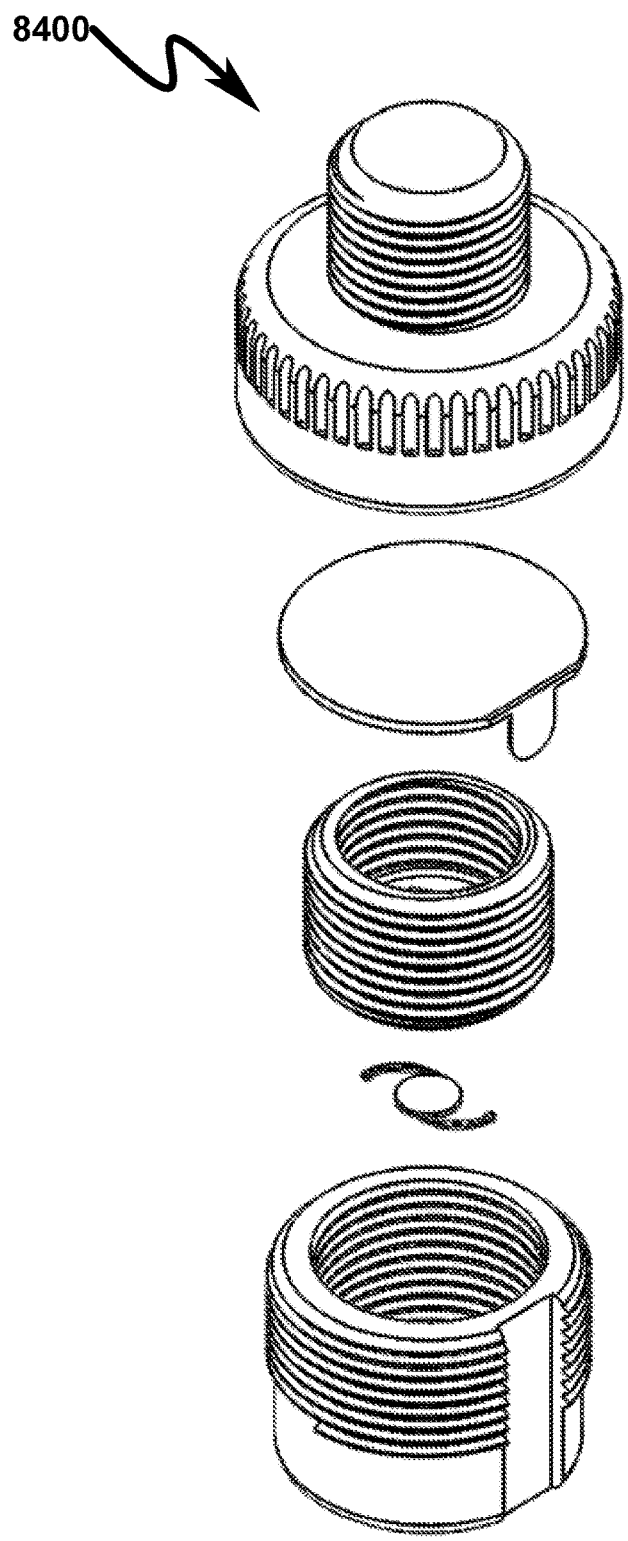
FIG. 84 illustrates a top left front perspective assembly view of a preferred exemplary invention cylindrical cartridge SLC ophthalmic lens blank (OLB) retainer embodiment.
Figure 85:
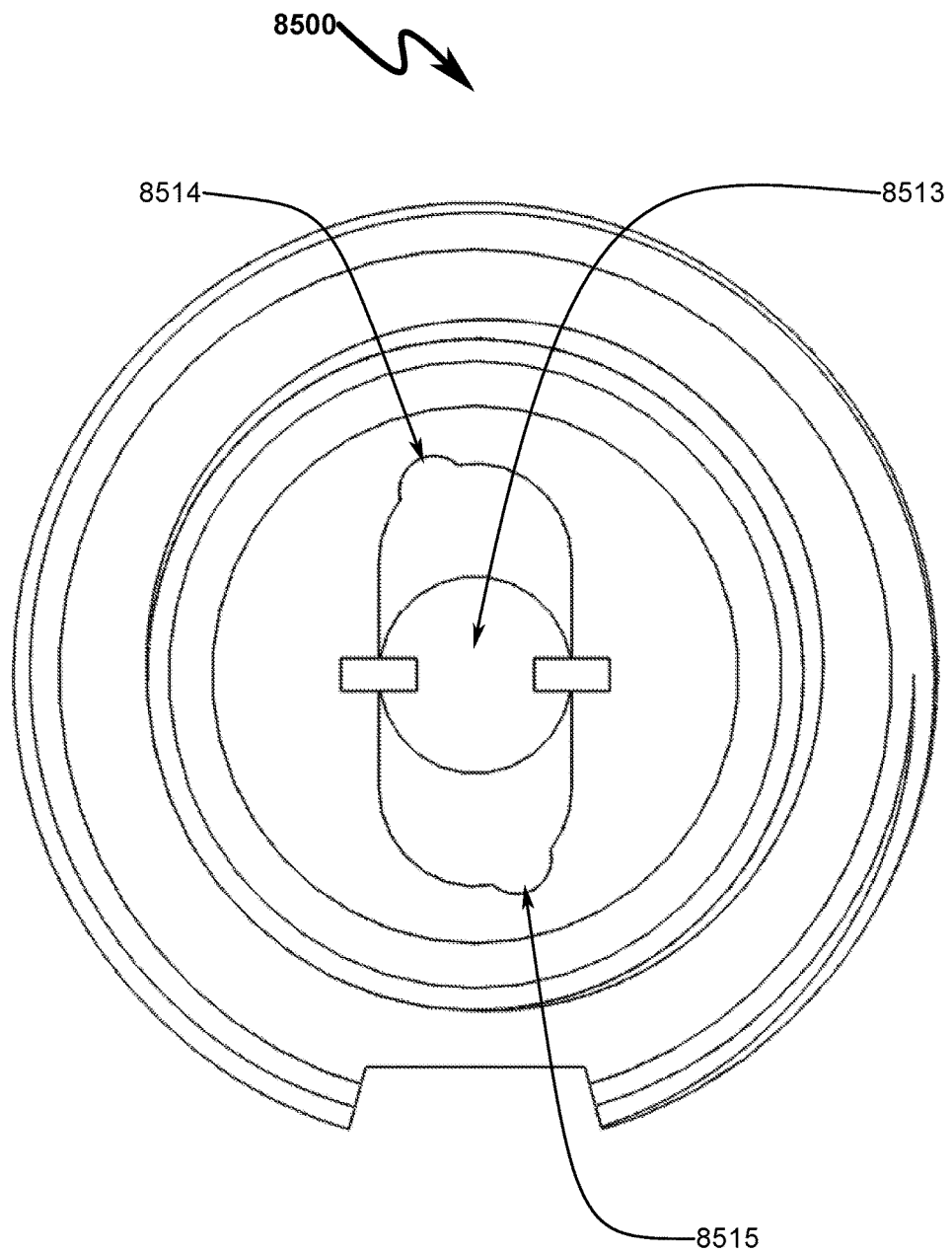
FIG. 85 illustrates a top view of a preferred exemplary invention cylindrical cartridge SLC fixture embodiment.
Figure 86:
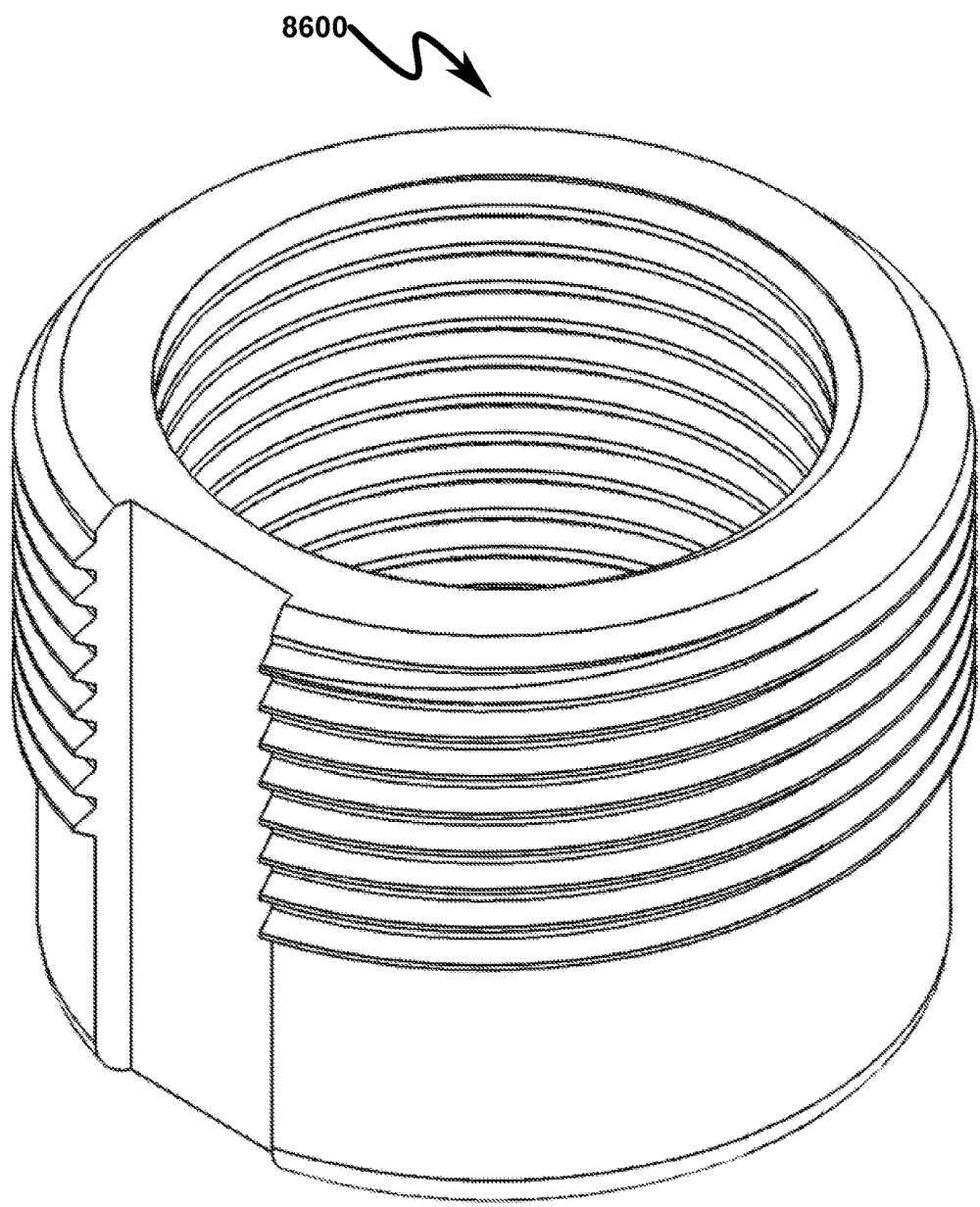
FIG. 86 illustrates a top right front perspective view of a preferred exemplary invention cylindrical cartridge SLC fixture embodiment.
Figure 87:
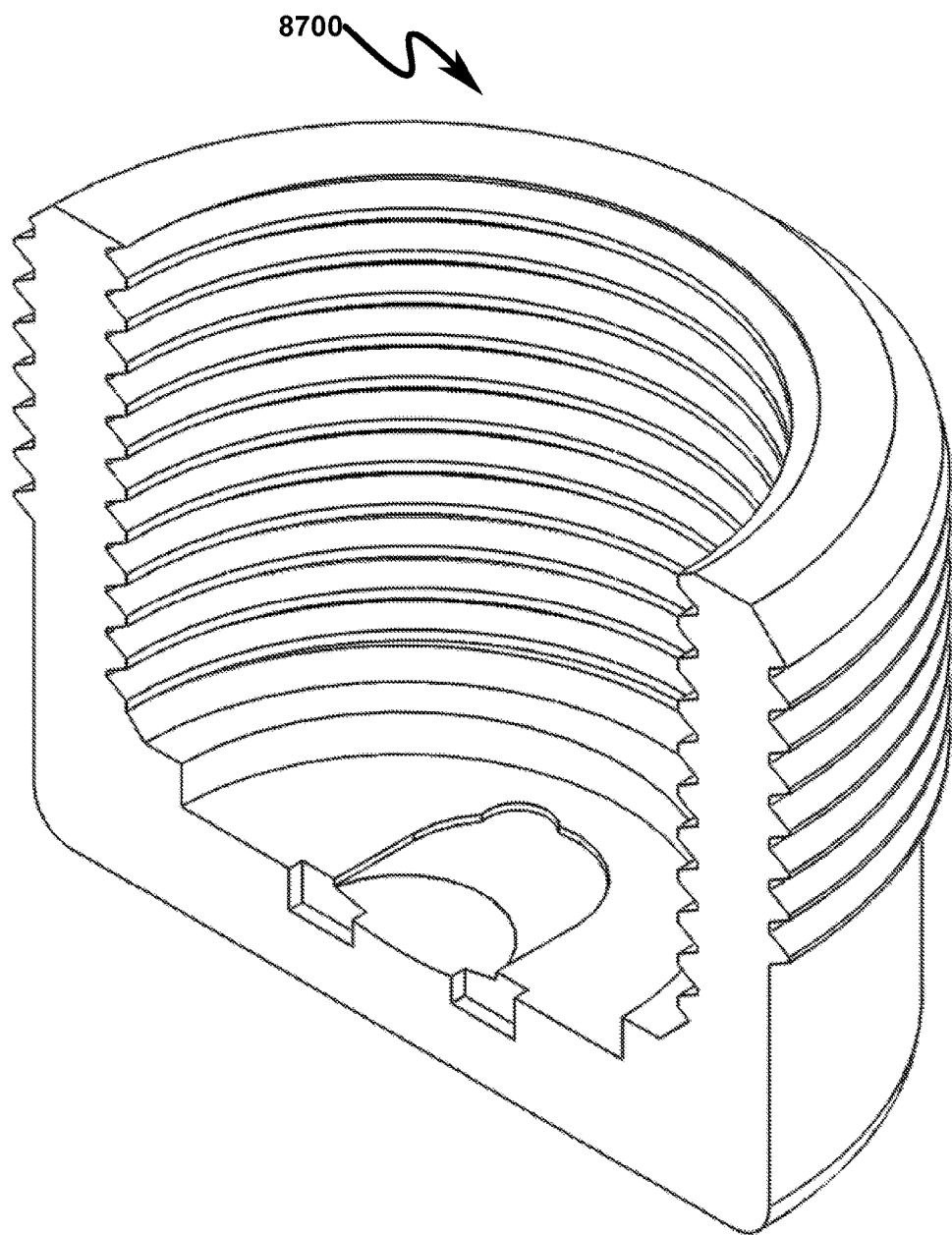
FIG. 87 illustrates top right front perspective front section views of a preferred exemplary invention cylindrical cartridge SLC fixture embodiment.
Figure 88:
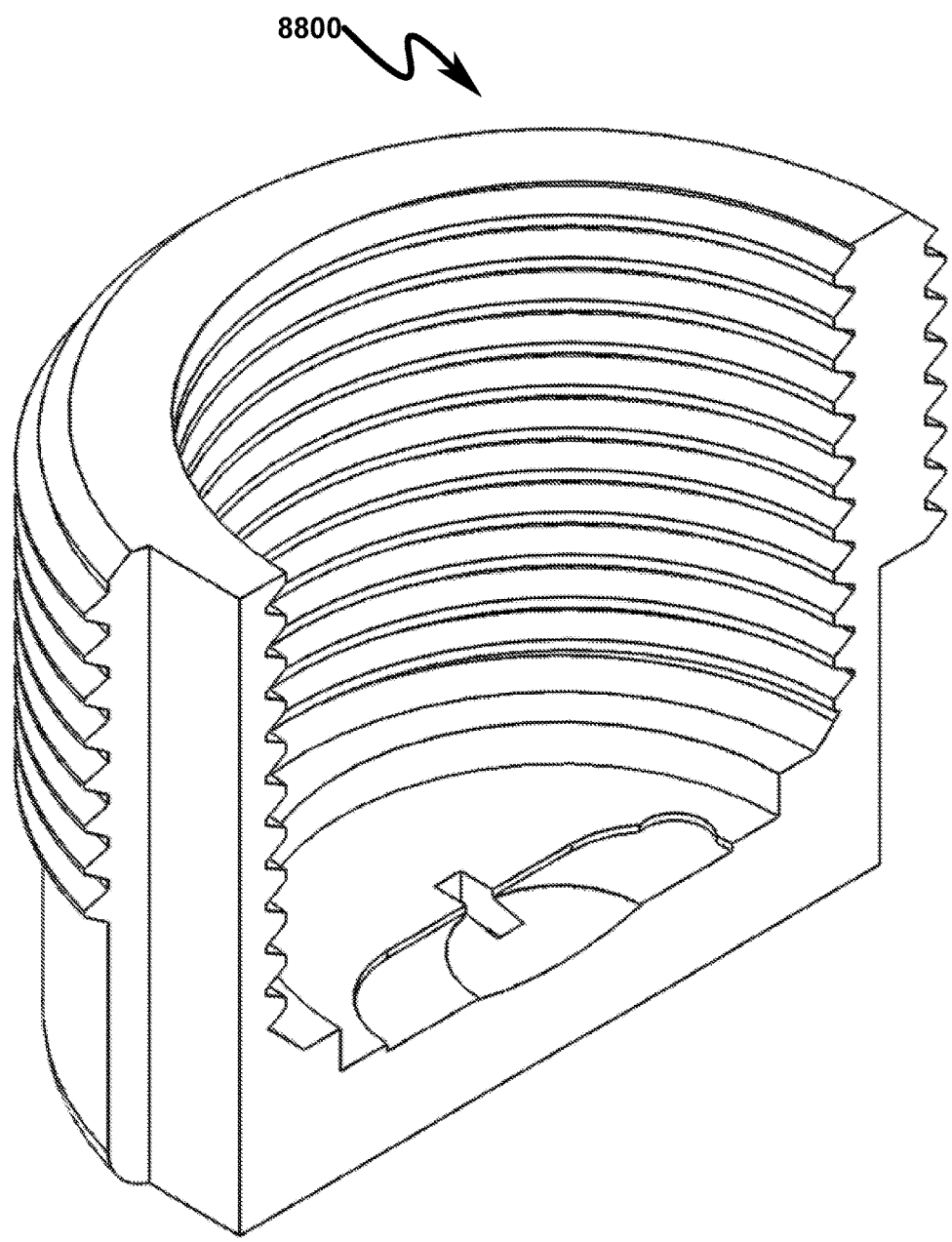
FIG. 88 illustrates top right front perspective right section views of a preferred exemplary invention cylindrical cartridge SLC fixture embodiment.
Figure 90:
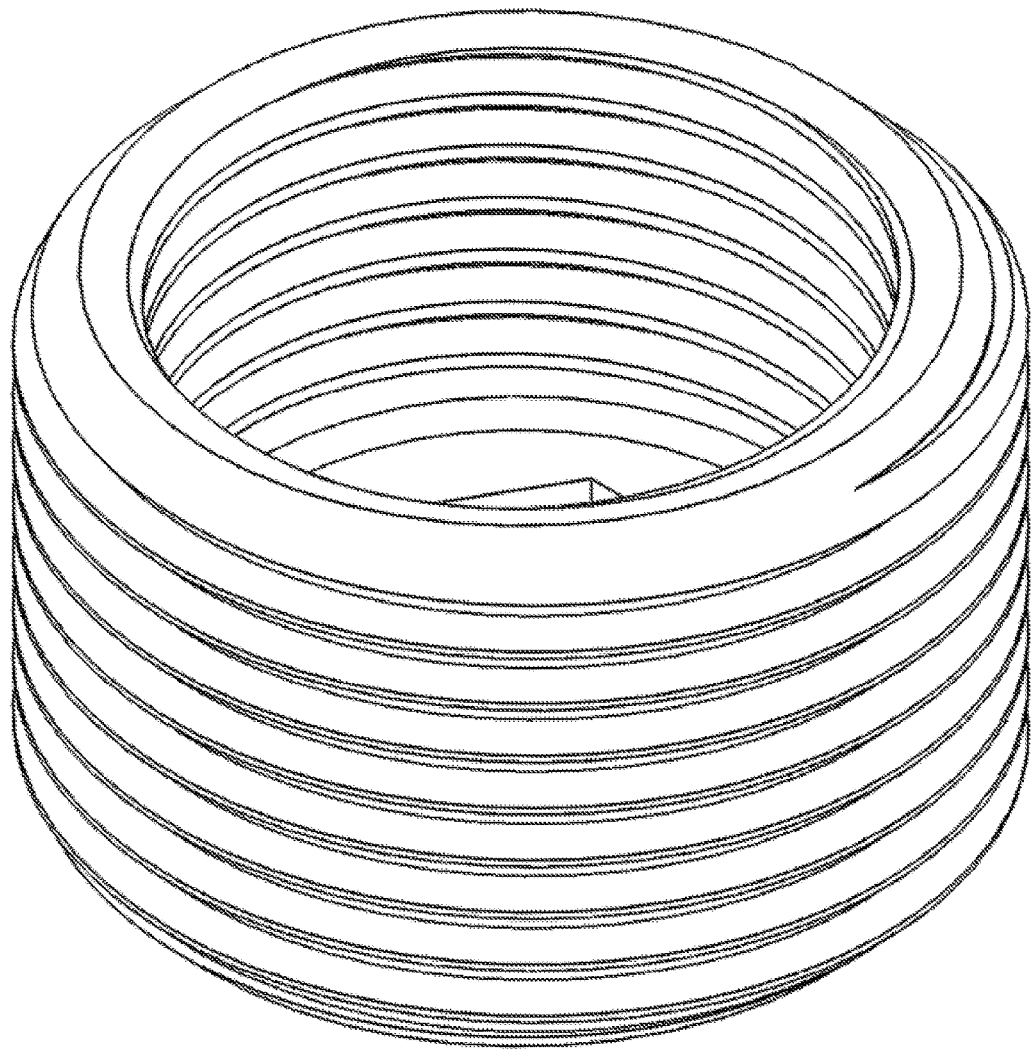
FIG. 90 illustrates a top right front perspective view of a preferred exemplary invention cylindrical cartridge SLC retainer sealing cap (RSC) embodiment.
Figure 91:
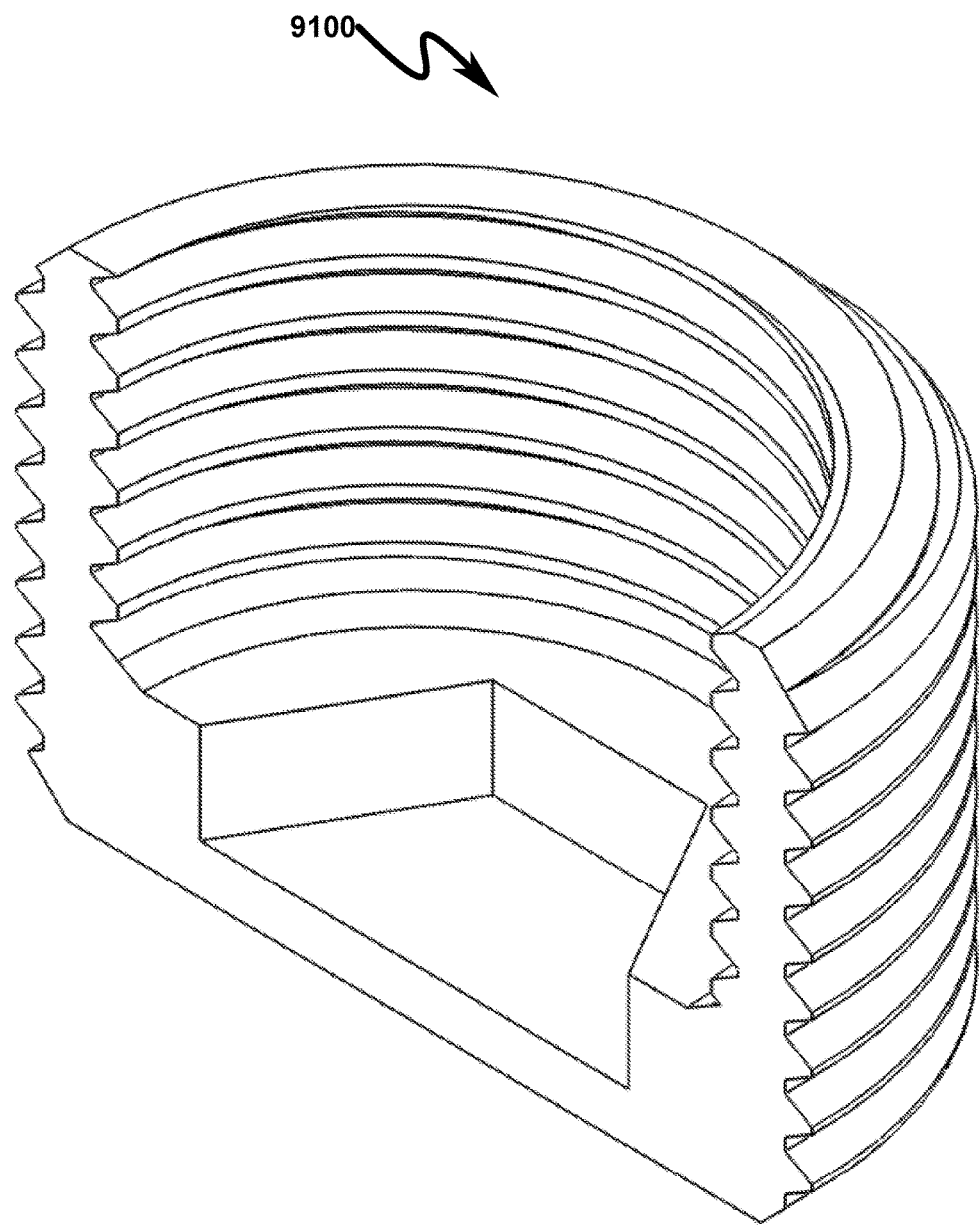
FIG. 91 illustrates top right front perspective front section views of a preferred exemplary invention cylindrical cartridge SLC retainer sealing cap (RSC) embodiment.

Additional detail of the exemplary SLC and OLB can be seen by inspecting FIG. 81 (8100)-FIG. 88 (8800) in which the SLC carrier (8110) is depicted having one or more lens position identifier (LPI) (8111, 8212) features to ensure that the OLB (8120) is properly oriented and secured for laser irradiation when installed in the baseplate fixture (6501). The lens position identifier (LPI) (8111, 8212) features may include keys of differing widths on either side of the SLC carrier (8110) to permit defined alignment orientation of the SLC carrier (8110) with the baseplate fixture (6501). A lens cavity (8513) and corresponding haptic retainers (8514, 8515) are provided within the SLC carrier (8110) to secure the OLB (8120) lens (8123) and corresponding lens haptics (8124, 8125). A retainer sealing cap (RSC) (8130) mates with the SLC carrier (8110) to hermetically seal the OLB (8120) within the iens cavity (8513) of the SLC carrier (8110).

A sealing lid (8140) is provided to seal the SLC (8110) and permit the SLC (8110)/OLB (8120) combination to be sterilized after assembly. This sealing lid (8140) may also serve as a dust cover for the retainer sealing cap (RSC) (8130). In this configuration the sealing lid (8140) may be configured to transmit laser radiation through to the liquid covering the OLB (8120) or in some circumstances the sealing lid (8140) may be removed prior to customization in which case the laser radiation is directly impinges the retainer sealing cap (RSC) (8130) and then impinges the OLB (8120) to affect refractive index changes in the OLB (8120) to generate a custom iens structure. If laser radiation is to be directed through the sealing lid (8140), the sealing lid (8140) will be constructed of material having a refractive index in the range of 1.05 to 1.65.

This configuration may be configured with an SLC enclosure cap (SEC) (8150) configured as follows. The SLC enclosure cap (SEC) (8150) may be fitted with screw threads that mate with the SLC (8110) to provide protection for the sealing lid (8140). Once the OLB (8120) has been inserted in the SLC (8110) and covered with fluid, the retainer sealing cap (RSC) (8130) is installed using left-hand threading into the SLC (8110). The sealing lid (8140) is installed and then the SLC enclosure cap (SEC) (8150) is installed on the SLC (8110) to protect the overall assembly. The assembly is then sterilized as a unit. During the lens customization process, the SLC enclosure cap (SEC) (8150) and sealing lid (8140) are removed, and laser radiation is directed through the retainer sealing cap (RSC) (8130) and fluid-filled lens chamber to modify the refractive index of the OLB (8120). After lens customization has been completed, the distal right-hand-threaded end (8151) of the SLC enclosure cap (SEC) (8150) is inserted into the retainer sealing cap (RSC) (8130) using normal right-hand insertion. Once the SLC enclosure cap (SEC) (8150) distal end (8151) bottoms out into the retainer sealing cap (RSC) (8130), the left-hand threads between the sealing cap (8130) and the SLC (8110) will become loosened, allowing the sealing cap (8130) to be removed from the SLC (8110). At this point the customized OLB/IOL (8120) may be removed from the SLC and presented/prepared for patient insertion.

Figure 92:
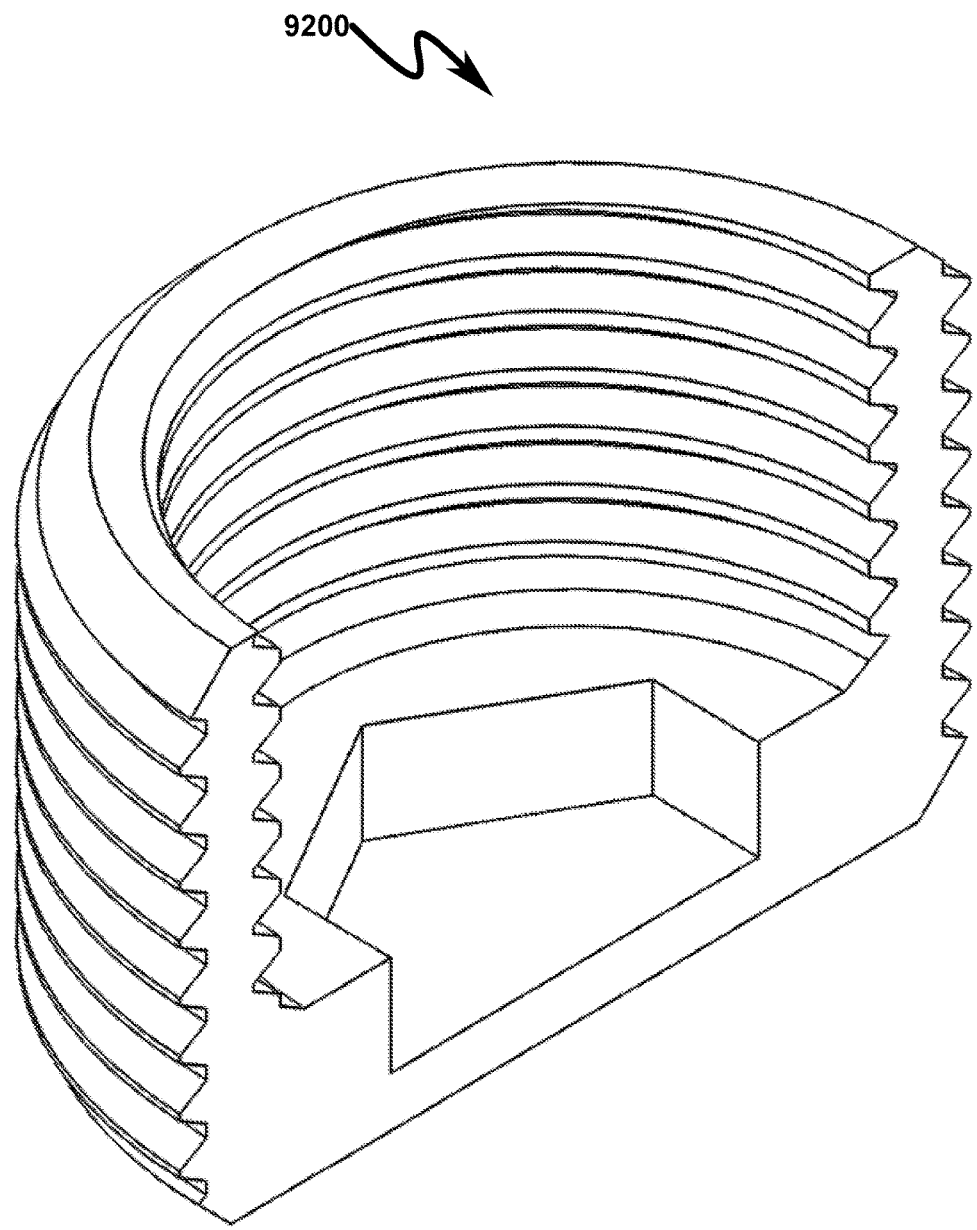
FIG. 92 illustrates top right front perspective right section views of a preferred exemplary invention cylindrical cartridge SLC retainer sealing cap (RSC) embodiment.
Figure 93:
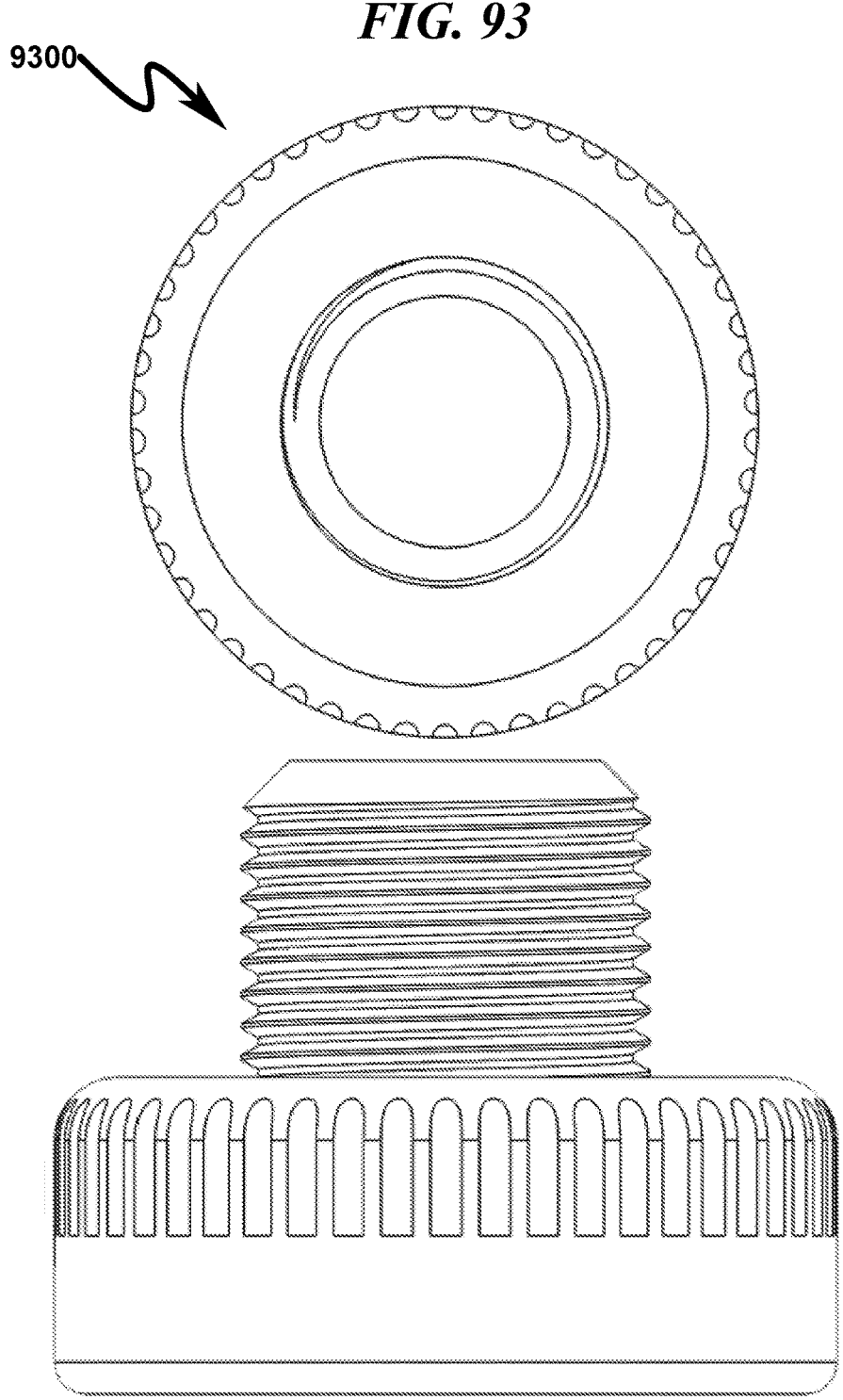
FIG. 93 illustrates a top view of a preferred exemplary invention cylindrical cartridge SLC enclosure cap (SEC) embodiment.
Figure 94:
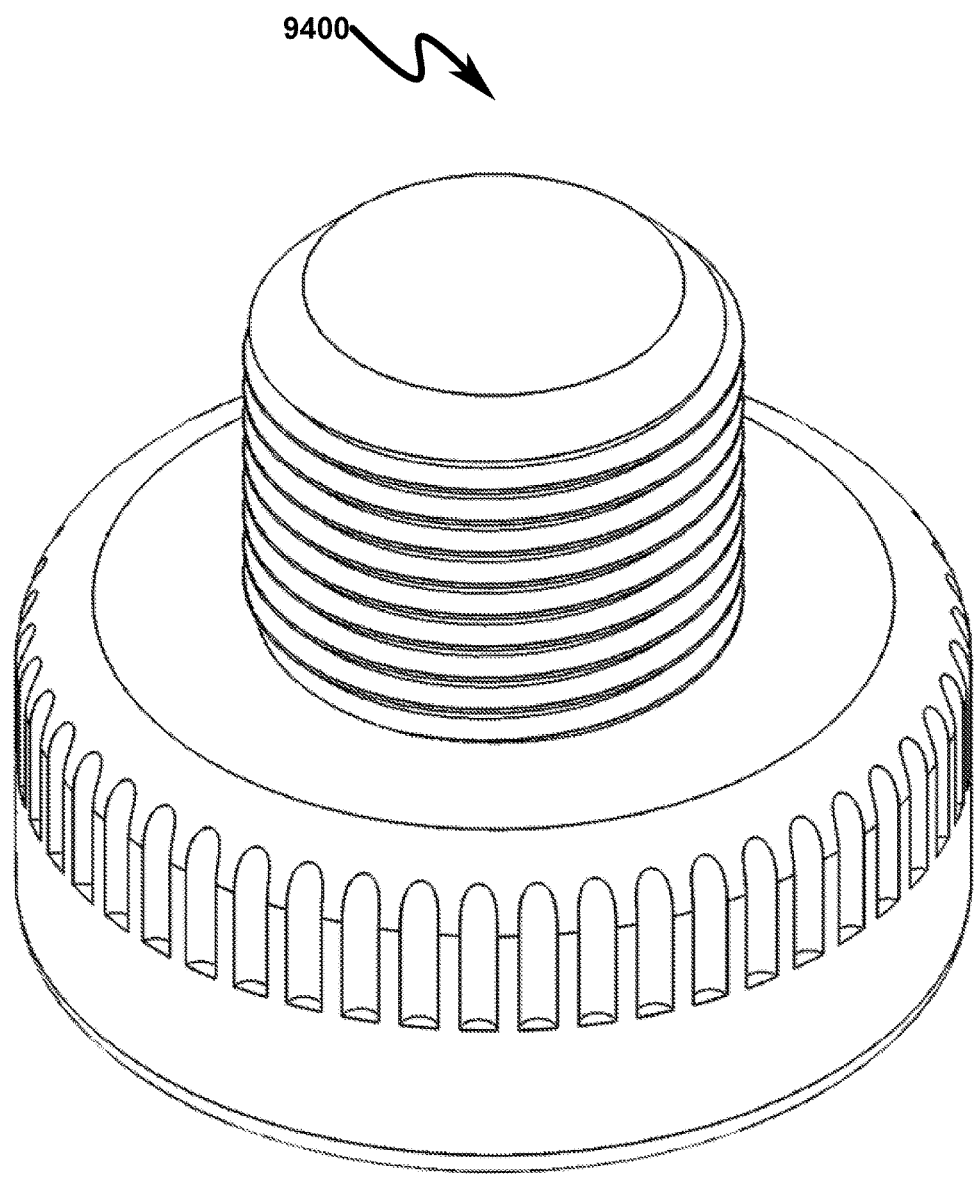
FIG. 94 illustrates a top right front perspective view of a preferred exemplary invention cylindrical cartridge SLC enclosure cap (SEC) embodiment.
Figure 95:
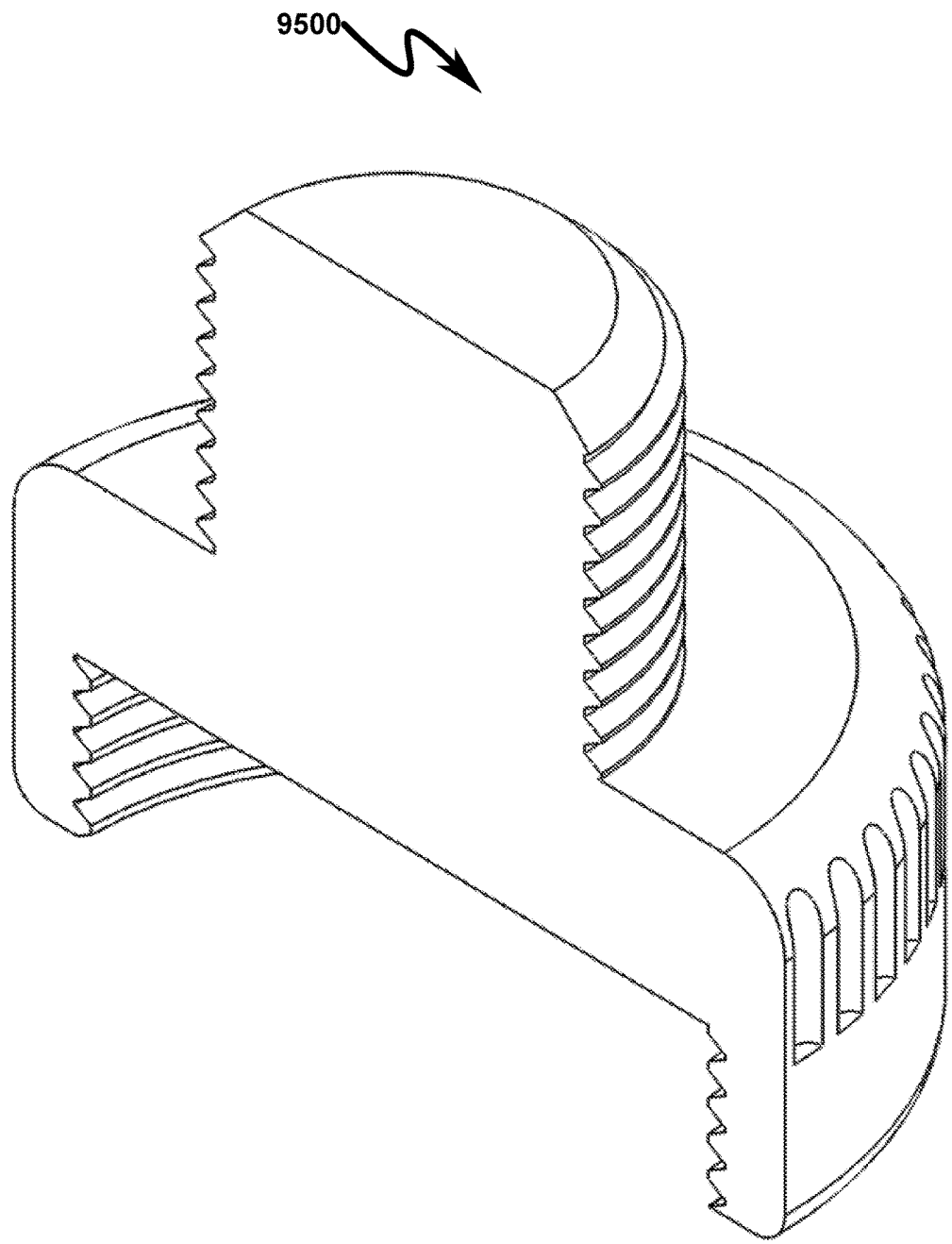
FIG. 95 illustrates top right front perspective front section views of a preferred exemplary invention cylindrical cartridge SLC enclosure cap (SEC) embodiment.

Note that the use of a SLC enclosure cap (SEC) (8150) in conjunction with the retainer sealing cap (RSC) (8130) permits the retainer sealing cap (RSC) (8130) to be removed from the SLC (8110) with the use of the distal end (8151) of the SLC enclosure cap (SEC) (8150), but not re-installed on the SLC (8110) using the SLC enclosure cap (SEC) (8150). This acts as a tamper-proof verification that the hermetic seal between the retainer sealing cap (RSC) (8130) and the SLC (8110) has only been broken once after assembly of the system is completed and the unit as a whole has been sterilized. As depicted in FIG. 89 (8900)-FIG. 92 (9200), the retainer sealing cap (RSC) (8130) may incorporate a hexagonal boss at its internal base that suitable for use with a hex key wrench for the initial assembly of the retainer sealing cap (RSC) (8130) to the SLC (8110) using the left-hand threading of the SLC (8110)/retainer sealing cap (RSC) (8130) interface.

Customized Optical Correction

The present invention anticipates that customization of the OLB to produce a customized intraocular lens (IOL) may include optical correction for diopter, spherical, cylindrical, asphericity, and/or multifocality, all in conformance with the requirements for an individual patient optical prescription.

Patient Prescription Measurement

While a variety of patient prescription measurement techniques may be used to determine parameters for generation of a custom IOL from, the OLB, the use of commercial optical wavefront measurement techniques or other equivalent methods are desirable in many application contexts.

OLB Diopter Ranges

While it is anticipated that, a baseline diopter of 15 may be optimal for many OLB configurations, the uncorrected OLB diopter is anticipated to range from 10-30 in many preferred embodiments, with 10, 20, and 30 being considered optimal starting points for customization in many application contexts. Many OLB configurations will be infused with minimal UV absorber, with additional UV absorber being included in lenses requiring enhanced reactive capacity with respect to laser radiation.

Typical OLB Dimensions

The OLB is retained within the SLC which comprises a sealed container that has been sterilized. The OLB lens is typically 6 mm in diameter and approximately 500 um or greater in depth. The lens haptics can vary in size but the SLC containment structure is typically about 6 mm in diameter and 1 mm-2 mm in height. The SLC cover is transparent to laser radiation with and a refractive index of from between 1.05 and 1.50.

OLB Customization Options

The present invention provides for customized diopter (spherical and cylindrical), custom asphericity, and custom multi-focality within the context of a physician's office and outside of the normal laboratory manufacturing process normally associated with lens customization. The multi-focality customization may be configured as diffractive or refractive. The light split of the multi-focal may be configured as selected by the doctor. Typical light split ranges to 70/30, 60/40, or 50/50 but may be possible to achieve 80/20 in some circumstances. The ability of the present invention to support muiti-focais is in contrast to prior art iens manufacturers that have no support for refractive multi-focals.

OLB Index/Orientation

The integrated SLC provided for in the teachings of the present invention provides for stabilization of the OLB during lens customization by the laser radiation but also provides for proper indexing and orientation of the OLB during the customization process. As the OLB may have one or more axis of symmetry, the proper orientation of the OLB during the process of customization is critical to ensuring that the lens is properly constructed according to any asymmetry measured in the patient.

Sterilization

The present invention anticipates that the packaged SLC+OLB combination will be sterilized via the use of gamma radiation or means of equivalent effectiveness in order to ensure that the OLB as customized will be free from infectious content when installed in the recipient patient.

Customization Treatment Time

While the time for customization of the ophthalmic lens may vary based on application context, typical treatment times range from 10 seconds to 10 minutes (including docking time) in duration.

System Summary

The present invention system may be broadly generalized as an ophthalmic lens customization system comprising:
- (a) ophthalmic lens blank (OLB);
- (b) secured lens container (SLC);
- (c) lens position identifier (LPI);
- (d) pulsed laser source (PLS);
- (e) laser steering scanner (LSS); and
- (f) focusing microscope objective (EMC);

wherein:
- the OLB comprises a clear material impregnated with an ultraviolet absorber (UVA);
- the OLB comprises a blank lens structure (BLS) and lens haptics (BLH);
- the SLC comprises a hermetically sealed enclosure (HSE) having an internal container void (ICV);
- the HSE comprises a HSE bottom plate (HBP) and a HSE top cover (HTC);
- the ICV comprises an internal volume configured to contain the OLB;
- the OLB is retained within the ICV via the BLH;
- the LPI is configured to define the orientation of the OLB within the SLC;

the OLB is covered within the ICV at least in part with a lens filler material (LFIM);

the HSE is configured to be hermetically sealed after the OLB is retained within the ICY while the LFM covers at least part of the OLB;

the PLS comprises a femtosecond laser radiation source configured to emit a pulsed laser radiation (PLR) output;

the LSS is configured to distribute the PLR output across an input area of the FMO;

the FMO further comprises a numerical aperture configured to accept the distribution of the PLR output across the input area of the FMO and produce a focused laser radiation (FLR) output;

the FLR output is transmitted by the FMO through the HTC and the LFM to the OLB;

the FLR output is transmitted to the OLB based on a lens position defined by the LPI;

the FLR output interacts with the UVA within the OLB to change the refractive index of an internal region of the OLB; and the HSE is configured to be unsealed after the refractive index of the internal region of the OLB has been changed by application of the FLR to the OLB.

This general system summary may be augmented by the various elements described herein to produce a wide variety of invention embodiments consistent with this overall design description.

Method Summary

The present invention method may be broadly generalized as an ophthalmic lens customization method comprising:

(1) impregnating an ophthalmic lens blank (OLB) comprising a clear material with an ultraviolet absorber (UVA); the OLB comprising a blank lens structure (BLS) and lens haptics (BLH);

(2) placing the OLB within a secured lens container (SLC), the SLC comprising a hermetically sealed enclosure (HSE) having an internal container void (ICV); the HSE comprising a HSE bottom plate (HBP) and a HSE top cover (HTC); and the ICV comprising an internal volume configured to contain the OLB; the OLB retained within the ICV via the BLH;

(3) defining the orientati on of tne OLB within tne SLC with a lens position identifier (LPI);

(4) covering the OLB within the ICV at least in part with a lens filler material (LFM);

(5) hermetically sealing the HSE after the OLB is retained within the ICV while the LFM covers at least part of the OLB;

(6) sterilizing the OLB within the HSE after the OLB is retained within the ICV while the LFM covers at least part of the OLB;

(7) configuring a pulsed laser source (PLS) comprising a femtosecond laser radiation source to emit a pulsed laser radiation (PLR) output;

(8) distributing the PLR output across an input area of a focusing microscope objective (FMO) with a laser steering scanner (LSS); the FMO further comprising a numerical aperture configured to accept the distribution of the PLR output across the input area of the FMO and produce a focused laser radiation (FLR) output;

(9) transmitting the FLR output by the FMO through the HTC and the LFM to the OLB;

(10) transmitting the FLR output to the OLB based on a lens position defined by the LPI;

(11) changing the refractive index of an internal region of the OLB via the FLR output interaction with the UVA within the OLB; and

(12) unsealing the HSE after the refractive index of the internal region of the OLB has been changed by application of the FLR to the OLB.

This general method may be modified heavily depending on a number of factors, with rearrangement and/or addition/deletion of steps anticipated by the scope of the present invention. Integration of this and other preferred exemplary embodiment methods in conjunction with a variety of preferred exemplary embodiment systems described herein is anticipated by the overall scope of the present invention.

System/Method/Product-by-Process Vaariations

The present invention anticipates a wide variety of variations in the basic theme of construction. The examples presented previously do not represent the entire scope of possible usages. They are meant to cite a few of the almost limitless possibilities.

This basic system, method, and product-by-process may be augmented with a variety of ancillary embodiments, including but not limited to:

An embodiment wherein the OLB comprises a material selected from a group consisting of: acrylic; silicon; poly(methyl methacrylate (PMMA); and PMNA plastic.

An embodiment wherein the OLB comprises an ophthalmic lens with known diopter (OKD).

An embodiment wherein the SLC comprises a material having a refractive index in the range of 1.05 to 1.65.

An embodiment wherein the HBP comprises a clear or colored material.

An embodiment wherein the HTC comprises a material transparent to ultraviolet (UV) radiation.

An embodiment wherein the LFM comprises a fluid selected from a group consisting of: distilled water; deionized water; and a physiological saline solution.

An embodiment wherein the PLR output has energy in a range of 0.01 microjoules to 15.0 microjoules, An embodiment wherein the FLR output has a repetition rate in the range of 0.1 MHz to 100 MHz.

An embodiment wherein the PLR output has a pulse width in the range of 10 fs to 950 fs.

An embodiment wherein the FLR output has a spot size in the X-Y directions in the range of 1.0 micrometers to 20.0 micrometers.

An embodiment wherein trie FLR output has a spot size in the Z-direct ion in the range of 0.05 micrometers to 200.0 micrometers.

An embodiment wherein the LSS is configured to distribute the FLR output in a two-dimensional pattern within the OLB.

An embodiment wherein the LSS is configured to distribute the FLR output in a three-dimensional pattern within the OLB.

An embodiment wherein the LSS is configured to distribute the FLR output in a three-dimensional pattern within the OLB, the pattern forming a convex iens within the OLB.

An embodiment wherein the LSS is configured to distribute the FLR output in a three-dimensional pattern within the OLB, the pattern forming a biconvex lens within the OLB.

An embodiment wherein the LSS is configured to distribute the FLR output in a three-dimensional pattern within the OLB, the pattern forming a concave lens within the OLB.

An embodiment wherein the LSS is configured to distribute the FLR output in a three-dimensional pattern within the OLB, the pattern forming a biconcave lens within the OLB.

An embodiment wherein the OLB comprises a cross-linked polymeric copolymer.

An embodiment wherein the OLB comprises a cross-linked polymeric acrylic polymer.

An embodiment wherein the FLS further comprises an optic modulator selected from a group consisting of: an Acousto-Optic: Modulator (AOM); and a greyscale Acousto-Optic Modulator (AOM).

An embodiment wherein the LSS is configured to distribute the FLR output in a two-dimensional or three-dimensional pattern within the OLB; the focused laser radiation creating a hydrophilicity change in a volume associated with the two-dimensional or three-dimensional pattern; and the hydrophilicity change resulting in a corresponding three dimensional change in refractive index of the volume associated with the two-dimensional or three-dimensional pattern, An embodiment wherein the hydrophilicity change results in a refractive index change within the OLB.

An embodiment wherein the refractive index change is greater than 0.01.

An embodiment wherein the two-dimensional or three-dimensional pattern comprises a plurality of layers within the OLB.

One skilled in the art will recognize that other embodiments are possible based on any combination of elements taught within the above invention description and various embodiments detailed above.

Generalized Computer Usable Medium

In various alternate embodiments, the present invention may be implemented as a computer program product for use with a computerized computing system. Those skilled in the art will readily appreciate that programs defining the functions defined by the present invention can be written in any appropriate programming language and delivered to a computer in many forms, including but not limited to: (a) information permanently stored on non-writeable storage media (e.g., read-only memory devices such as ROMs or CD-ROM disks); (b) information alterably stored on writeable storage media (e.g., floppy disks and hard drives); and/or (c) information conveyed to a computer through communication media, such as a local area network, a telephone network, or a public network such as the Internet. When carrying computer readable instructions that implement the present invention methods, such computer readable media represent alternate embodiments of the present invention.

As generally illustrated herein, the present invention system embodiments can incorporate a variety of computer readable media that comprise computer usable medium having computer readable code means embodied therein. One skilled in the art will recognize that the software associated with the various processes described herein can be embodied in a wide variety of computer accessible media from, which the software is loaded and activated. Pursuant to In re Beauregard, 35 USPQ2c 1383 (U.S. Pat. No. 5,710,578), the present invention anticipates and includes this type of computer readable media within the scope of the invention. Pursuant to In re Nuijzen, 500 F.3d 1346 (Fed. Cir. 2007) (U.S. patent application Ser. No. 09/211,928), the present invention scope is limited to computer readable media wherein the media is both tangible and non-transitory.

CONCLUSION

A system/method allowing personalized ex vivo customization of a generic ophthalmic lens blank (OLB) or ophthalmic lens with known diopter (OKD) based on localized field-measured patient characteristics has been disclosed. The OLB is composed of an acrylic material that has been infused with an ultraviolet (UV) absorbing compound rendering it amenable to customized spatial modification (CSM) of its refractive index via the use of pulsed laser radiation (FLR). The CSM of refractive index eliminates the need for remote laboratory fabrication of a customized intraocular lens (IOL) for the patient. The OLB is retained within a secured lens container (SLC) providing for precise physical orientation of the OLB haptics and OLB lens structure with respect to the application of PLR to the OLB. The SLC contains a lens filler material (LFM) covering the OLB and is hermetically sealed after the OLB has been positioned within the SLC interior and prior to sterilization of the SLC+OLB combination.

CLAIMS INTERPRETATION

The following rules apply when interpreting the CLAIMS of the present invention:

The CLAIM PREAMBLE should be considered as limiting the scope of the claimed invention, "WHEREIN" clauses should be considered as limiting the scope of the claimed invention.

"WHEREBY" clauses should be considered as limiting the scope of the claimed invention.

"ADAPTED TO" clauses should be considered as limiting the scope of the claimed invention.

"ADAPTED FOR" clauses should be considered as limiting the scope of the claimed invention.

The term "MEANS" specifically invokes the means-plus-function claims limitation recited in 35 U.S.C, § 112(f) and such claim shall be construed to cover the corresponding structure; material, or acts described in the specification and equivalents thereof.

The phrase "MEANS FOR" specifically invokes the means-plus-function claims limitation recited in 35 U.S.C. § 112 (f) and such claim shall be construed to cover the corresponding structure, material, or acts described in the specification, and equivalents thereof.

The phrase "STEP FOR" specifically invokes the step-plus-function claims limitation recited in 35 U.S.C. § 112 (f) and such claim shall be construed to cover the corresponding structure, material, or acts described in the specification and equivalents thereof.

The step-plus-function claims limitation recited in 35 U.S.C. § 112(f) shall be construed to cover the corresponding structure, material, or acts described in the specification and equivalents thereof ONLY for such claims including the phrases "MEANS FOR", "MEANS", or "STEP FOR".

The phrase "AND/OR" in the context of an expression "X and/or Y" should be interpreted to define the set of "(X and Y)" in union with the set "(X or Y)" as interpreted by Ex Parte Gross (USPTO Patent Trial and Appeal Board, Appeal 2011-004811, Ser. No. 11/565,411, ("'and/or' covers embodiments having element A alone, B alone, or elements A and B taken together").

The claims presented herein are to be interpreted in light of the specification and drawings presented herein with sufficiently narrow scope such as to not preempt any abstract idea.

The claims presented herein are to be interpreted in light of the specification and drawings presented herein with sufficiently narrow scope such as to not preclude every application of any idea.

The claims presented herein are to be interpreted in light of the specification and drawings presented herein with sufficiently narrow scope such as to preclude any basic mental process that could be performed entirely in the human mind.

The claims presented herein are to be interpreted in light of the specification and drawings presented herein with sufficiently narrow scope such as to preclude any process that could be performed entirely by human manual effort.

What is claimed is:

1. An ophthalmic lens customization system comprising:
(a) ophthalmic lens blank (OLB);
(b) secured lens container (SLC);
(c) lens position identifier (LPI);
(d) pulsed laser source (PLS);
(e) laser steering scanner (LSS); and
(f) focusing microscope objective (FMO);
wherein:
said ophthalmic lens blank (OLB) comprises a clear material impregnated with an ultraviolet absorber (UVA);
said ophthalmic lens blank (OLB) comprises a blank lens structure (BLS) and lens haptics (BLH);
said secured lens container (SLC) comprises a hermetically sealed enclosure (HSE) having an internal container void (ICV);
said hermetically sealed enclosure (HSE) comprises a HSE bottom plate (HBP) and a HSE top cover (HTC);
said internal container void (ICV) comprises an internal volume configured to contain said ophthalmic lens blank (OLB);
said ophthalmic lens blank (OLB) is retained within said internal container void (ICV) via said lens haptics (BLH);
said lens position identifier (LPI) is configured to define the orientation of said ophthalmic lens blank (OLB) within said secured lens container (SLC);
said ophthalmic lens blank (OLB) is covered within said internal container void (ICV) at least in part with a lens filler material (LFM);
said hermetically sealed enclosure (HSE) is configured to be hermetically sealed after said ophthalmic lens blank (OLB) is retained within said internal container void (ICV) while said lens filler material (LFM) covers at least part of said ophthalmic lens blank (OLB);
said pulsed laser source (PLS) comprises a femtosecond laser radiation source configured to emit a pulsed laser radiation (PLR) output;
said laser steering scanner (LSS) is configured to distribute said pulsed laser radiation (PLR) output across an input area of said focusing microscope objective (FMO);
said focusing microscope objective (FMO) further comprises a numerical aperture configured to accept said distribution of said pulsed laser radiation (PLR) output across said input area of said focusing microscope objective (FMO) and produce a focused laser radiation (FLR) output;
said focused laser radiation (FLR) output is transmitted by said focusing microscope objective (FMO) through said HSE top cover (HTC) and said lens filler material (LFM) to said ophthalmic lens blank (OLB);
said focused laser radiation (FLR) output is transmitted to said ophthalmic lens blank (OLB) based on a lens position defined by said lens position identifier (LPI);
said focused laser radiation (FLR) output interacts with said ultraviolet absorber (UVA) within said ophthalmic lens blank (OLB) to change the refractive index of an internal region of said ophthalmic lens blank (OLB); and
said hermetically sealed enclosure (HSE) is configured to be unsealed after said refractive index of said internal region of said ophthalmic lens blank (OLB) has been changed by application of said focused laser radiation (FLR) to said ophthalmic lens blank (OLB).

2. The ophthalmic lens customization system of claim 1 wherein said ophthalmic lens blank (OLB) comprises a material selected from a group consisting of: acrylic; silicon; poly(methyl methacrylate (PMMA); and PMNA plastic.

3. The ophthalmic lens customization system of claim 1 wherein said ophthalmic lens blank (OLB) comprises an ophthalmic lens with known diopter (OKD).

4. The ophthalmic lens customization system of claim 1 wherein said secured lens container (SLC) comprises a material having a refractive index in a range of 1.05 to 1.65.

5. The ophthalmic lens customization system of claim 1 wherein said HSE bottom plate (HBP) comprises a clear or colored material.

6. The ophthalmic lens customization system of claim 1 wherein said HSE top cover (HTC) comprises a material transparent to ultraviolet (UV) radiation.

7. The ophthalmic lens customization system of claim 1 wherein said lens filler material (LFM) comprises a fluid selected from a group consisting of: distilled water; deionized water; and a physiological saline solution.

8. The ophthalmic lens customization system of claim 1 wherein said pulsed laser radiation (PLR) output has energy in a range of 0.01 microjoules to 15.0 microjoules.

9. The ophthalmic lens customization system of claim 1 wherein said pulsed laser radiation (PLR) output has a repetition rate in the range of 0.1 MHz to 100 MHz.

10. The ophthalmic lens customization system of claim 1 wherein said pulsed laser radiation (PLR) output has a pulse width in a range of 10 fs to 950 fs.

11. The ophthalmic lens customization system of claim 1 wherein said focused laser radiation (FLR) output has a spot size in a X-Y directions in a range of 1.0 micrometers to 20.0 micrometers.

12. The ophthalmic lens customization system of claim 1 wherein said focused laser radiation (FLR) output has a spot size in a Z-direction in a range of 0.05 micrometers to 200.0 micrometers.

13. The ophthalmic lens customization system of claim 1 wherein said laser steering scanner (LSS) is configured to distribute said focused laser radiation (FLR) output in a two-dimensional pattern within said ophthalmic lens blank (OLB).

14. The ophthalmic lens customization system of claim 1 wherein said laser steering scanner (LSS) is configured to distribute said focused laser radiation (FLR) output in a three-dimensional pattern within said ophthalmic lens blank (OLB).

15. The ophthalmic lens customization system of claim 1 wherein said laser steering scanner (LSS) is configured to distribute said focused laser radiation (FLR) output in a three-dimensional pattern within said ophthalmic lens blank (OLB), said pattern forming a convex lens within said ophthalmic lens blank (OLB).

16. The ophthalmic lens customization system of claim 1 wherein said laser steering scanner (LSS) is configured to distribute said focused laser radiation (FLR) output in a three-dimensional pattern within said ophthalmic lens blank (OLB), said pattern forming a biconvex lens within said ophthalmic lens blank (OLB).

17. The ophthalmic lens customization system of claim 1 wherein said laser steering scanner (LSS) is configured to distribute said focused laser radiation (FLR) output in a three-dimensional pattern within said ophthalmic lens blank (OLB), said pattern forming a concave lens within said ophthalmic lens blank (OLB).

18. The ophthalmic lens customization system of claim 1 wherein said laser steering scanner (LSS) is configured to distribute said focused laser radiation (FLR) output in a three-dimensional pattern within said ophthalmic lens blank (OLB), said pattern forming a biconcave lens within said ophthalmic lens blank (OLB).

19. The ophthalmic lens customization system of claim 1 wherein said ophthalmic lens blank (OLB) comprises a crosslinked polymeric copolymer.

20. The ophthalmic lens customization system of claim 1 wherein said ophthalmic lens blank (OLB) comprises a crosslinked polymeric acrylic polymer.

21. The ophthalmic lens customization system of claim 1 wherein said pulsed laser source (PLS) further comprises an optic modulator selected from a group consisting of: an Acousto-Optic Modulator (AOM); and a greyscale Acousto-Optic Modulator (AOM).

22. The ophthalmic lens customization system of claim 1 wherein said laser steering scanner (LSS) is configured to distribute said focused laser radiation (FLR) output in a two-dimensional or three-dimensional pattern within said ophthalmic lens blank (OLB); said focused laser radiation creating a hydrophilicity change in a volume associated with said two-dimensional or three-dimensional pattern; and said hydrophilicity change resulting in a corresponding three dimensional change in refractive index of said volume associated with said two-dimensional or three-dimensional pattern.

23. The ophthalmic lens customization system of claim 22 wherein said hydrophilicity change results in a refractive index change within said ophthalmic lens blank (OLB).

24. The ophthalmic lens customization system of claim 22 wherein said refractive index change is greater than 0.01.

25. The ophthalmic lens customization system of claim 22 wherein said two-dimensional or three-dimensional pattern comprises a plurality of layers within said ophthalmic lens blank (OLB).

26. An ophthalmic lens customization method comprising:
(1) impregnating an ophthalmic lens blank (OLB) comprising a clear material with an ultraviolet absorber (UVA); said ophthalmic lens blank (OLB) comprising a blank lens structure (BLS) and lens haptics (BLH);
(2) placing said ophthalmic lens blank (OLB) within a secured lens container (SLC), said secured lens container (SLC) comprising a hermetically sealed enclosure (HSE) having an internal container void (ICV); said HSE comprising a HSE bottom plate (HBP) and a HSE top cover (HTC); and said internal container void (ICV) comprising an internal volume configured to contain said ophthalmic lens blank (OLB); said ophthalmic lens blank (OLB) retained within said internal container void (ICV) via said lens haptics (BLH);
(3) defining the orientation of said ophthalmic lens blank (OLB) within said secured lens container (SLC) with a lens position identifier (LPI);
(4) covering said ophthalmic lens blank (OLB) within said internal container void (ICV) at least in part with a lens filler material (LFM);
(5) hermetically sealing said hermetically sealed enclosure (HSE) after said ophthalmic lens blank (OLB) is retained within said internal container void (ICV) while said lens filler material (LFM) covers at least part of said ophthalmic lens blank (OLB);
(6) sterilizing said ophthalmic lens blank (OLB) within said hermetically sealed enclosure (HSE) after said ophthalmic lens blank (OLB) is retained within said internal container void (ICV) while said lens filler material (LFM) covers at least part of said OLB;
(7) configuring a pulsed laser source (PLS) comprising a femtosecond laser radiation source to emit a pulsed laser radiation (PLR) output;
(8) distributing said pulsed laser radiation (PLR) output across an input area of a focusing microscope objective (FMO) with a laser steering scanner (LSS); said focusing microscope objective (FMO) further comprising a numerical aperture configured to accept said distribution of said pulsed laser radiation (PLR) output across said input area of said focusing microscope objective (FMO) and produce a focused laser radiation (FLR) output;
(9) transmitting said focused laser radiation (FLR) output by said focusing microscope objective (FMO) through said HSE top cover (HTC) and said lens filler material (LFM) to said OLB;
(10) transmitting said focused laser radiation (FLR) output to said ophthalmic lens blank (OLB) based on a lens position defined by said lens position identifier (LPI);
(11) changing the refractive index of an internal region of said ophthalmic lens blank (OLB) via said focused laser radiation (FLR) output interaction with said ultraviolet absorber (UVA) within said ophthalmic lens blank (OLB); and
(12) unsealing said hermetically sealed enclosure (HSE) after said refractive index of said internal region of said ophthalmic lens blank (OLB) has been changed by application of said focused laser radiation (FLR) to said ophthalmic lens blank (OLB).

27. The ophthalmic lens customization method of claim 26 wherein said ophthalmic lens blank (OLB) comprises a material selected from a group consisting of: acrylic; silicon; poly(methyl methacrylate (PMMA); and PMNA plastic.

28. The ophthalmic lens customization method of claim 26 wherein said ophthalmic lens blank (OLB) comprises an ophthalmic lens with known diopter (OKD).

29. The ophthalmic lens customization method of claim 26 wherein said secured lens container (SLC) comprises a material having a refractive index in the range of 1.05 to 1.65.

30. The ophthalmic lens customization method of claim 26 wherein said HSE bottom plate (HBP) comprises a clear or colored material.

31. The ophthalmic lens customization method of claim 26 wherein said HSE top cover (HTC) comprises a material transparent to ultraviolet (UV) radiation.

32. The ophthalmic lens customization method of claim 26 wherein said lens filler material (LFM) comprises a fluid selected from a group consisting of: distilled water; deionized water; and a physiological saline solution.

33. The ophthalmic lens customization method of claim 26 wherein said pulsed laser radiation (PLR) output has energy in a range of 0.01 microjoules to 15.0 microjoules.

34. The ophthalmic lens customization method of claim 26 wherein said pulsed laser radiation (PLR) output has a repetition rate in a range of 0.1 MHz to 100 MHz.

35. The ophthalmic lens customization method of claim 26 wherein said pulsed laser radiation (PLR) output has a pulse width in a range of 10 fs to 950 fs.

36. The ophthalmic lens customization method of claim 26 wherein said focused laser radiation (FLR) output has a spot size in a X-Y directions in a range of 1.0 micrometers to 20.0 micrometers.

37. The ophthalmic lens customization method of claim 26 wherein said focused laser radiation (FLR) output has a spot size in a Z-direction in a range of 0.05 micrometers to 200.0 micrometers.

38. The ophthalmic lens customization method of claim 26 wherein said laser steering scanner (LSS) is configured to distribute said focused laser radiation (FLR) output in a two-dimensional pattern within said ophthalmic lens blank (OLB).

39. The ophthalmic lens customization method of claim 26 wherein said laser steering scanner (LSS) is configured to distribute said focused laser radiation (FLR) output in a three-dimensional pattern within said ophthalmic lens blank (OLB).

40. The ophthalmic lens customization method of claim 26 wherein said laser steering scanner (LSS) is configured to distribute said focused laser radiation (FLR) output in a three-dimensional pattern within said ophthalmic lens blank (OLB), said pattern forming a convex lens within said ophthalmic lens blank (OLB).

41. The ophthalmic lens customization method of claim 26 wherein said laser steering scanner (LSS) is configured to distribute said focused laser radiation (FLR) output in a three-dimensional pattern within said OLB, said pattern forming a biconvex lens within said ophthalmic lens blank (OLB).

42. The ophthalmic lens customization method of claim 26 wherein said laser steering scanner (LSS) is configured to distribute said focused laser radiation (FLR) output in a three-dimensional pattern within said ophthalmic lens blank (OLB), said pattern forming a concave lens within said ophthalmic lens blank (OLB).

43. The ophthalmic lens customization method of claim 26 wherein said laser steering scanner (LSS) is configured to distribute said focused laser radiation (FLR) output in a three-dimensional pattern within said ophthalmic lens blank (OLB), said pattern forming a biconcave lens within said ophthalmic lens blank (OLB).

44. The ophthalmic lens customization method of claim 26 wherein said ophthalmic lens blank (OLB) comprises a crosslinked polymeric copolymer.

45. The ophthalmic lens customization method of claim 26 wherein said ophthalmic lens blank (OLB) comprises a crosslinked polymeric acrylic polymer.

46. The ophthalmic lens customization method of claim 26 wherein said pulsed laser source (PLS) further comprises an optic modulator selected from a group consisting of: an Acousto-Optic Modulator (AOM); and a greyscale Acousto-Optic Modulator (AOM).

47. The ophthalmic lens customization method of claim 26 wherein said laser steering scanner (LSS) is configured to distribute said focused laser radiation (FLR) output in a two-dimensional or three-dimensional pattern within said ophthalmic lens blank (OLB); said focused laser radiation creating a hydrophilicity change in a volume associated with said two-dimensional or three-dimensional pattern; and said hydrophilicity change resulting in a corresponding three dimensional change in refractive index of said volume associated with said two-dimensional or three-dimensional pattern.

48. The ophthalmic lens customization method of claim 47 wherein said hydrophilicity change results in a refractive index change within said ophthalmic lens blank (OLB).

49. The ophthalmic lens customization method of claim 47 wherein said refractive index change is greater than 0.01.

50. The ophthalmic lens customization method of claim 47 wherein said two-dimensional or three-dimensional pattern comprises a plurality of layers within said ophthalmic lens blank (OLB).

* * * * *